(12) United States Patent
Vidal Juan et al.

(10) Patent No.: US 7,855,202 B2
(45) Date of Patent: Dec. 21, 2010

(54) IMIDAZOPYRIDINE DERIVATIVES AS $A_{2B}$ ADENOSINE RECEPTOR ANTAGONISTS

(75) Inventors: Bernat Vidal Juan, Barcelona (ES); Silvia Fonquerna Pou, Barcelona (ES); Paul Robert Eastwood, Barcelona (ES); Jose Aiguade Bosch, Barcelona (ES); Aranzazu Cardus Figueras, Barcelona (ES); Ines Carranco Moruno, Barcelona (ES); Jacob Gonzalez Rodriguez, Barcelona (ES); Sergio Paredes Aparicio, Barcelona (ES)

(73) Assignee: Laboratorios Almirall, S.A., Barcelona (ES)

( * ) Notice: Subject to any disclaimer, the term of this patent is extended or adjusted under 35 U.S.C. 154(b) by 194 days.

(21) Appl. No.: 12/089,050

(22) PCT Filed: Oct. 5, 2006

(86) PCT No.: PCT/EP2006/009620

§ 371 (c)(1),
(2), (4) Date: Jun. 10, 2008

(87) PCT Pub. No.: WO2007/039297

PCT Pub. Date: Apr. 12, 2007

(65) Prior Publication Data

US 2008/0275038 A1 Nov. 6, 2008

(30) Foreign Application Priority Data

Oct. 6, 2005 (ES) ................................. 200502433

(51) Int. Cl.
- *A61K 31/437* (2006.01)
- *A61K 31/506* (2006.01)
- *A61K 31/496* (2006.01)
- *A61P 11/00* (2006.01)
- *A61P 1/00* (2006.01)
- *A61P 9/00* (2006.01)
- *A61P 25/00* (2006.01)
- *A61P 37/00* (2006.01)
- *C07D 471/04* (2006.01)

(52) U.S. Cl. ............... 514/234.2; 514/303; 514/253.04; 514/255.05; 514/256; 546/18; 544/362; 544/405; 544/333; 544/127

(58) Field of Classification Search ............... 514/234.2, 514/303, 253.04, 255.05, 256; 546/18; 544/362, 544/405, 333, 127
See application file for complete search history.

(56) References Cited

U.S. PATENT DOCUMENTS

| 5,763,448 | A | 6/1998 | Carling et al. |
| 5,849,753 | A * | 12/1998 | Yoo et al. ............... 514/303 |
| 5,916,905 | A | 6/1999 | Weier et al. |
| 6,750,232 | B2 | 6/2004 | Harada et al. |
| 6,841,549 | B1 | 1/2005 | Asano et al. |
| 7,396,836 | B2 | 7/2008 | Harada et al. |
| 2003/0229106 | A1 | 12/2003 | Kalla et al. |
| 2004/0006082 | A1 | 1/2004 | Harada et al. |
| 2004/0176399 | A1 | 9/2004 | Elzein et al. |
| 2005/0004149 | A1 | 1/2005 | Harada et al. |
| 2007/0265273 | A1 | 11/2007 | Vidal Juan et al. |
| 2009/0023763 | A1 | 1/2009 | Vidal Juan et al. |
| 2009/0030023 | A1 | 1/2009 | Harada et al. |
| 2009/0042891 | A1 | 2/2009 | Vidal Juan et al. |

FOREIGN PATENT DOCUMENTS

| CA | 2 463 284 | 5/2003 |
| EP | 1 221 444 A1 | 7/2002 |
| EP | 1 283 056 B1 | 2/2003 |
| EP | 1 308 441 | 5/2003 |
| EP | 1 439 175 | 7/2004 |
| WO | WO 97/33883 | 9/1997 |
| WO | WO 98/24782 | 6/1998 |
| WO | WO 99/32448 | 7/1999 |
| WO | WO 99/65897 | 12/1999 |
| WO | WO 00/73307 A2 | 12/2000 |
| WO | WO 01/02400 A1 | 1/2001 |
| WO | WO 01/16134 A1 | 3/2001 |
| WO | WO 01/60350 A2 | 8/2001 |
| WO | WO 01/62233 | 8/2001 |
| WO | WO 02/14282 | 2/2002 |
| WO | WO 02/20495 | 3/2002 |
| WO | WO 02/22608 | 3/2002 |
| WO | WO 02/24893 | 3/2002 |
| WO | WO 02/42298 A1 | 5/2002 |
| WO | WO 03/002566 A1 | 1/2003 |

(Continued)

OTHER PUBLICATIONS

Nadeem et al., American journal of physiology. Lung cellular and molecular physiology, (Jun. 2007) vol. 292, No. 6, pp. L1335-L1344.)*

(Continued)

*Primary Examiner*—D. Margaret Seaman
*Assistant Examiner*—Niloofar Rahmani
(74) *Attorney, Agent, or Firm*—Finnegan, Henderson, Farabow, Garrett & Dunner LLP

(57) ABSTRACT

The present disclosure relates to imidazopyridine derivatives of formula (I):

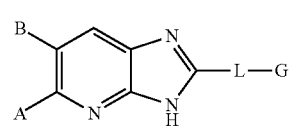

The present disclosure also relates to a method for treating a subject afflicted with a pathological condition or disease susceptible to amelioration by antagonism of the $A_{2B}$ adenosine receptor.

9 Claims, No Drawings

FOREIGN PATENT DOCUMENTS

| WO | WO 03/035639 A1 | 5/2003 |
|---|---|---|
| WO | WO 03/042214 A2 | 5/2003 |
| WO | WO 03/057689 | 7/2003 |
| WO | WO 03/063800 A2 | 8/2003 |
| WO | WO 03/068773 A1 | 8/2003 |
| WO | WO 03/082191 | 10/2003 |
| WO | WO 03/105666 | 12/2003 |
| WO | WO 2004/022540 | 3/2004 |
| WO | WO 2004/030635 | 4/2004 |
| WO | WO 2004/076450 | 9/2004 |
| WO | WO 2004/106337 A1 | 12/2004 |
| WO | WO 2005/021548 A2 | 3/2005 |
| WO | WO 2005/033085 | 4/2005 |
| WO | WO 2005/040151 | 5/2005 |
| WO | WO 2005/040155 | 5/2005 |
| WO | WO 2005/042534 A2 | 5/2005 |
| WO | WO 2005/070926 A1 | 8/2005 |
| WO | WO 2005/100353 A1 | 10/2005 |
| WO | WO 2007/017096 | 2/2007 |
| WO | WO 2008/080461 | 7/2008 |

OTHER PUBLICATIONS

International Search Report mailed Sep. 1, 2007, for International Application No. PCT/EP2006/009620 (WO 2007/039297 A1).
Feoktistov, I. et al. "Adenosine $A_{2B}$ Receptors," *Pharmacological Reviews*, 49(4): 381-402 (1997).
Holgate, S.T. "The identification of the adenosine $A_{2B}$ receptor as a novel therapeutic target in asthma," *British Journal of Pharmacology*, 145: 1009-1015 (2005).
U.S. Appl. No. 12/521,133, Aug. 12, 2009, Bosch et al.
U.S. Appl. No. 10/574,101, Mar. 8, 2007, Vidal Juan et al.
U.S. Appl. No. 11/578,386, Jun. 2, 2008, Vidal Juan et al.
U.S. Appl. No. 11/997,048, Mar. 6, 2008, Vidal Juan et al.
Al-Masoudi, N.A.L. et al. "Nucleosides LIII* Syntheses and Reactions of 6,7-Dipyridyllumazine and 2'-Deoxylumazine N-1 Nucleosides," Pteridines, 4(3): 119-125 (1993).
Barnes, PJ, "Theophylline New Perspectives for an Old Drug," American Journal of Respiratory and Critical Care Medicine, 167: 813-818 (2003).
Bondavalli, Francesco et al., "3-5-diphenyl-1H-pyrazole derivatives IX. 2-substituted 4-phenyl-5-(3,5-diphenyl-1H- pyrazol-1-yl) pyrimidines with platelet antiaggregating and other activities," Il Farmaco, 47(2):171-190 (1992).
Cacciari, Barbara et al., "A2B adenosine receptor antagonists: recent developments," Mini-Reviews in Medicinal Chemistry, 5:1053-1060 (2005).
CAPLUS English Abstract of journal article by Tarkhov, L.I. et al. Accession No. 2005:630607 (2005).
CAPLUS English Abstract of journal article by Tarkhov, L.I. et al. CAS Registry No. 875932-62-0 (2009).
CAPLUS English-language abstract for Ried, Walter et al. "Synthesis of new cyclophanes from pyrazinedicarbonitriles" (1989).
Derwent WPI, Abstract of WO 02/14282 A1, dated Feb. 21, 2002, "New 2-aminopyridine compounds are adenosine receptor antagonists for treating e.g. constipation, irritable bowel syndrome, diabetes, asthma and Parkinson's disease."
Fischer, Gerhard W., et al., "Tetrazole compounds. 8[1]. Synthesis of tetrazolylpyrimidines from tetrazolyl-substituted enamino ketones," J. Heterocyclic Chem., 30:1517-1519 (1993).
Fozard, JR et al. "Adenosine receptor ligands as potential therapeutics in asthma," Current Opinion in Investigational Drugs, 3(1): 69-77 (2002).
Gao et al., Expert Opin. Emerging Drugs (2008) 12(3) 479-492.
Haskö, György, et al., "Adenosine receptors: therapeutic aspects for inflammatory and immune diseases," Nature Reviews, 7:759-770 (2008).
Haskö, György, et al., "Adenosine: an endogenous regulator of innate immunity," Trends in Immunology, 25(1):33-51 (2004).
International Search Report dated Jul. 21, 2005, for Application No. PCT/EP2005/003818.
International Search Report for PCT/EP2004/010664 (WO 2004/040155) dated Dec. 27, 2004.
International Search Report mailed Nov. 22, 2006, for International Application No. PCT/EP2006/007318 (WO 2007/017096 A1).
International Search Report mailed Mar. 3, 2008, for International Application No. PCT/EP2007/010162 (WO 2008/080461 A1).
Jacobson, Kenneth A., et al, "Adenosine receptors as therapeutic targets," Nature Reviews, 5:247-264 (2006).
King, FD "Bioisosteres, Conformational Restriction, and Pro-drugs—Case History: An Example of a Conformational Restriction Approach," Principles and Practice, Chapter 14: 208-225 (1994).
Lappas, CM et al. "Adenosine $A_{2A}$ agonists in development for the treatment of inflammation," Expert Opinion Investig. Drugs, 14(7): 797-806 (2005).
Notice of Allowance dated Aug. 28, 2009 for U.S. Appl. No. 10/574,101.
Notice of Allowance dated Mar. 3, 2010 for U.S. Appl. No. 11/997,048.
Office Action dated Jun. 19, 2009 for U.S. Appl. No. 11/997,048.
Office Action dated Mar. 30, 2009 for U.S. Appl. No. 10/574,101.
Office Action dated Oct. 6, 2008 for U.S. Appl. No. 10/574,101.
Office Action dated Oct. 26, 2009 for U.S. Appl. No. 11/997,048.
Palanki, Moorthy S.S., et al., "Structure-activity relationship studies of ethyl 2-[(3-methy1-2,5,dioxo(3-pyrrolinyl)amino]-4-(trifluoromethyl)pyrimidine-5-carboxylate: An inhibitor of AP-1 and KF-kB Mediated Gene Expression," Bioorganic & Medicinal Chemistry Letters, 12:2573-2577 (2002).
Peart, Jason N., et al., "Adenosinergic cardioprotection: multiple receptors, multiple pathways," Pharmacology & Therapeutics, 114:208-221 (2007).
Polosa, R., "Adenosine-receptor subtypes: their relevance to adenosine-medicated responses in asthma and chronic obstructive pulmonary disease," Eur Respir J., 20:488-496 (2002).
Ried, W. et al. "Synthese neuer Cyclophane aus Pyrazindicabonitrilen," Chemiker-Zeitung, 112(12): 385 (1988).
Restriction Requirement for co-pending U.S. Appl. No. 11/997,048 dated May 1, 2009.
Rusinov, L.V. et al. "Synthesis and Antiviral Activity of 2-Amino-3-Ethoxycarbonylpyrazine Derivatives," Pharmaceutical Chemistry Journal, 39(12): 630-635 (2005).
Schurreit, T. "4-Hydroxy-2H-[1]benzopyran-2on als Baustein zur Synthese von Bisbenzopyranopyridinen," Archiv der Pharmazie (1987) 320:500-506.
Sitkovsky et al. British Journal of Pharmacology (2008) 153:5457-5464.
Tarkhov, LI et al. "Photoluminescence of some indolylpyrazines," Materialovedenie, (4): 16-22 (2005) Not in English but with English abstract (Note—there are 2 English Abstracts—2005 and 2009).
Wilson, CN, "Adenosine receptors and asthma in humans," British Journal of Pharmacology, 155:475-486 (2008).
Zablocki, Jeff, et al., "A2B adenosine receptor antagonists and their potential indications," informa healthcare, 1347-1357 (2006).

* cited by examiner

IMIDAZOPYRIDINE DERIVATIVES AS $A_{2B}$ ADENOSINE RECEPTOR ANTAGONISTS

This application is a national stage filing under 35 U.S.C. §371 of International application Ser. No. PCT/EP2006/009620 filed on Oct. 5, 2006, the contents of which are incorporated herein by reference. This application claims priority of Spanish Patent application Ser. No. P200502433, filed on Oct. 6, 2005.

The present invention relates to new antagonists of the $A_{2B}$ adenosine receptor. These compounds are useful in the treatment, prevention or suppression of diseases and disorders known to be susceptible to improvement by antagonism of the $A_{2B}$ adenosine receptor, such as asthma, chronic obstructive pulmonary disorder, pulmonary fibrosis, emphysema, allergic diseases, inflammation, reperfusion injury, myocardial ischemia, atherosclerosis, hypertension, retinopathy, diabetes mellitus, inflammatory gastrointestinal tract disorders, and/or autoimmune diseases.

Adenosine regulates several physiological functions through specific cell membrane receptors, which are members of the G-protein coupled receptor family. Four distinct adenosine receptors have been identified and classified: $A_1$, $A_{2A}$, $A_{2B}$ and $A_3$.

The $A_{2B}$ adenosine receptor subtype (see Feoktistov, I., Biaggioni, I. Pharmacol. Rev. 1997, 49, 381-402) has been identified in a variety of human and murine tissues and is involved in the regulation of vascular tone, smooth muscle growth, angiogenesis, hepatic glucose production, bowel movement, intestinal secretion, and mast cell degranulation.

In view of the physiological effects mediated by adenosine receptor activation, several $A_{2B}$ receptor antagonists have been recently disclosed for the treatment or prevention of, asthma, bronchoconstriction, allergic diseases, hypertension, atherosclerosis, reperfusion injury, myocardial ischemia, retinopathy, inflammation, gastrointestinal tract disorders, cell proliferation diseases and/or diabetes mellitus. See for example WO2005070926, WO2005042534, WO2005021548, WO2004106337, US2004176399, US2003229106, WO03002566, WO03/063800, WO03/042214, WO 03/035639, WO02/42298, EP 1283056, WO 01/16134, WO 01/02400, WO01/60350, WO 00/73307 or Br. J. Pharmacol. 2005, 145, 1009-1015.

It has now been found that certain imidazopyridine derivatives are novel potent antagonists of the $A_{2B}$ adenosine receptor and can therefore be used in the treatment or prevention of these diseases.

Further objectives of the present invention are to provide a method for preparing said compounds; pharmaceutical compositions comprising an effective amount of said compounds; the use of the compounds in the manufacture of a medicament for the treatment of pathological conditions or diseases susceptible to improvement by antagonism of the $A_{2B}$ adenosine receptor; and methods of treatment of pathological conditions or diseases susceptible to amelioration by antagonism of the $A_{2B}$ adenosine receptor comprising the administration of the compounds of the invention to a subject in need of treatment.

Thus, the present invention is directed to new imidazopyridine derivatives of formula (I)

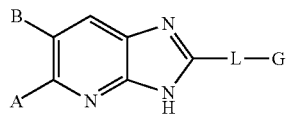

wherein:
A represents a monocyclic nitrogen-containing heteroaryl group optionally substituted by one or more substituents independently selected from the group comprising halogen atoms, $C_{1-4}$alkyl, $C_{3-7}$cycloalkyl, $C_{3-7}$cycloalkyl-$C_{1-4}$alkyl, $C_{1-4}$alkoxy, aryl-$C_{1-4}$alkoxy, $C_{1-4}$alkylthio, mono or di-$C_{1-4}$alkylamino, trifluoromethyl, hydroxy and cyano groups;

B represents a monocyclic nitrogen-containing heteroaryl group optionally substituted by one or more substituents independently selected from the group comprising halogen atoms, $C_{1-4}$alkyl, $C_{3-7}$cycloalkyl, $C_{3-7}$cycloalkyl-$C_{1-4}$alkyl, $C_{1-4}$alkoxy, aryl-$C_{1-4}$alkoxy, $C_{1-4}$alkylthio, mono or di-$C_{1-4}$alkylamino, trifluoromethyl, hydroxy and cyano groups;

L represents a linking group selected from the group comprising direct bond, —(CRR')$_n$—, —NR—, —S—, —O— and —CO—; wherein n is an integer from 0 to 2;

G represent a group selected from the group comprising —H, —OH, $C_{3-7}$ cycloalkyl; $C_{1-6}$ alkyl, aryl, heteroaryl and nitrogen-containing saturated heterocyclic rings, wherein the aryl, heteroaryl and nitrogen-containing saturated heterocyclic groups are unsubstituted or substituted by one or more groups selected from halogen atoms, $C_{1-4}$ alkyl, $C_{1-4}$ alkylthio, $C_{1-4}$ alkoxy, mono- or di-$C_{1-4}$ alkylamino, cyano, trifluoromethyl, —COOH and —CO—O—$C_{1-4}$ alkyl groups;

R and R' are independently selected from hydrogen atoms and $C_{1-4}$ alkyl groups;

and the pharmaceutically acceptable salts and N-oxides thereof.

As used herein the terms alkyl or lower alkyl embrace optionally substituted, linear or branched hydrocarbon radicals having 1 to 8, preferably 1 to 6 and more preferably 1 to 4 carbon atoms. Preferred substituents on the alkyl groups are halogen atoms and hydroxy groups.

Examples include methyl, ethyl, n-propyl, i-propyl, n-butyl, sec-butyl and tert-butyl, n-pentyl, 1-methylbutyl, 2-methylbutyl, isopentyl, 1-ethylpropyl, 1,1-dimethylpropyl, 1,2-dimethylpropyl, n-hexyl, 1-ethylbutyl, 2-ethylbutyl, 1,1-dimethylbutyl, 1,2-dimethylbutyl, 1,3-dimethylbutyl, 2,2-dimethylbutyl, 2,3-dimethylbutyl, 2-methylpentyl, 3-methylpentyl and iso-hexyl radicals.

As used herein, the term cycloalkyl embraces saturated carbocyclic radicals and, unless otherwise specified, a cycloalkyl radical typically has from 3 to 7 carbon atoms.

Examples include cyclopropyl, cyclobutyl, cyclopentyl, cyclohexyl and cycloheptyl. When a cycloalkyl radical carries 2 or more substituents, the substituents may be the same or different. Preferred substituents on the cycloalkyl groups are halogen atoms and hydroxy groups.

As used herein, unless otherwise provided, the term aryl radical embraces typically a $C_5$-$C_{14}$ monocyclic or polycyclic aryl radical such as phenyl or naphthyl, anthranyl or phenanthryl. Optionally substituted phenyl is preferred. When an aryl radical carries 2 or more substituents, the substituents may be the same or different. Preferred substituents on the aryl radicals are halogen atoms and $C_{1-4}$ alkyl, $C_{1-4}$ alkylthio, $C_{1-4}$ alkoxy, mono- or di-$C_{1-4}$ alkylamino, cyano, trifluoromethyl, —COOH and —CO—O—$C_{1-4}$ alkyl groups. Halogen atoms are particularly preferred.

As used herein, unless otherwise provided, the term heteroaryl radical embraces typically a 5- to 14-membered ring system comprising at least one heteroaromatic ring and containing at least one heteroatom selected from O, S and N. The term nitrogen-containing heteroaryl is used to designate heteroaryl groups which comprise at least one nitrogen atom forming part of the ring system. A heteroaryl radical may be a single ring or two or more fused rings wherein at least one ring contains a heteroatom.

Examples of monocyclic heteroaryl radicals include pyridyl, pyrazinyl, pyrimidinyl, pyridazinyl, furyl, oxadiazolyl, oxazolyl, imidazolyl, thiazolyl, thiadiazolyl, thienyl, pyrrolyl, pyridinyl, triazolyl, imidazolidinyl and pyrazolyl radicals. Pyridyl, thienyl, furyl, pyridazinyl and pyrimidinyl radicals are preferred. Pyridyl and pyrimidinyl are the most preferred.

When a heteroaryl radical carries 2 or more substituents, the substituents may be the same or different. Preferred substituents on the heteroaryl radicals are halogen atoms and $C_{1-4}$alkyl, $C_{3-7}$cycloalkyl, $C_{3-7}$cycloalkyl-$C_{1-4}$alkyl, $C_{1-4}$alkoxy, aryl-$C_{1-4}$alkoxy, $C_{1-4}$alkylthio, mono or di-$C_{1-4}$alkylamino, trifluoromethyl, hydroxy —COOH, —CO—O—$C_{1-4}$ alkyl and cyano groups.

As used herein, the term heterocyclic group embraces typically a non-aromatic, saturated or unsaturated $C_3$-$C_{10}$ carbocyclic ring, such as a 5, 6 or 7 membered radical, in which one or more, for example 1, 2, 3 or 4 of the carbon atoms, preferably 1 or 2, of the carbon atoms are replaced by a heteroatom selected from N, O and S. The term nitrogen-containing saturated heterocyclic ring is used to designate saturated heterocyclic groups which comprise at least one nitrogen atom forming part of the ring system. A heterocyclic radical may be a single ring or two or more fused rings wherein at least one ring contains a heteroatom. When a heterocyclyl radical carries 2 or more substituents, the substituents may be the same or different. Preferred substituents on the heterocyclic radicals are halogen atoms and $C_{1-4}$ alkyl, $C_{1-4}$ alkylthio, $C_{1-4}$ alkoxy, mono- or di-$C_{1-4}$ alkylamino, cyano, trifluoromethyl, —COOH and —CO—O—$C_{1-4}$ alkyl groups.

Examples of monocyclic, nitrogen-containing heterocyclic radicals include piperidyl, pyrrolidyl, pyrrolinyl, piperazinyl, morpholinyl, thiomorpholinyl, pyrrolyl, pyrazolinyl, pyrazolidinyl, quinuclidinyl, pyrazolyl. Piperidyl, piperazinyl and morpholinyl are preferred radicals.

As used herein, some of the atoms, radicals, moieties, chains or cycles present in the general structures of the invention are "optionally substituted". This means that these atoms, radicals, moieties, chains or cycles can be either unsubstituted or substituted in any position by one or more, for example 1, 2, 3 or 4, substituents, whereby the hydrogen atoms bound to the unsubstituted atoms, radicals, moieties, chains or cycles are replaced by chemically acceptable atoms, radicals, moieties, chains or cycles. When two or more substituents are present, each substituent may be the same or different.

As used herein, the term halogen atom embraces chlorine, fluorine, bromine or iodine atoms typically a fluorine, chlorine or bromine atom, most preferably chlorine or fluorine. The term halo when used as a prefix has the same meaning.

As used herein, the term pharmaceutically acceptable salt embraces salts with a pharmaceutically acceptable acid or base. Pharmaceutically acceptable acids include both inorganic acids, for example hydrochloric, sulphuric, phosphoric, diphosphoric, hydrobromic, hydroiodic and nitric acid and organic acids, for example citric, fumaric, maleic, malic, mandelic, ascorbic, oxalic, succinic, tartaric, benzoic, acetic, methanesulphonic, ethanesulphonic, benzenesulphonic or p-toluenesulphonic acid. Pharmaceutically acceptable bases include alkali metal (e.g. sodium or potassium) and alkali earth metal (e.g. calcium or magnesium) hydroxides and organic bases, for example alkyl amines, arylalkyl amines and heterocyclic amines.

Other preferred salts according to the invention are quaternary ammonium compounds wherein an equivalent of an anion (X—) is associated with the positive charge of the N atom. X— may be an anion of various mineral acids such as, for example, chloride, bromide, iodide, sulphate, nitrate, phosphate, or an anion of an organic acid such as, for example, acetate, maleate, fumarate, citrate, oxalate, succinate, tartrate, malate, mandelate, trifluoroacetate, methanesulphonate and p-toluenesulphonate. X— is preferably an anion selected from chloride, bromide, iodide, sulphate, nitrate, acetate, maleate, oxalate, succinate or trifluoroacetate. More preferably X— is chloride, bromide, trifluoroacetate or methanesulphonate.

As used herein, an N-oxide is formed from the tertiary basic amines or imines present in the molecule, using a convenient oxidising agent.

Preferred compounds of the invention are those wherein A represents an optionally substituted pyridine or an optionally substituted oxazole group. It is further preferred that A represents a pyridine ring either unsubstituted or substituted with one halogen atom.

In another embodiment of the present invention the group B represents an optionally substituted pyridine or pyrimidine group. It is further preferred that B represents a pyridine group which is unsubstituted or substituted by one or more halogen atoms In an alternative embodiment of the present invention -L-G represents a moeity selected from the group consisting of hydrogen atoms, hydroxyl groups, optionally substituted phenyl, optionally substituted pyridyl, optionally substituted benzyl, optionally substituted benzoyl, $C_{3-7}$ cycloalkyl; $C_{1-6}$ alkyl, optionally substituted morpholino, optionally substituted piperidino and optionally substituted piperazine groups wherein optionally substituted groups may carry from 0 to 2 substituents selected from the group consisting of halogen atoms, $C_{1-4}$alkyl, $C_{1-4}$alkylthio, $C_{1-4}$alkoxy, mono or di-$C_{1-4}$alkylamino, cyano, —(CO)OH, —(CO)O—$C_{1-4}$alkyl, trifluoromethyl, piperidinylmethyl, pyridinylmethyl, phenylamino and piperidinylamino.

Particular individual compounds of the invention for their use in the manufacture of a medicament for the treatment of a pathological condition or disease susceptible to improvement by antagonism of the $A_{2B}$ adenosine receptor include:

6-(3-Fluoropyridin-4-yl)-5-pyridin-3-yl-1,3-dihydro-2H-imidazo[4,5-b]pyridin-2-one 2-Cyclopropyl-6-(3-fluoropyridin-4-yl)-5-pyridin-3-yl-3H-imidazo[4,5-b]pyridine 2-Cyclohexyl-6-(3-fluoropyridin-4-yl)-5-pyridin-3-yl-3H-imidazo[4,5-b]pyridine 6-(3-Fluoropyridin-4-yl)-2-methyl-5-pyridin-3-yl-3H-imidazo[4,5-b]pyridine 2-(4-Fluorophenyl)-6-(3-fluoropyridin-4-yl)-5-pyridin-3-yl-3H-imidazo[4,5-b]pyridine 6-(3-Fluoropyridin-4-yl)-2-(4-methoxyphenyl)-5-pyridin-3-yl-3H-imidazo[4,5-b]pyridine N-{4-[6-(3-fluoropyridin-4-yl)-5-pyridin-3-yl-3H-imidazo[4,5-b]pyridin-2-yl]phenyl}-N,N-dimethylamine 6-(3-Fluoropyridin-4-yl)-2-(4-tert-butylphenyl)-5-pyridin-3-yl-3H-imidazo[4,5-b]pyridine 6-(3-Fluoropyridin-4-yl)-5-pyridin-3-yl-2-[4-(trifluoromethyl)phenyl]-3H-imidazo[4,5-b]pyridine Methyl 4-[6-(3-fluoropyridin-4-yl)-5-pyridin-3-yl-3H-imidazo[4,5-b]pyridin-2-yl]benzoate 4-[6-(3-Fluoropyridin-4-yl)-5-pyridin-3-yl-3H-imidazo[4,5-b]pyridin-2-yl]benzoic acid
6-(3-Fluoropyridin-4-yl)-5-pyridin-3-yl-2-pyridin-4-yl-3H-imidazo[4,5-b]pyridine
2-(2,3-Dihydro-1,4-benzodioxin-6-yl)-6-(3-fluoropyridin-4-yl)-5-pyridin-3-yl-3H-imidazo[4,5-b]pyridine
6-(3-Fluoropyridin-4-yl)-2-[3-fluoro-4-(trifluoromethyl)phenyl]-5-pyridin-3-yl-3H-imidazo[4,5-b]pyridine
2-(2,4-Dichloro-5-fluorophenyl)-6-(3-fluoropyridin-4-yl)-5-pyridin-3-yl-3H-imidazo[4,5-b]pyridine
2-(4-Fluorobenzyl)-6-(3-fluoropyridin-4-yl)-5-pyridin-3-yl-3H-imidazo[4,5-b]pyridine
2-[1-(4-Chlorophenyl)-1-methylethyl]-6-(3-fluoropyridin-4-yl)-5-pyridin-3-yl-3H-imidazo[4,5-b]pyridine
(3,5-Difluorophenyl)[6-(3-fluoropyridin-4-yl)-5-pyridin-3-yl-3H-imidazo[4,5-b]pyridin-2-yl]methanone
N-(4-chlorophenyl)-6-(3-fluoropyridin-4-yl)-5-pyridin-3-yl-3H-imidazo[4,5-b]pyridin-2-amine
2-(4-Fluorophenyl)-5-pyridin-3-yl-6-pyridin-4-yl-3H-imidazo[4,5-b]pyridine
6-(3-Chloropyridin-4-yl)-5-pyridin-3-yl-1,3-dihydro-2H-imidazo[4,5-b]pyridin-2-one
5,6-Dipyridin-4-yl-1,3-dihydro-2H-imidazo[4,5-b]pyridin-2-one
5-(3-Fluoropyridin-4-yl)-6-pyridin-4-yl-1,3-dihydro-2H-imidazo[4,5-b]pyridin-2-one
5-(3-Chloropyridin-4-yl)-6-pyridin-4-yl-1,3-dihydro-2H-imidazo[4,5-b]pyridin-2-one
5-(3-Chloropyridin-4-yl)-2-(4-fluorophenyl)-6-pyridin-4-yl-3H-imidazo[4,5-b]pyridine
6-(3-Chloropyridin-4-yl)-5-pyridin-4-yl-1,3-dihydro-2H-imidazo[4,5-b]pyridin-2-one
6-(3-Chloropyridin-4-yl)-2-(4-fluorophenyl)-5-pyridin-4-yl-3H-imidazo[4,5-b]pyridine
5-(3-Chloropyridin-4-yl)-2-(4-fluorophenyl)-6-(3-fluoropyridin-4-yl)-3H-imidazo[4,5-b]pyridine
5,6-Bis(3-chloropyridin-4-yl)-1,3-dihydro-2H-imidazo[4,5-b]pyridin-2-one
5-(1,3-Oxazol-2-yl)-6-pyridin-4-yl-1,3-dihydro-2H-imidazo[4,5-b]pyridin-2-one
5-(1,3-Oxazol-2-yl)-6-pyridin-4-yl-3H-imidazo[4,5-b]pyridine
6-(3-Fluoropyridin-4-yl)-5-(1,3-oxazol-2-yl)-1,3-dihydro-2H-imidazo[4,5-b]pyridin-2-one
6-(3-Fluoropyridin-4-yl)-5-(1,3-oxazol-2-yl)-3H-imidazo[4,5-b]pyridine
5-(1,3-Oxazol-5-yl)-6-pyridin-4-yl-1,3-dihydro-2H-imidazo[4,5-b]pyridin-2-one
5-(1,3-Oxazol-5-yl)-6-pyridin-4-yl-3H-imidazo[4,5-b]pyridine
6-(3-Fluoropyridin-4-yl)-5-(1,3-oxazol-5-yl)-3H-imidazo[4,5-b]pyridine
2-(3-Fluoro-4-methylphenyl)-6-(3-fluoropyridin-4-yl)-5-pyridin-3-yl-3H-imidazo[4,5-b]pyridine.
2-(3-Fluorophenyl)-6-(3-fluoropyridin-4-yl)-5-pyridin-3-yl-3H-imidazo[4,5-b]pyridine
6-(3-Fluoropyridin-4-yl)-2,5-dipyridin-3-yl-3H-imidazo[4,5-b]pyridine
6-(3-Fluoropyridin-4-yl)-2-pyrazin-2-yl-5-pyridin-3-yl-3H-imidazo[4,5-b]pyridine
3-[6-(3-Fluoropyridin-4-yl)-5-pyridin-3-yl-3H-imidazo[4,5-b]pyridin-2-yl]benzonitrile
3-[6-(3-Fluoropyridin-4-yl)-5-pyridin-3-yl-3H-imidazo[4,5-b]pyridin-2-yl]benzoic acid;
6-(3-Fluoropyridin-4-yl)-5-pyridin-3-yl-2-pyrimidin-5-yl-3H-imidazo[4,5-b]pyridine
6-(3-Fluoropyridin-4-yl)-2-pyridin-2-yl-5-pyridin-3-yl-3H-imidazo[4,5-b]pyridine
2-(3-Chloropyridin-4-yl)-6-(3-fluoropyridin-4-yl)-5-pyridin-3-yl-3H-imidazo[4,5-b]pyridine
6-(3-Fluoropyridin-4-yl)-2-(1-methyl-1H-imidazol-5-yl)-5-pyridin-3-yl-3H-imidazo[4,5-b]pyridine
6-(3-Fluoropyridin-4-yl)-2-(methylthio)-5-pyridin-3-yl-3H-imidazo[4,5-b]pyridine
1-[6-(3-Fluoropyridin-4-yl)-5-pyridin-3-yl-3H-imidazo[4,5-b]pyridin-2-yl]-1H-pyrazole-4-carboxylic acid
6-(3-Fluoropyridin-4-yl)-2-(1-methyl-1H-pyrazol-5-yl)-5-pyridin-3-yl-3H-imidazo[4,5-b]pyridine
6-(3-Fluoropyridin-4-yl)-2-[1-methyl-3-(trifluoromethyl)-1H-pyrazol-5-yl]-5-pyridin-3-yl-3H-imidazo[4,5-b]pyridine
2-(3,5-Dimethyl-1H-pyrazol-1-yl)-6-(3-fluoropyridin-4-yl)-5-pyridin-3-yl-3H-imidazo[4,5-b]pyridine
6-(3-Fluoropyridin-4-yl)-5-pyridin-3-yl-2-(4H-1,2,4-triazol-3-yl)-3H-imidazo[4,5-b]pyridine
6-(3-Fluoropyridin-4-yl)-2-morpholin-4-yl-5-pyridin-3-yl-3H-imidazo[4,5-b]pyridine
6-(3-Fluoropyridin-4-yl)-2-piperidin-1-yl-5-pyridin-3-yl-3H-imidazo[4,5-b]pyridine
6-(3-Fluoropyridin-4-yl)-2-(4-methylpiperazin-1-yl)-5-pyridin-3-yl-3H-imidazo[4,5-b]pyridine
6-(3-Fluoropyridin-4-yl)-5-pyridin-3-yl-3H-imidazo[4,5-b]pyridin-2-amine
6-(3-Fluoropyridin-4-yl)-5-pyridin-3-yl-2-[3-(trifluoromethyl)benzyl]-3H-imidazo[4,5-b]pyridine
6-(3-Fluoropyridin-4-yl)-2-(2-phenylethyl)-5-pyridin-3-yl-3H-imidazo[4,5-b]pyridine
6-(3-Fluoropyridin-4-yl)-5-pyridin-3-yl-2-(2-pyridin-3-ylethyl)-3H-imidazo[4,5-b]pyridine
2-[1-(4-Chlorophenyl)ethyl]-6-(3-fluoropyridin-4-yl)-5-pyridin-3-yl-3H-imidazo[4,5-b]pyridine
4-{2-[6-(3-Fluoro-pyridin-4-yl)-5-pyridin-3-yl-3H-imidazo[4,5-b]pyridin-2-yl]-ethyl}-benzoic acid
6-(3-Fluoropyridin-4-yl)-N,5-dipyridin-3-yl-3H-imidazo[4,5-b]pyridin-2-amine
N-(4-Fluorophenyl)-6-(3-fluoropyridin-4-yl)-5-pyridin-3-yl-3H-imidazo[4,5-b]pyridin-2-amine
4-{[6-(3-Fluoropyridin-4-yl)-5-pyridin-3-yl-3H-imidazo[4,5-b]pyridin-2-yl]amino}benzoic acid
6-(3,5-Difluoropyridin-4-yl)-2-(4-fluorophenyl)-5-pyridin-3-yl-3H-imidazo[4,5-b]pyridine
4-[6-(3,5-Difluoropyridin-4-yl)-5-pyridin-3-yl-3H-imidazo[4,5-b]pyridin-2-yl]benzoic acid
6-(3,5-Difluoropyridin-4-yl)-5-pyridin-3-yl-1,3-dihydro-2H-imidazo[4,5-b]pyridin-2-one Of outstanding interest are:
5-(3-Fluoropyridin-4-yl)-6-pyridin-4-yl-1,3-dihydro-2H-imidazo[4,5-b]pyridin-2-one
6-(3-Fluoropyridin-4-yl)-5-(1,3-oxazol-2-yl)-1,3-dihydro-2H-imidazo[4,5-b]pyridin-2-one
4-[6-(3-Fluoropyridin-4-yl)-5-pyridin-3-yl-3H-imidazo[4,5-b]pyridin-2-yl]benzoic acid
6-(3-Fluoropyridin-4-yl)-2-(4-methoxyphenyl)-5-pyridin-3-yl-3H-imidazo[4,5-b]pyridine
N-{4-[6-(3-fluoropyridin-4-yl)-5-pyridin-3-yl-3H-imidazo[4,5-b]pyridin-2-yl]phenyl}-N,N-dimethylamine
6-(3-Fluoropyridin-4-yl)-5-pyridin-3-yl-2-pyridin-4-yl-3H-imidazo[4,5-b]pyridine
2-(4-Fluorobenzyl)-6-(3-fluoropyridin-4-yl)-5-pyridin-3-yl-3H-imidazo[4,5-b]pyridine
2-(3-Fluoro-4-methylphenyl)-6-(3-fluoropyridin-4-yl)-5-pyridin-3-yl-3H-imidazo[4,5-b]pyridine.

2-(3-Fluorophenyl)-6-(3-fluoropyridin-4-yl)-5-pyridin-3-yl-3H-imidazo[4,5-b]pyridine 6-(3-Fluoropyridin-4-yl)-2,5-dipyridin-3-yl-3H-imidazo[4,5-b]pyridine 6-(3-Fluoropyridin-4-yl)-2-(1-methyl-1H-imidazol-5-yl)-5-pyridin-3-yl-3H-imidazo[4,5-b]pyridine 6-(3,5-Difluoropyridin-4-yl)-2-(4-fluorophenyl)-5-pyridin-3-yl-3H-imidazo[4,5-b]pyridine 4-[6-(3,5-Difluoropyridin-4-yl)-5-pyridin-3-yl-3H-imidazo[4,5-b]pyridin-2-yl]benzoic acid 6-(3,5-Difluoropyridin-4-yl)-5-pyridin-3-yl-1,3-dihydro-2H-imidazo[4,5-b]pyridin-2-one Compounds of general formula (I) and in particular those wherein A, B are as defined in claim 1 and L represents a linking group selected from the group comprising direct bond, —(CRR')$_n$— or —CO— and G represents a group selected from the group comprising —H, —OH (general formula (XI)), $C_{3-7}$ cycloalkyl; $C_{1-4}$ alkyl, aryl, heteroaryl and nitrogen-containing saturated heterocyclic rings (general formula (XII)) may be prepared following the synthetic scheme depicted in scheme 1.

such as tetrakis(triphenylphosphine)palladium(0), [1,1'-bis(diphenylphosphino)ferrocene]palladium(II) dichloride dichloromethane complex (1:1) or bis(triphenylphosphine)palladium(II) dichloride in solvents such as toluene, dioxane in the presence of an aqueous solution of a base such as sodium or caesium carbonate and at a temperature between 25° C. to 110° C., or in solvents such as DMF using a copper catalyst and at a temperature between 25° C. to 150° C. provides compounds of general formula (IV).

Step c

A further Suzuki, Negishi or Stille-type coupling using the corresponding boronic acid or boronate derivative, the arylzinc derivative or the trialkyltin (preferably tributyltin) derivative of A under the standard procedures for Pd catalyzed reactions described above provides the 2-amino-3-nitropyridines (V).

Steps d and e

Alternatively, regioselective Suzuki, Stille or Negishy-type coupling of the corresponding derivative of A with 6-chloro-3-nitropyridin-2-amine (II), using the standard pro-

SCHEME 1

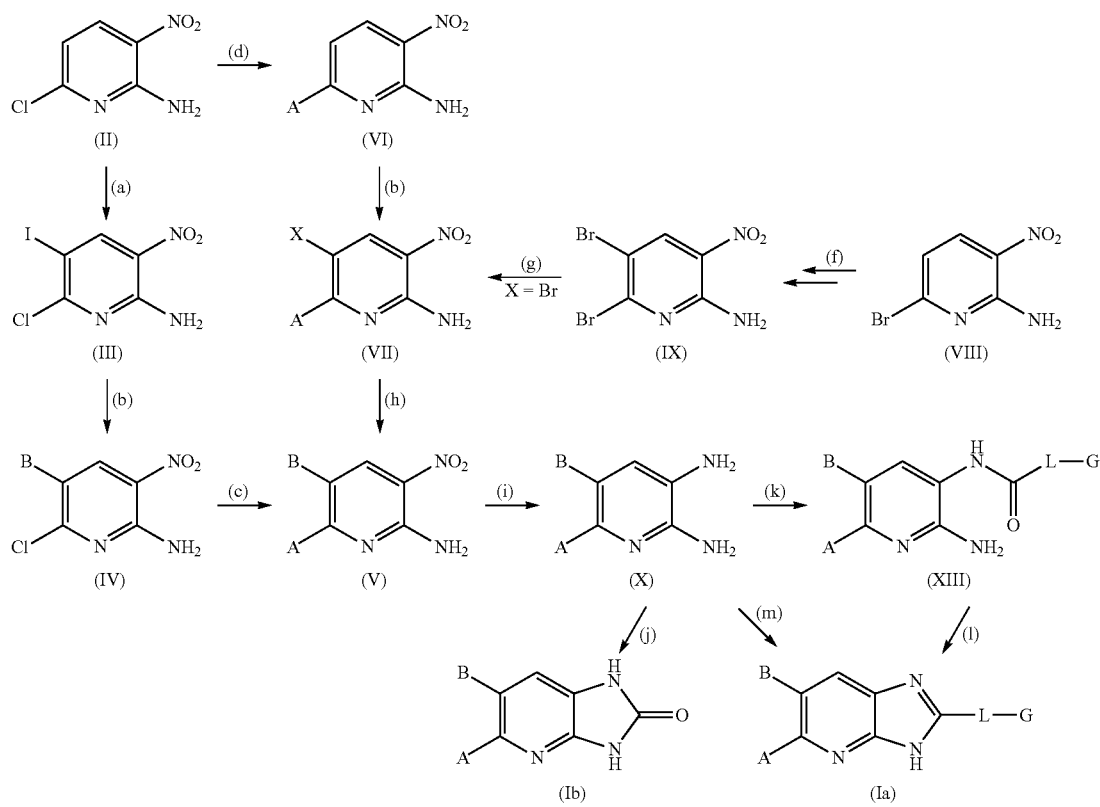

Step a

Halogenation of 6-chloro-3-nitropyridin-2-amine (II) using reagents such as I2 or N-halosuccinimide in polar aprotic solvents such as DMF or mixtures of solvents DMSO:H$_2$O and at temperatures ranging from 0° C. to 100° C. yields dihalonitropyridin-2-amines (III).

Step b

Regioselective Suzuki or Stille-type coupling with the boronic acid or boronate derivative or the trialkyltin (preferably tributyltin) derivative of B using a palladium catalyst cedures for Pd catalyzed reactions described above, provides compounds of general formula (VI), which upon a halogenation step using the same protocols described above provides compounds of general formula (VII).

Steps f and g

Dihalopyridine derivatives (IX) are prepared by halogenation of 6-halopyridine derivatives (VIII) using reagents such as Br$_2$ or N-halosuccinimide in polar aprotic solvents such as DMF and at temperatures ranging from 0° C. to 100° C., to yield dihaloaminopyridines (not shown). These products are in turn nitrated in a two step process involving nitration of the amino group in a mixture of sulphuric and nitric acid in a temperature range between −10° C. to 0° C. followed by a sulfuric acid promoted rearrangement of the nitro group to produce compounds of formula (IX). A further regioselective Suzuki, Negishi or Stille-type coupling with the corresponding derivative of A and using the standard procedures for Pd catalyzed reactions described above provides compounds of general formula (VII).

Step m

Alternatively, diamino derivatives (X) can be cyclized to the imidazopyridines (Ia) by heating in neat trialkylorthoacid or in an acetic acid solution of the orthoacid derivatives or by using an acyl chloride (Cl-CO-L-G) and a solvent such as pyridine and at temperatures between 70° C. and 200° C.

By following another synthetic pathway (Scheme 2), intermediates (V) can also be accessed starting from 2,6-dichloro-3-nitropyridine (XIV)

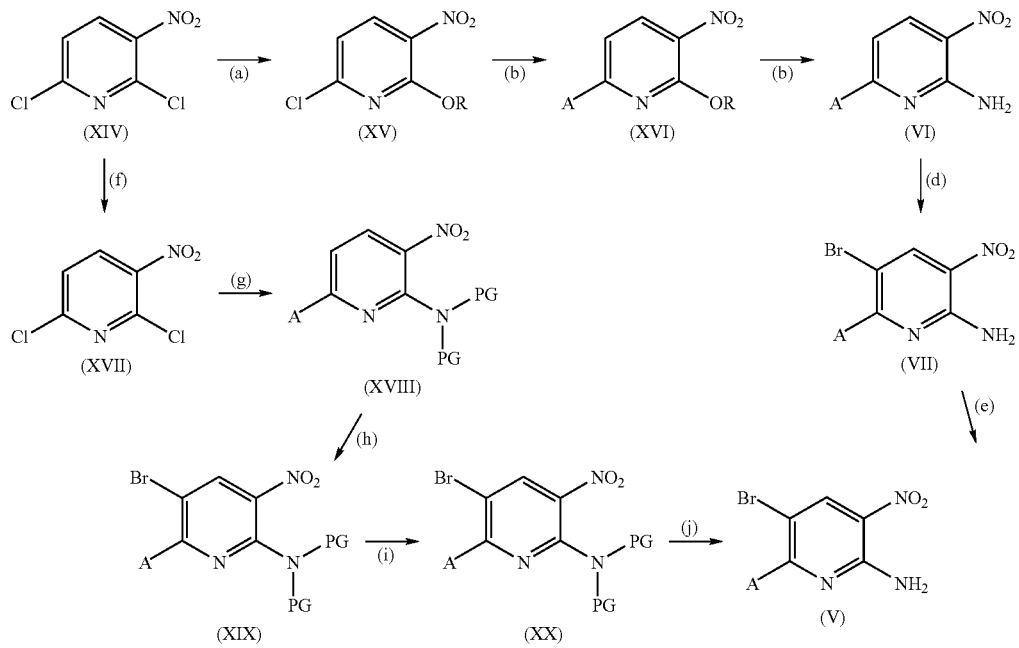

SCHEME 2

Steps h and i

A further Suzuki or Stille-type coupling with the corresponding derivative of B described above provides compounds of general formula (V). Reduction of the nitro group using standard hydrogenation conditions in the presence of hydrogen and using Pd on carbon as a catalyst provides the diamino derivatives (X). Alternatively, the reduction of the nitro group can also be accomplished by treatment with iron in the presence of hydrochloric acid in solvents such as ethanol.

Step j

Treatment of (X) with carbonylating agents such as carbonyldiimidazole in polar aprotic solvents such as DMF or THF in the presence or absence of a base such as sodium hydride or triethylamine and heating at temperatures between 50° C. and 200° C. provides the imidazolone compounds (Ib).

Steps k and l

Treatment of compounds of formula (X) with acylating agents such as anhydrides, acid chlorides or acylcarbonates in apolar organic solvents such as THF and in the presence of a convenient organic base (such as triethylamine) or inorganic base, and eventually acylating with carboxylic acids using coupling agents such as dimethylcarbodiimide, yields the compounds of formula (XIII), which can be converted into the compounds of formula (Ia) by acid (for example acetic acid) or base (for example sodium hydroxide) catalyzed cyclization at temperatures between 70° C. and 200° C.

Steps a to e

Displacement of the 2-chloro functionality of (XIV) with an alcohol, preferably methyl alcohol, in the presence of a base, preferably sodium hydride, in an organic solvent such as xylene leads to compounds of formula (XV). Reaction of (XV) under typical cross-coupling conditions with, for example, an aryl boronic acid or an aryl stannane, preferably a tributyl stannane, in the presence of a palladium catalyst such as such as tetrakis(triphenylphosphine)palladium(0) or [1,1'-bis(diphenylphosphino)ferrocene]palladium(II) dichloride dichloromethane complex (1:1) in solvents such as toluene or dioxane at temperatures ranging from 80° C.-120° C. gives rise to intermediates of type (XVI). Displacement of the alkoxy functionality of (XVI) by heating with concentrated aqueous ammonia at temperatures ranging from 80° C.-120° C. in a sealed vessel gives rise to intermediates of type (VI) which can be elaborated to intermediates (V) by using the protocols outlined in Scheme 1.

Steps f to j

Intermediates of type (V) can also be accessed via an alternative route (Scheme 2) starting from 2,6-dichloro-3-nitropyridine (XIV) Displacement of the 2-chloro functionality with a suitable secondary aliphatic amine, such as N,N-di(4-methoxy)benzylamine, in a suitable solvent such as chloroform in the presence of an organic base such as triethylamine, at temperatures ranging from 0° C. to 25° C. gives to rise to intermediates of type (XVII), which may be considered a nitrogen protected version of compound (II). Reaction of (XVII) under typical cross-coupling conditions with, for example, an aryl boronic acid or an aryl stannane in the presence of a palladium catalyst such as such as tetrakis (triphenylphosphine)palladium(0) or [1,1'-bis(diphenylphosphino)ferrocene]palladium(II) dichloride dichloromethane complex (1:1) in solvents such as toluene or dioxane at temperatures ranging from 80° C.-120° C. gives rise to intermediates of type (XVIII) which can be halogenated using reagents such as Br$_2$ or N-halosuccinimide in polar aprotic solvents such as DMF and at temperatures ranging from 0° C. to 100° C., to yield compounds (XIX). A second palladium catalyzed cross coupling reaction give rise to intermediates (XX) which can be deprotected with, for example, trifluoroacetic acid in dichloromethane, to give the desired intermediates (V).

Compounds of general formula (Ib) corresponding to compounds of formula (I) wherein L is a direct bond, G is a hydroxy group and A and B as defined in claim 1, may be prepared following the synthetic scheme depicted in scheme 3.

Steps c to e

The ketones of formula (XXIII) are then reacted in neat N,N-dimethylformamide dialkyl acetal, such as dimethylacetal, at a temperature range between room temperature and 150° C. to yield the dimethylamino α,β unsaturated ketone of formula (XXVI) which can be converted into the 2-oxo-1,2-dihydropyridine-3-carbonitriles of formula (XXVII) by cyclization in the presence of cyanoacetamide using alkoxides such as sodium methoxide in polar aprotic solvents such as dimethylformamide and at temperatures between 50° C. to 150° C. These compounds may be converted into the 2-chloronicotinonitriles of formula (XXVIII) by treatment of the resulting pyridone (XXVII) with chlorinating agents such as POCl$_3$, PCl$_5$ and PhPOCl$_2$ or by using a combination of such reagents.

Steps f to h

2-Chloronicotinonitriles of formula (XXVIII) may be reacted with a saturated solution of ammonia in an organic

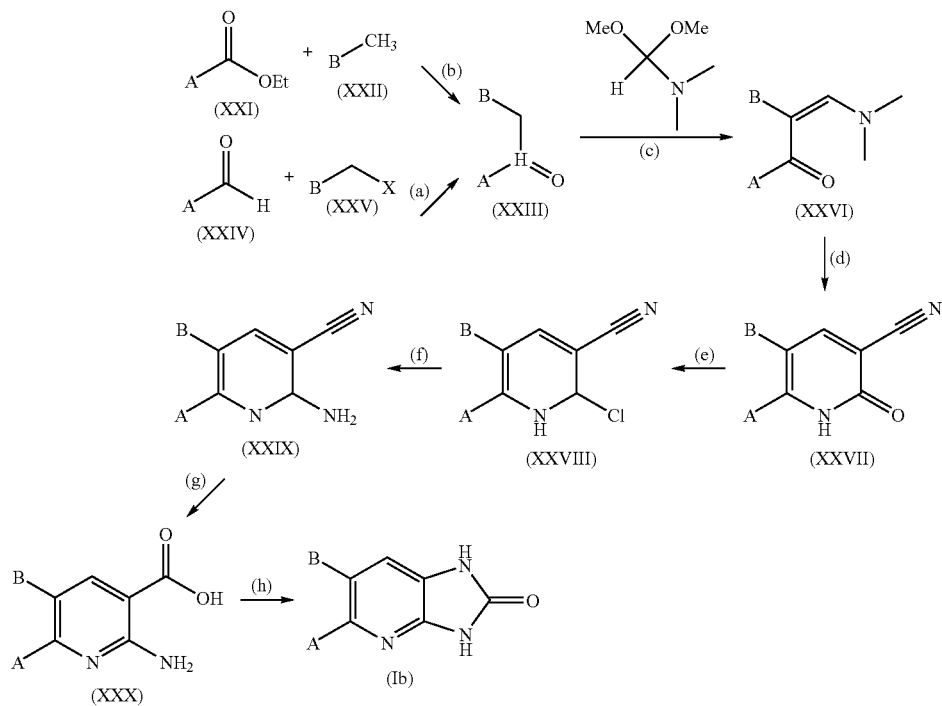

SCHEME 3

Step a

The aldehydes of formula (XXIV) are reacted with the halomethyl derivatives of formula (XXV) to yield the ketones of formula (XXIII) either via cyanohydrin intermediates or in a two step process involving addition of an organometallic derivative of (XXV), preferably magnesium or zinc derivative, followed by reoxidation of the resulting alcohol using oxidizing agents such as manganese (IV) oxide.

Step b

Alternatively the ketones of formula (XXIII) may be obtained by condensation of the ethyl esters of formula (XXI) with the compounds of formula (XXII). This reaction is conveniently carried out in the presence of an organic base such as lithium bis(trimethylsilyl)amide in a range of temperature about −10° C. to about 50° C. and in organic aprotic solvents, preferably tetrahydrofuran or diethyl ether.

solvent, preferably ethanol, at a temperature between 25° C. to 150° C. to yield the compounds of formula (XXIX). Hydrolysis of compounds (XXIX) to the carboxylic acid of formula (XXX) can be achieved with a base such as potassium hydroxide in aqueous or organic solvents such as ethylene glycol and at a temperature between 50° C. to 200° C. Alternatively this conversion could be achieved under aqueous acidic media such as 6M sulphuric acid. These compounds may be subjected to Curtius rearrangement by formation and rearrangement of the acyl azide derivative which may be formed by reacting (XXX) with diphenylphosphoryl azide (or sodium azide with activated acid) in an organic solvent compatible with these reaction conditions (e.g. dioxane) and at a range of temperature between 0° C. to 30° C. followed by heating at a temperature ranging between 50° C.

to 200° C., with in situ formation of the target pyridoimidazolone ring yielding compounds of formula (Ib).

Compounds of general formula (I) and in particular those wherein A, B are as defined in claim 1 and L represents a linking group selected from the group comprising —NR—, —S— or —O— and G represents a group selected from the group comprising $C_{3-7}$ cycloalkyl; $C_{1-4}$ alkyl, aryl, heteroaryl and nitrogen-containing saturated heterocyclic rings may be prepared following the synthetic scheme depicted in scheme 4.

oxalyl chloride or phosphorus chloride at a temperature ranging from 20° to 150° C. and then with an aryl or alkyl thiol at a temperature between 60° to 150° C. Additionally, compounds of general formula (Ie) where G is an alkyl or cycloalkyl group can be prepared by reaction of diamines (X) with 1,1'-thiocarbonyldiimidazole followed by alkylation using the corresponding alkylhalides. Compounds (Ie) can then be heated up at a temperature between 60° C. and 150° C. in the presence of the primary or secondary amine to afford compounds of general formula (Ic). In some cases, oxidation

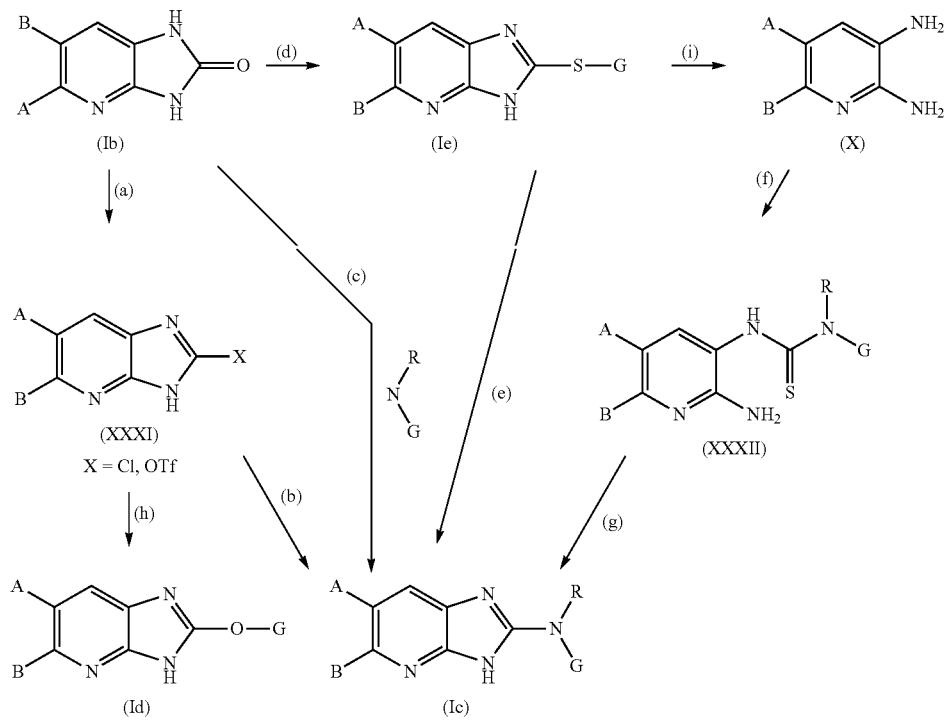

SCHEME 4

Steps a to c

Compounds of general formula (XXXI) can be prepared from imidazolones (Ib) using reagents such as oxalyl chloride, phosphorus oxychloride, phosphorus pentachloride or a combination of them at a temperature ranging from 20° to 150° C. in a solvent like dichloromethane or acetonitrile. Alternatively, compounds (XXXI) may be prepared by treating imidazolones (Ib) with sodium hydride and then with trifluoromethansulfonyl chloride, trifluoromethansulphonyl anhydride or N-phenyl-bis(trifluoroethansulfonimide) in dimethylformamide at a range of temperatures between 20° C. and 150° C. Compounds of general formula (XXXI) can be treated with primary or secondary amines at a range of temperatures between 40° and 170° C. to give compounds of general formula (Ic). Alternatively, compounds of general formula (Ic) may be obtained by heating imidazolones (Ib) in the presence of a primary or secondary amine and a dehydrating agent like magnesium sulphate or molecular sieves.

Steps d, e and i

On the other hand, compounds of general formula (Ie) can be prepared from imidazolones (Ib) using reagents such as to the corresponding sulfone or the use of catalytic Lewis acid such as zinc chloride may be needed.

Steps f and g

Diamines (X) may be treated with alkyl or aryl isothiocianates to give the thioureas of general formula (XXXII). Thioureas of formula (XXXII) can be treated with alkylcarbodiimides at room temperature or with the assistance of the microwaves to give compounds of general formula (Ic). Alternatively, thioureas of general formula (XXXII) may be treated under reductive conditions such as mercury oxide and sulphur to give compounds of general formula (Ic).

Step h

Compounds of general formula (Id) can be prepared by treating compounds of formula (XXXI) with aryloxy or alkyloxy nucleophiles such as sodium methoxide or lithium phenyl. Alternatively, compounds of general formula (Id) may be prepared from imidazolones (Ib) using sodium or potassium hydride and alkyl or arylalkyl halides or trifaltes in a solvent such as dimethylformamide or tetrahydrofuran in a range of temperatures between −78° to 100° C.

EXPERIMENTAL

Pharmacological Activity

Adenosine 2B Receptor Subtype Competition Radioligand Binding Assay

A2B membranes were prepared from HEK293 cells stably expressing the human A2B receptor that were purchased from Euroscreen (ES-013-C). Competition assays were carried out incubating in polypropylene 96 well-plates (no 267245, NUNC) containing 2 µl of either 1% DMSO solution, test compound or 100 µM 5'NECA (SIGMA E-2387) for non-specific binding, 100 µg of A2B-membranes (prepared in Tris-HCl 50 mM pH 6.5, $MgCl_2$ 10 mM, EDTA 1 mM, benzamidine 0.1 mM; buffer A) and 35 nM [$^3$H]-DPCPX (TRK1064, 128 Ci/mmol, Amersham), in a total volume of 200 µl of buffer A+2 UI/ml adenosine deaminase, for 60 minutes at room temperature. At the end of the incubation, samples were transferred to a GF/C filter plates (Milipore MAFCNOB50) pretreated for 15 min. with 250 µl of Tris-HCl 50 mM pH 6.5 (Buffer B). Samples were then filtered 4 times with 250 µl of buffer B. Samples were counted using 30 µl of Hisafe II (Perkin Elmer) in a Trilux counter.

Table 1 shows the binding activities of some of the compounds of the present invention determined using the adenosine 2B receptor subtype competition radioligand binding assay described above.

TABLE 1

| Example | $K_i$ |
|---|---|
| 6 | 0.8 |
| 7 | 1.7 |
| 11 | 8 |
| 12 | 1.8 |
| 16 | 24 |
| 23 | 7 |
| 32 | 24 |
| 37 | 2.2 |
| 38 | 2.8 |
| 39 | 3.8 |
| 46 | 9.5 |
| 65 | 2.8 |
| 66 | 23 |
| 67 | 26 |

The compounds of formula (I) have been tested according to the assay described above and have shown to be potent inhibitors of the $A_{2B}$ adenosine receptor subtype. Preferred imidazopyridine derivatives of the invention possess a $K_i$ value for the antagonism of $A_{2B}$ (determined as defined above) of less than 50 nM, preferably less than 10 nM and more preferably less than 5 nM.

The imidazopyridine derivatives of the invention are useful in the treatment or prevention of diseases known to be susceptible to improvement by treatment with an antagonist of the $A_{2B}$ adenosine receptor. Such diseases include but are not limited to asthma, chronic obstructive pulmonary disorder, pulmonary fibrosis, emphysema, allergic diseases, inflammation, reperfusion injury, myocardial ischemia, atherosclerosis, hypertension, retinopathy, diabetes mellitus, inflammatory gastrointestinal tract disorders, and/or autoimmune diseases. Examples of autoimmune diseases which can be treated or prevented using the compounds of the invention are Addison's disease, autoimmune hemolytic anemia, Crohn's disease, Goodpasture's syndrome, Graves disease, Hashimoto's thyroiditis, idiopathic thrombocytopenic purpura, insulin-dependent diabetes mellitus, multiple sclerosis, myasthenia gravis, pemphigus vulgaris, pernicious anemia, poststreptococcal glomerulonephritis, psoriasis, rheumatoid arthritis, scleroderma, Sjogren's syndrome, spontaneous infertility, and systemic lupus erythematosus.

Accordingly, the imidazopyridine derivatives of the invention and pharmaceutical compositions comprising such compounds and/or salts thereof may be used in a method of treatment of disorders of the human or animal body which comprises administering to a subject requiring such treatment an effective amount of imidazopyridine derivative of the invention or a pharmaceutically acceptable salt thereof.

When imidazopyridine derivatives of the invention are used for the treatment of respiratory diseases such as asthma, chronic obstructive pulmonary disorder, pulmonary fibrosis or emphysema it may be advantageous to use them in combination with other active compounds known to be useful in the treatment of respiratory diseases such as (1) antagonists of M3 muscarinic receptors, (2) β2-agonists, (3) PDE4 inhibitors, (4) cortiocosteroids, (5) leukotriene D4 antagonists, (6) inhibitors of egfr-kinase, (7) p38 kinase inhibitors, (8) NK1 receptor agonists, (9) CRTh2 antagonists, (10) syk kinase inhibitors, (11) CCR3 antagonists and (12) VLA-4 antagonists.

Thus, the present invention also provides pharmaceutical compositions comprising a imidazopyridine derivative of the invention and another active compound selected from the groups consisting of (1) antagonists of M3 muscarinic receptors, (2) β2-agonists, (3) PDE 4 inhibitors, (4) cortiocosteroids, (5) leukotriene D4 antagonists, (6) inhibitors of egfr-kinase, (7) p38 kinase inhibitors, (8) NK1 receptor agonists, (9) CRTh2 antagonists, (10) syk kinase inhibitors, (11) CCR3 antagonists and (12) VLA-4 antagonists.

The present invention also provides pharmaceutical compositions which comprise, as an active ingredient, at least a imidazopyridine derivative of formula (I) in association with a pharmaceutically acceptable excipient such as a carrier or diluent. The active ingredient may comprise 0.001% to 99% by weight, preferably 0.01% to 90% by weight of the composition depending upon the nature of the formulation and whether further dilution is to be made prior to application. Preferably the compositions are made up in a form suitable for oral, topical, nasal, rectal, percutaneous, injectable administration or inhalation.

The pharmaceutically acceptable excipients which are admixed with the active compound or salts of such compound, to form the compositions of this invention are well-known per se and the actual excipients used depend inter alia on the intended method of administering the compositions.

Compositions of this invention are preferably adapted for inhaled, injectable or oral administration. The compositions for oral administration may take the form of tablets, retard tablets, sublingual tablets, capsules or liquid preparations, such as mixtures, elixirs, syrups or suspensions. The compositions for inhalation may take the form of inhalation aerosols, inhalation solutions or dry powders for inhalation all containing the compound of the invention; such preparations may be made by methods well-known in the art.

The diluents which may be used in the preparation of the compositions include those liquid and solid diluents which are compatible with the active ingredient, together with colouring or flavouring agents, if desired. Tablets or capsules may conveniently contain between 2 and 500 mg of active ingredient or the equivalent amount of a salt thereof.

The liquid composition adapted for oral use may be in the form of solutions or suspensions. The solutions may be aqueous solutions of a soluble salt or other derivative of the active compound in association with, for example, sucrose to form a syrup. The suspensions may comprise an insoluble active compound of the invention or a pharmaceutically acceptable salt thereof in association with water, together with a suspending agent or flavouring agent.

Compositions for parenteral injection may be prepared from soluble salts, which may or may not be freeze-dried and which may be dissolved in pyrogen free aqueous media or other appropriate parenteral injection fluid.

When the compositions are intended for inhalation they may be in the form of spray compositions for topical delivery to the lung by inhalation or in the form of dry powder compositions for topical delivery to the lung by inhalation.

The spray composition for inhalation may, for example, be formulated as aqueous solutions or suspensions or as aerosols delivered from pressurised packs, such as a metered dose inhaler, with the use of a suitable liquefied propellant.

Dry powder compositions for topical delivery to the lung by inhalation may, for example, be presented in different primary packaging systems (such as capsules and cartridges of for example gelatine or blisters of for example laminated aluminium foil), for use in an inhaler or insufflator. Packaging of the formulation may be suitable for unit dose or multi-dose delivery. In the case of multi-dose delivery, the formulation can be pre-metered or metered in use. Dry powder inhalers are thus classified into three groups: (a) single dose, (b) multiple unit dose and (c) multi dose devices.

Dry powder formulations generally contain a powder mix for inhalation of the compounds of the invention and a suitable powder base (carrier substance) such as lactose or starch. Use of lactose is preferred. Each capsule or cartridge may generally contain between 2 µg and 400 µg of each therapeutically active ingredient. Alternatively, the active ingredient (s) may be presented without excipients.

Effective doses are normally in the range of 2-2000 mg of active ingredient per day. Daily dosage may be administered in one or more treatments, preferably from 1 to 4 treatments, per day.

The syntheses of the compounds of the invention and of the intermediates for use therein are illustrated by the following Examples (1 to 36) including Preparation Examples (Intermediates 1 to 13) which do not limit the scope of the invention in any way.

$^1$H Nuclear Magnetic Resonance Spectra were recorded on a Varian Mercury spectrometer operating at 200 MHz. Melting points were recorded using a Buchi B-540 apparatus. The chromatographic separations were obtained using a Waters 2795 system equipped with a Symmetry C18 (2.1×100 mm, 3.5 mm) column. As detectors a Micromass ZMD mass spectrometer using ES ionization and a Waters 996 Diode Array detector were used. The mobile phase was formic acid (0.46 ml), ammonia (0.115 ml) and water (1000 ml) (A) and formic acid (0.4 ml), ammonia (0.1 ml), methanol (500 ml) and acetonitrile (500 ml) (B): initially from 0% to 95% of B in 20 min, and then 4 min. with 95% of B. The reequilibration time between two injections was 5 min. The flow rate was 0.4 ml/min. The injection volume was 5 µl. Diode array chromatograms were processed at 210 nm.

PREPARATION EXAMPLES

Intermediate 1

3"-Fluoro-3,2':3',4"-terpyridine-5',6'-diamine

Step a

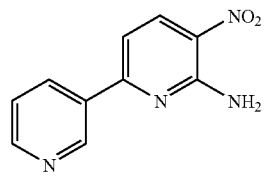

5-Nitro-2,3'-bipyridin-6-amine

An oven dried resealable Schlenk tube was charged with 6-chloro-3-nitropyridin-2-amine (5 g, 28.81 mmol), 3-pyridineboronic acid (5.31 g, 43.2 mmol), dioxane (250 mL) and a 2M aqueous solution of cesium carbonate (43 mL, 86.4 mmol). The Schlenk tube was subjected to three cycles of evacuation-backfilling with argon, and 1,1'-bis(diphenylphosphino)ferrocene-palladium(II) dichloride dichloromethane complex (2.3 g, 2.81 mmol) was added. After three new cycles of evacuation-backfilling with argon, the Schlenk tube was capped and placed in a 100° C. oil bath. After 3 h, the mixture was cooled, partitioned between water and ethyl acetate, the aqueous phase extracted twice with ethyl acetate, the organic layers washed with brine, dried (MgSO$_4$) and evaporated. The residue was purified by silica gel flash chromatography (95:5 dichloromethane/methanol) to give the title compound (4.8 g, 77%) as a solid.

δ $^1$H-NMR (CDCl$_3$): 1.64 (s, 2H), 7.20-7.25 (d, 1H), 7.44-7.46 (m, 1H), 8.32-8.36 (d, 1H), 8.52-8.56 (d, 1H), 8.70-8.74 (m, 1H), 9.22-9.26 (m, 1H).

ESI/MS m/e: 217 ([M+H]$^+$, C$_{10}$H$_8$N$_4$O$_2$)

Step b

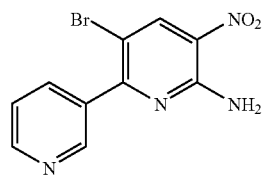

3-Bromo-5-nitro-2,3'-bipyridin-6-amine

To a 0° C. cooled stirred solution of 5-nitro-2,3'-bipyridin-6-amine (4.8 g, 22.2 mmol) in DMF (50 mL), N-bromosuccinimide (4.75 g, 26.7 mmol) was added in portions. After stirring at room temperature for 16 h, the solvent was removed under reduced pressure. The crude residue was solved with ethyl acetate and washed with saturated potassium carbonate aqueous solution. The organic layer was washed with brine, dried (MgSO₄) and evaporated. The residue was purified by silica gel flash chromatography (95:5 dichloromethane/methanol) to give the title compound (6.6 g, 100%) as a solid.

δ $^1$H-NMR (CDCl₃): 1.60 (s, 2H), 7.40-7.46 (dd, 1H), 8.03-8.09 (m, 1H), 8.67-8.77 (m, 2H), 8.93-9.02 (m, 1H).

ESI/MS m/e: 295, 297 ([M]⁺, [M+2]⁺, $C_{10}H_7BrN_4O_2$)

Step c

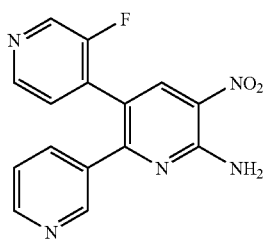

3''-Fluoro-5'-nitro-3,2':3',4''-terpyridin-6'-amine

An oven dried resealable Schlenk tube was charged with 3-bromo-5-nitro-2,3'-bipyridin-6-amine (4.51 g, 15.3 mmol), 3-fluoro-4-(tributylstannyl)pyridine (11.8 g, 30.6 mmol) and dimethylformamide (150 mL). The Schienk tube was subjected to three cycles of evacuation-backfilling with argon, and bis(triphenylphosphino)-palladium (II) chloride (1.1 g, 1.53 mmol) and copper (I) iodide (291 mg, 1.53 mmol) were added. After three new cycles of evacuation-backfilling with argon, the Schlenk tube was capped and placed in a 160° C. oil bath. After 3 h, the solvent was evaporated and the crude residue was treated with 2N hydrogen chloride (130 mL) aqueous solution for 45 minutes. The aqueous solution was washed with ethyl acetate and then neutralised with 6N sodium hydroxide aqueous solution. The solution was extracted with ethyl acetate, dried (MgSO₄) and evaporated. The residue was purified by silica gel flash chromatography (95:5 dichloromethane/methanol) to give the title compound (2.39 g, 51%) as a solid.

δ $^1$H-NMR (CDCl₃): 7.32-7.39 (m, 1H), 7.47-7.53 (dd, 1H), 7.66-7.72 (m, 1H), 8.43-8.45 (m, 2H), 8.48-8.50 (dd, 1H), 8.52-8.57 (m, 2H).

ESI/MS m/e: 312 ([M+H]⁺, $C_{15}H_{10}FN_5O_2$)

Step d

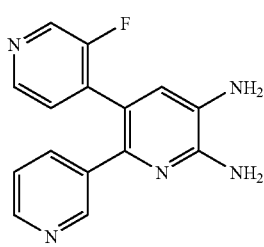

3''-Fluoro-3,2':3',4''-terpyridine-5',6'-diamine

A suspension of 3''-fluoro-5'-nitro-3,2':3',4''-terpyridin-6'-amine (2.25 g, 7.23 mmol) and 10% palladium on carbon (0.4 g) in a mixture of THF/ethanol 40:60 (100 mL) was stirred under hydrogen atmosphere. After 3 h, the mixture was filtered through Celite® and the filter cake was washed with ethanol. The combined filtrate and washings were evaporated to give the title compound as a solid (2.01 g, 99%).

δ $^1$H-NMR (CDCl₃): 5.10 (s, 2H), 5.95 (s, 2H), 6.75 (s, 1H), 7.18-7.30 (m, 2H), 7.49-7.55 (m, 1H), 8.29-8.31 (m, 1H), 8.32-8.34 (m, 1H), 8.35-8.38 (m, 1H), 8.40 (m, 1H).

ESI/MS m/e: 281 ([M+H]⁺, $C_{15}H_{12}FN_5$)

Intermediate 2

3,2':3',4''-Terpyridine-5',6'-diamine

Step a

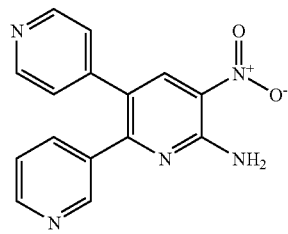

5'-Nitro-3,2':3',4''-terpyridin-6'-amine

Obtained (220 mg, 22%) from 3-bromo-5-nitro-2,3'-bipyridin-6-amine (Intermediate 1-Step b, 1.0 g, 3.4 mmol) and 4-(4,4,5,5-tetramethyl-1,3,2-dioxaborolan-2-yl)pyridine (764 mg, 3.73 mmol) following the same procedure described in Intermediate 1, step a.

δ $^1$H NMR (DMSO-d₆): 7.17 (d, 1H), 7.35 (dd, 1H), 7.68-7.40 (m, 3H), 7.82 (d, 1H), 8.22 (broad s, 1H), 8.50-8.40 (m, 2H), 8.53 (broad d, 1H), 8.69 (broad s, 1H).

ESI/MS m/e: 294 ([M+H]⁺, $C_{15}H_{11}N_5O_2$).

Step b

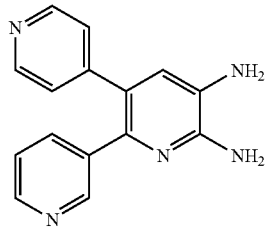

3,2':3',4''-Terpyridine-5',6'-diamine

Obtained (148 mg, 75%) from 5'-nitro-3,2':3',4''-terpyridin-6'-amine (220 mg, 0.75 mmol) following the same protocol described in Intermediate 1, step d.

ESI/MS m/e: 264 ([M+H]⁺, $C_{15}H_{13}N_5$).

Intermediate 3

3"-Chloro-3,2':3',4"-terpyridine-5',6'-diamine

Step a

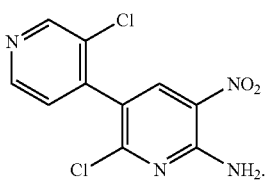

2,3'-Dichloro-5-nitro-3,4'-bipyridin-6-amine

Following the same procedure as in Intermediate 1 (step a), but using 4-(4,4,5,5-tetramethyl-1,3,2-dioxaborolan-2-yl)-3-chloropyridine, 6-chloro-5-iodo-3-nitropyridin-2-amine (Intermediate 5—step a) was transformed into the title compound as a white solid (205 mg, 22%).

δ $^1$H NMR (CDCl$_3$): 7.28 (d, 1H), 8.39 (s, 1H), 8.61 (d, 1H), 8.75 (s, 1H).

ESI/MS m/e: 286 ([M+H]$^+$, C$_{10}$H$_6$Cl$_2$N$_4$O$_2$).

Step b

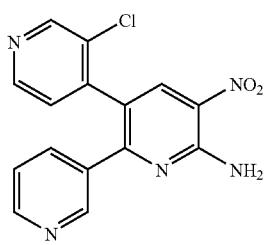

3"-Chloro-5'-nitro-3,2':3',4"-terpyridine-6'-amine

Following the same procedure as in Intermediate 1 (step a), 2,3'-dichloro-5-nitro-3,4'-bipyridin-6-amine afforded the title compound as a brownish solid (127 mg, 54%).

ESI/MS m/e: 328 ([M+H]$^+$, Cl$_5$H$_{10}$ClN$_5$O$_2$).

Step c

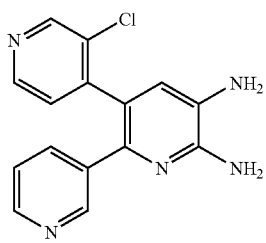

3"-Chloro-3,2':3',4"-terpyridine-5',6'-diamine

3"-chloro-5'-nitro-3,2':3',4"-terpyridin-6'-amine (127 mg, 0.39 mmol) was dissolved in EtOH (4.0 mL) and conc. HCl (245 μL). Iron metal (109 mg, 1.09 mmol) was added to the suspension and the mixture was heated to 70° C. for 1 h. The suspension was then filtered through Celite® and the solvent removed in vacuo. NaHCO$_3$ (20 mL of a 4% w/w aqueous solution) was added to the residue and the aqueous phase was extracted with AcOEt (3×20 mL). The organic layer was dried, filtered and concentrated to dryness to yield the title compound (52 mg, 45%), which was used without further purification.

ESI/MS m/e: 298 ([M+H]$^+$, C$_{15}$H$_{12}$ClN$_5$).

Intermediate 4

4,2':3',4"-Terpyridine-5',6'-diamine

Step a

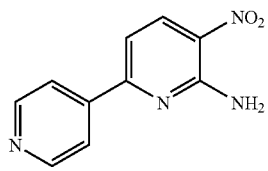

5-Nitro-2,4'-bipyridin-6-amine

Obtained (0.240 g, 96% of yield) from 6-chloro-3-nitropyridin-2-amine (0.2 g, 1.15 mmol) and 4-(4,4,5,5-tetramethyl-[1,3,2]dioxaborolan-2-yl)-pyridine (0.308 g, 1.50 mmol) following the procedure described in Intermediate 1, step a.

δ $^1$H-NMR (CDCl$_3$): 7.23-7.27 (d, 1H), 7.87-7.90 (m, 2H), 8.54-8.58 (d, 1H), 8.76-8.79 (m, 2H).

ESI/MS m/e: 217 ([M+H]$^+$, C$_{10}$H$_8$N$_4$O$_2$)

Step b

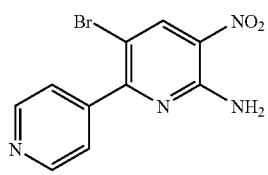

3-Bromo-5-nitro-2,4'-bipyridin-6-amine

Obtained (0.246 g, 76% of yield) from 5-nitro-2,4'-bipyridin-6-amine (0.240 g, 1.11 mmol) following the procedure described in Intermediate 1, step b.

ESI/MS m/e: 295, 297 ([M]$^+$, [M+2]$^+$, C$_{10}$H$_7$BrN$_4$O$_2$)

Step c

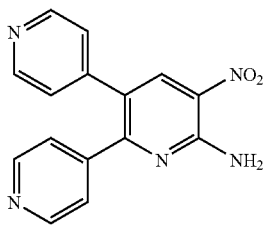

5'-Nitro-4,2':3',4''-terpyridin-6'-amine

Obtained (0.144 g, 60% of yield) from 3-bromo-5-nitro-2,4'-bipyridin-6-amine (0.240 g, 0.813 mmol) and 4-(4,4,5,5-tetramethyl-[1,3,2]dioxaborolan-2-yl)-pyridine (0.250 g, 1.220 mmol) following the procedure described in Intermediate 1, step c.
ESI/MS m/e: 294 ([M+H]$^+$, C$_{15}$H$_{11}$N$_5$O$_2$)

Step d

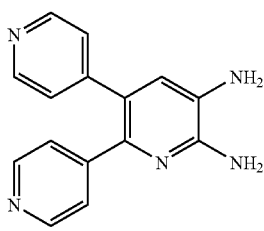

4,2':3',4''-Terpyridine-5',6'-diamine

To a solution of 5'-nitro-4,2':3',4''-terpyridin-6'-amine (0.144 g, 0.490 mmol) in ethanol (5 mL), 0.300 mL of hydrogen chloride and 0.140 g (2.45 mmol) of iron were added. The mixture was heated at 90° C. for 2 h and the solvent was evaporated. The crude mixture was extracted between ethyl acetate and water. The organic layer was dried (MgSO$_4$) and the solvent evaporated to give the title compound (0.120 g, 93% of yield).
ESI/MS m/e: 264 ([M+H]$^+$, C$_{15}$H$_{13}$N$_5$)

Intermediate 5

3-Fluoro-4,2':3',4''-terpyridine-5',6'-diamine

Step a

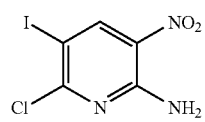

6-Chloro-5-iodo-3-nitropyridin-2-amine

To a suspension of 6-chloro-3-nitropyridin-2-amine (6.3 g, 36.3 mmol) in ethanol (110 mL), 9.2 g (36.3 mmol) of iodine and 11.32 g (36.3 mmol) of silver sulphate were added. The crude mixture was stirred at room temperature overnight and the precipitate formed was filtered off. The solid isolated was purified by flash chromatography (1:1 hexane/ethyl acetate) to give the title compound (9.74 g, 88% of yield).
δ $^1$H-NMR (CDCl$_3$): 1.56 (s, 2H), 8.76 (s, 1H).
ESI/MS m/e: 300 ([M+H]$^+$, C$_5$H$_3$ClIN$_3$O$_2$)

Step b

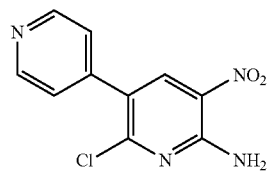

2-Chloro-5-nitro-3,4'-bipyridin-6-amine

Obtained (0.666 g, 80% of yield) from 6-chloro-5-iodo-3-nitropyridin-2-amine (1 g, 3.34 mmol) and 4-(4,4,5,5-tetramethyl-[1,3,2]dioxaborolan-2-yl)-pyridine (0.754 g, 3.67 mmol) following the procedure described in Intermediate 1, step a.
ESI/MS m/e: 251 ([M+H]$^+$, C$_{10}$H$_7$ClN$_4$O$_2$)

Step c

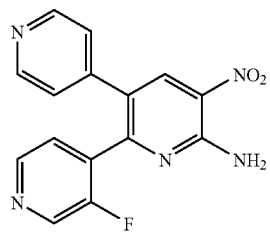

3-Fluoro-5'-nitro-4,2':3',4''-terpyridin-6'-amine

Obtained (0.214 g, 69% of yield) from 2-chloro-5-nitro-3,4'-bipyridin-6-amine (0.250 g, 1 mmol) and 3-fluoro-4-(4,4,5,5-tetramethyl-[1,3,2]dioxaborolan-2-yl)-pyridine (0.445 g, 2 mmol) following the procedure described in Intermediate 1, step a.
δ $^1$H-NMR (CDCl$_3$): 1.24 (s, 2H), 7.04-7.07 (m, 2H), 7.39-7.45 (m, 2H), 8.37 (s, 1H), 8.51-8.57 (m, 3H).
ESI/MS m/e: 312 ([M+H]$^+$, C$_{15}$H$_{10}$FN$_5$O$_2$)

Step d

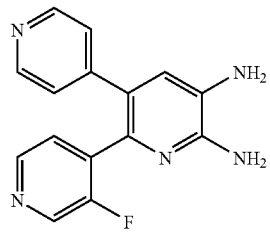

3-Fluoro-4,2':3',4''-terpyridine-5',6'-diamine

Obtained (0.183 g, 94% of yield) from 3-fluoro-5'-nitro-4,2':3',4''-terpyridin-6'-amine (0.215 g, 0.69 mmol) following the procedure described in Intermediate 1, step d.

δ $^1$H-NMR (CDCl$_3$): 1.26 (s, 4H), 7.00-7.05 (m, 3H), 7.37-7.43 (m, 1H), 8.27 (s, 1H), 8.40-8.48 (m, 3H).

ESI/MS m/e: 282 ([M+H]$^+$, C$_{15}$H$_{12}$FN$_5$)

Intermediate 6

3-Chloro-4,2':3',4''-terpyridine-5',6'-diamine

Step a

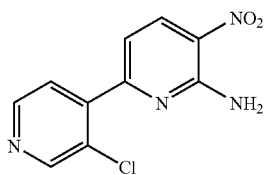

3'-Chloro-5-nitro-2,4'-bipyridin-6-amine

Following the same procedure as in Intermediate 1 (step a), but using 4-(4,4,5,5-tetramethyl-1,3,2-dioxaborolan-2-yl)-3-chloropyridine, 6-chloro-3-nitropyridin-2-amine was transformed into the title compound as a white solid (2.14 g, 99%).

δ $^1$H NMR (CDCl$_3$): 7.15 (d, 1H), 7.52 (d, 1H), 8.55 (d, 1H), 8.62 (d, 1H), 8.73 (s, 1H).

ESI/MS m/e: 251 ([M+H]$^+$, C$_{10}$H$_7$ClN$_4$O$_2$).

Step b

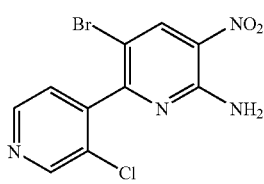

3-Bromo-3'-chloro-5-nitro-2,4'-bipyridin-6-amine

Following the same procedure as in Intermediate 1 (step b) 3'-chloro-5-nitro-2,4'-bipyridin-6-amine afforded the title compound as a brownish solid (2.04 g, 93%).

δ $^1$H NMR (CDCl$_3$): 7.25 (d, 1H), 8.64 (d, 1H), 8.73 (s, 1H), 8.74 (d, 1H).

ESI/MS m/e: 328, 330 ([M]$^+$, [M+2]$^+$, C$_{10}$H$_6$BrClN$_4$O$_2$).

Step c

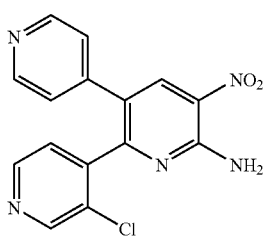

3-Chloro-5'-nitro-4,2':3',4''-terpyridin-6'-amine

Following the same procedure as in Intermediate 1 (step a), but using 4-(4,4,5,5-tetramethyl-1,3,2-dioxaborolan-2-yl)pyridine, 3-bromo-3'-chloro-5-nitro-2,4'-bipyridin-6-amine was converted to the title compound as yellowish solid (0.84 g, 85%).

δ $^1$H NMR (CDCl$_3$): 7.03 (broad d, 2H), 7.25 (d, 1H), 8.51 (broad d, 2H), 8.55 (d, 1H), 8.57 (s, 1H), 8.59 (s, 1H).

ESI/MS m/e: 328 ([M+H]$^+$, C$_{15}$H$_{10}$ClN$_5$O$_2$).

Step d

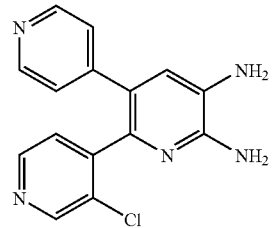

3-Chloro-4,2':3',4''-terpyridine-5',6'-diamine

Following the same procedure as in Intermediate 1 (step d), 3-chloro-5'-nitro-4,2':3',4''-terpyridin-6'-amine gave the title compound as white solid (0.78 g, >99%).

δ $^1$H NMR (DMSO): 5.14 (broad s, 2H), 5.94 (broad s, 2H), 6.83 (s, 1H), 6.95 (broad d, 2H), 7.32 (d, 1H), 8.33 (broad d, 2H), 8.42 (d, 1H), 8.46 (s, 1H).

ESI/MS m/e: 298 ([M+H]$^+$, C$_{15}$H$_{12}$ClN$_5$).

Intermediate 7

3''-Chloro-4,2':3',4''-terpyridine-5',6'-diamine

Step a

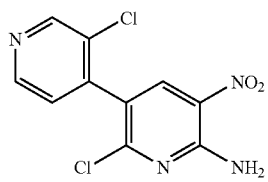

2,3'-Dichloro-5-nitro-3,4'-bipyridin-6-amine

Obtained (0.118 g, 41% of yield) from 6-chloro-5-iodo-3-nitropyridin-2-amine (0.3 g, 1 mmol) and 3-chloro-4-(4,4,5,5-tetramethyl-[1,3,2]dioxaborolan-2-yl)-pyridine (0.311 g, 1.3 mmol) following the procedure described in Intermediate 3, step a.

ESI/MS m/e: 285 ([M+H]$^+$, C$_{10}$H$_6$Cl$_2$N$_4$O$_2$)

Step b

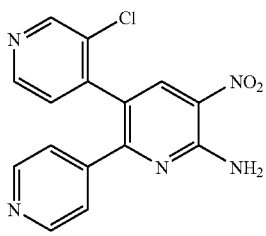

3''-Chloro-5'-nitro-4,2':3',4''-terpyridin-6'-amine

Obtained (0.130 g, 99% of yield) from 2,3'-dichloro-5-nitro-3,4'-bipyridin-6-amine (0.120 g, 0.42 mmol) and 4-(4,4,5,5-tetramethyl-[1,3,2]dioxaborolan-2-yl)-pyridine (0.130 g, 0.63 mmol) following the procedure described in Intermediate 1, step a.

δ $^1$H-NMR (CDCl$_3$): 1.24 (s, 2H), 7.12-7.23 (m, 3H), 7.40-7.64 (m, 1H), 8.48-8.57 (m, 2H), 8.61 (s, 1H).

ESI/MS m/e: 328 ([M+H]$^+$, C$_{15}$H$_{10}$ClN$_5$O$_2$)

Step c

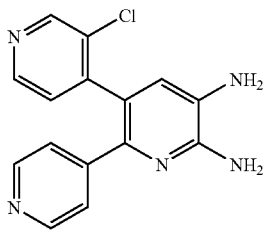

3''-Chloro-4,2':3',4''-terpyridine-5',6'-diamine

Obtained (0.082 g, 62% of yield) from 3''-chloro-5'-nitro-4,2':3',4''-terpyridin-6'-amine (0.145 g, 0.443 mmol) following the procedure described in Intermediate 4, step d.

ESI/MS m/e: 298 ([M+H]$^+$, C$_{15}$H$_{12}$ClN$_5$)

Intermediate 8

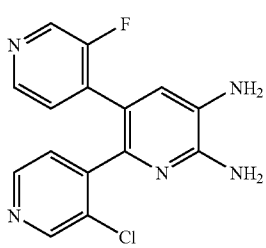

3-Chloro-3''-fluoro-4,2':3',4''-terpyridine-5',6'-diamine

Obtained as a white solid (24%) from 3-bromo-3'-chloro-5-nitro-2,4'-bipyridin-6-amine (Intermediate 6-step b) and 3-fluoro-4-(tributylstannyl)pyridine, following the same procedure as in Intermediate 1 (step c).

ESI/MS m/e: 316 ([M+H]$^+$, C$_{15}$H$_{11}$ClFN$_5$).

Intermediate 9

3,3''-Dichloro-4,2':3',4''-terpyridine-5',6'-diamine

Step a

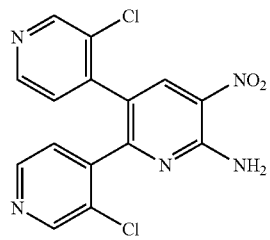

3,3''-Dichloro-5'-nitro-4,2':3',4''-terpyridin-6'-amine

Obtained (0.034 g, 10% of yield) from 6-chloro-5-iodo-3-nitropyridin-2-amine (0.3 g, 1 mmol) and 3-chloro-4-(4,4,5,5-tetramethyl-[1,3,2]dioxaborolan-2-yl)-pyridine (0.311 g, 1.3 mmol) following the procedure described in Intermediate 1, step a.

ESI/MS m/e: 362 ([M+H]$^+$, C$_{15}$H$_9$Cl$_2$N$_5$O$_2$)

Step b

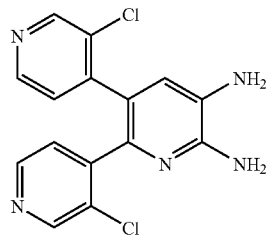

3,3''-Dichloro-4,2':3',4''-terpyridine-5',6'-diamine

Obtained (0.029 g, 72% of yield) from 3,3''-dichloro-5'-nitro-4,2':3',4''-terpyridin-6'-amine (0.045 g, 0.123 mmol) following the procedure described in Intermediate 4, step d.

ESI/MS m/e: 332 ([M+H]$^+$, C$_{15}$H$_{11}$Cl$_2$N$_5$)

Intermediate 10

2-(1,3-Oxazol-2-yl)-3,4'-bipyridine-5,6-diamine

Step a

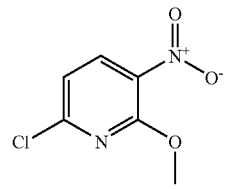

6-Chloro-2-methoxy-3-nitropyridine

Methanol (3.3 g, 103 mmol) in xylene (100 mL) was added dropwise to a stirred suspension of sodium hydride (60% in mineral oil, 2.72 g, 113 mmol) in xylene (300 mL) at 0° C. under an argon atmosphere. After 20 minutes, 2,6-dichloro-3-nitropyridine (20.0 g, 103 mmol) in xylene (300 mL) was added dropwise then the reaction was warmed to ambient temperature and stirred overnight. Water (200 mL) was then added and the two phases were separated. The organic layer was washed with water and brine, dried (MgSO$_4$) and evaporated. The residue was purified by flash chromatography (10:1 hexanes/ethyl acetate) to give the title compound (15.3 g, 78%) as a white solid.

δ $^1$H-NMR (CDCl$_3$): 4.10 (s, 3H), 7.05 (d, 1H), 8.28 (d, 1H).

Step b

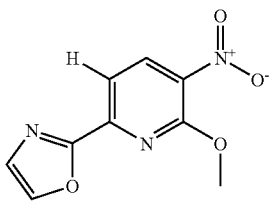

2-Methoxy-3-nitro-6-(1,3-oxazol-2-yl)pyridine

An oven-dried resealable Schlenk tube was charged with 6-chloro-2-methoxy-3-nitropyridine (0.50 g, 2.6 mmol), 2-tributylstannanyloxazole (1.20 g, 3.4 mmol) and 1,4-dioxane (10 mL) and then subjected to several cycles of evacuation-backfilling with argon. Tetrakis(triphenylphosphine)palladium (0.18 g, 0.16 mmol) was then added and, after three new cycles of evacuation-backfilling with argon, the Schlenk tube was sealed and the mixture was stirred and heated in an oil bath to 110° C. After stirring overnight, water and ethyl acetate were added and the organic layer was washed with water, dried (MgSO$_4$) and evaporated. The residue was purified by flash chromatography (2:1 hexanes/ethyl acetate) to give the title compound (0.38 g, 67%) as a yellow solid.

δ $^1$H-NMR (CDCl$_3$): 4.24 (s, 3H), 7.38 (s, 1H), 7.84 (d, 1H), 7.87 (s, 1H), 8.40 (d, 1H).

ESI/MS m/e: 222 ([M+H]+, C$_9$H$_7$N$_3$O$_4$)

Step c

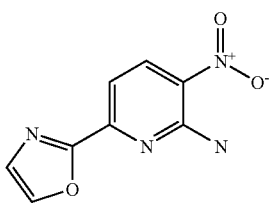

3-Nitro-6-(1,3-oxazol-2-yl)pyridin-2-amine

A suspension of 2-methoxy-3-nitro-6-(1,3-oxazol-2-yl)pyridine (0.187 g, 0.85 mmol) in aqueous ammonia (32%, 5 mL) was heated in a sealed tube to 100° C. with stirring. After 2.5 hours the mixture was cooled and the precipitate was filtered and washed with water and then dried in vacuo to give the title compound (0.134 g, 77%) as a yellow solid.

δ $^1$H-NMR (DMSO-d$_6$): 7.41 (d, 1H), 7.53 (s, 1H), 8.14 (s, 2H), 8.38 (s, 1H), 8.53 (d, 1H).

ESI/MS m/e: 207 ([M+H]+, C$_8$H$_6$N$_4$O$_3$)

Step d

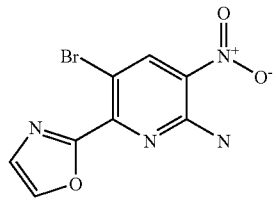

5-Bromo-3-nitro-6-(1,3-oxazol-2-yl)pyridin-2-amine

To a stirred solution of 3-nitro-6-(1,3-oxazol-2-yl)pyridin-2-amine (0.127 g, 0.62 mmol) in dimethylformamide (3 mL) at 0° C. was added N-bromosuccinimide (0.115 g, 0.65 mmol) and the mixture was warmed to room temperature. After 3 days, further N-bromosuccinimide (0.058 g, 0.33 mmol) was added and stirring was continued for 3 hours. The solution was poured into water and the precipitate was filtered, washed with water and dried to give the title compound (0.18 g, 70%) as a yellow solid.

δ $^1$H NMR (DMSO-d$_6$): 7.56 (s, 1H), 8.19 (s, 2H), 8.41 (s, 1H), 8.68 (s, 1H).

ESI/MS m/e: 285/287 ([M+H]+, C$_8$H$_5$BrN$_4$O$_3$)

Step e

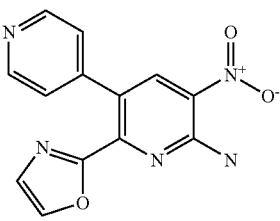

5-Nitro-2-(1,3-oxazol-2-yl)-3,4'-bipyridin-6-amine

An oven-dried resealable Schlenk tube was charged with 5-bromo-3-nitro-6-(1,3-oxazol-2-yl)pyridin-2-amine (0.141 g, 0.49 mmol), 4-(4,4,5,5-tetramethyl-1,3,2-dioxaborolan-2-yl)pyridine (0.203 g, 0.99 mmol), dioxane (5 mL) and a 2M aqueous solution of cesium carbonate (0.74 mL, 1.48 mmol). The Schlenk tube was subjected to three cycles of evacuation-backfilling with argon, and 1,1'-bis(diphenylphosphino)ferrocene-palladium(II) dichloride dichloromethane complex [PdCl$_2$dppf.DCM] (0.024 g, 0.03 mmol) was added. After three new cycles of evacuation-backfilling with argon, the Schlenk tube was sealed and the mixture was stirred and heated in an oil bath to 95° C. After 20 hours, the mixture was cooled and partitioned between 2M aqueous hydrochloric acid and ethyl acetate. The aqueous phase was filtered through Celite® and the pH was adjusted to 5-6 with solid sodium hydroxide. The suspension was cooled in an ice bath and the precipitate was filtered, washed with water and dried to give the title compound (0.090 g, 65%) as a yellow solid.

δ $^1$H-NMR (DMSO-d$_6$): 7.24 (d, 2H), 7.33 (s, 1H), 8.24 (s, 1H), 8.29 (s, 2H), 8.43 (s, 1H), 8.52 (d, 2H).

ESI/MS m/e: 284 ([M+H]+, C$_{13}$H$_9$N$_5$O$_3$)

Step f

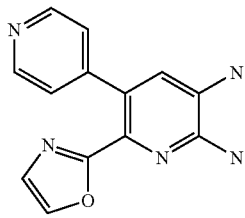

2-(1,3-Oxazol-2-yl)-3,4'-bipyridine-5,6-diamine

A suspension of 5-nitro-2-(1,3-oxazol-2-yl)-3,4'-bipyridin-6-amine (0.089 g, 0.31 mmol) and palladium on carbon (10%, 20 mg) in ethanol (15 mL) was placed under a hydrogen atmosphere (balloon) and stirred at room temperature. After 3 hours, the mixture was filtered through Celite® and the filtrate was evaporated. Trituration with diethyl ether gave the title compound (0.077 g, 97%) as a pale orange solid.

δ $^1$H-NMR (CDCl$_3$): 6.87 (s, 1H), 7.13 (m, 3H), 7.49 (s, 1H), 8.56 (d, 2H).

ESI/MS m/e: 254 ([M+H]+, C$_{13}$H$_{11}$N$_5$O)

Intermediate 11

3'-Fluoro-2-(1,3-oxazol-2-yl)-3,4'-bipyridine-5,6-diamine

Step a

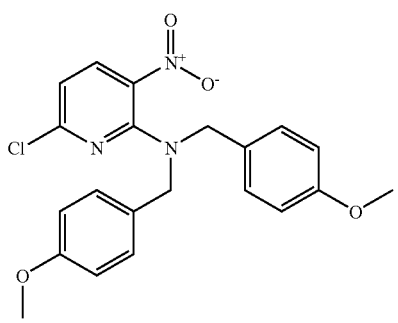

6-Chloro-N,N-bis(4-methoxybenzyl)-3-nitropyridin-2-amine

A solution of N,N-bis(4-methoxybenzyl)amine (7.79 g, 30.3 mmol) and triethylamine (2.89 g, 28.6 mmol) in chloroform (20 mL) was added dropwise over 20 minutes to a cold (ice-bath), stirred solution of 2,6-dichloro-3-nitropyridine (5.0 g, 26.0 mmol) in chloroform (25 mL). The mixture was warmed to room temperature and stirred overnight. The solvent was evaporated and the mixture was partitioned between ethyl acetate and water. The organic layer was washed with brine, dried (MgSO$_4$) and evaporated to give an oil. The mixture was taken up in dichloromethane (120 mL) and polymer-supported isocyanate resin (1.6 mmol/g, 8.0 g) was added and the mixture was shaken at room temperature for 2 days. The mixture was filtered and the filtrate was evaporated to give the title compound (10.7 g, 100%) as a bright yellow oil.

δ $^1$H-NMR (CDCl$_3$): 3.78 (s, 6H), 4.51 (s, 4H), 6.68 (d, 2H), 6.80 (d, 4H), 8.23 (d, 4H), 8.02 (d, 1H).

ESI/MS m/e: 414 ([M+H]+, C$_{21}$H$_{20}$ClN$_3$O$_4$)

Step b

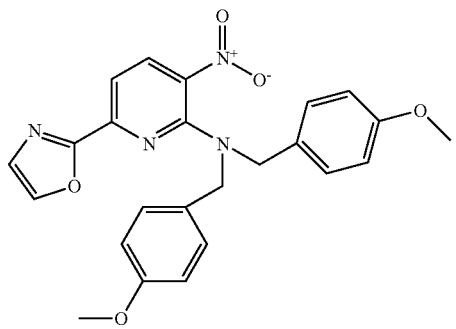

2-N,N-bis(4-methoxybenzyl)-3-nitro-6-(1,3-oxazol-2-yl)pyridine

Obtained (79%) from 6-chloro-N,N-bis(4-methoxybenzyl)-3-nitropyridin-2-amine and 2-tributylstannanyloxazole, following the procedure described in Preparation 10, step b.

δ $^1$H-NMR (CDCl$_3$): 3.79 (s, 6H), 4.60 (s, 4H), 6.80 (d, 4H), 7.10 (d, 4H), 7.34 (d, 1H), 7.55 (d, 1H), 7.82 (s, 1H), 8.20 (d, 1H).

ESI/MS m/e: 447 ([M+H]+, C$_{24}$H$_{22}$N$_4$O$_5$)

Step c

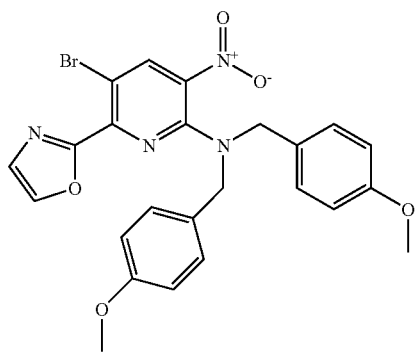

4-Bromo-2-N,N-bis(4-methoxybenzyl)-3-nitro-6-(1,3-oxazol-2-yl)pyridine

Obtained (52%) from 2-N,N-bis(4-methoxybenzyl)-3-nitro-6-(1,3-oxazol-2-yl)pyridine and N-bromosuccinimide, following the procedure described in Preparation 10, step d.

δ $^1$H-NMR (DMSO-d$_6$): 3.69 (s, 6H), 4.59 (s, 4H), 6.83 (d, 4H), 7.12 (d, 4H), 7.58 (s, 1H), 8.42 (s, 1H), 8.51 (s, 1H).
ESI/MS m/e: 525/527 ([M+H]+, C$_{24}$H$_{21}$BrN$_4$O$_5$)

Step d

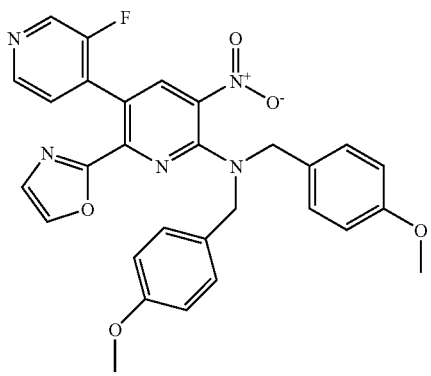

2-N,N-bis(4-methoxybenzyl)-4-(3-fluoropyridin-4-yl)-3-nitro-6-(1,3-oxazol-2-yl)pyridine An oven-dried resealable Schlenk tube was charged with 4-Bromo-2-N,N-bis(4-methoxybenzyl)-3-nitro-6-(1,3-oxazol-2-yl)pyridine (5.47 g, 10.4 mmol), 3-fluoro-4-(tributylstannyl)pyridine (5.22 g, 13.5 mmol) and dimethylformamide (82 mL). The Schienk tube was subjected to three cycles of evacuation-backfilling with argon, and bis(triphenylphosphino)-palladium (II) chloride (0.365 g, 0.52 mmol) and copper (I) iodide (0.198 g, 1.04 mmol) were added. After three new cycles of evacuation-backfilling with argon, the Schlenk tube was sealed and the mixture was stirred and heated to 160° C. in an oil bath. After 20 hours, the mixture was cooled and the solvent evaporated. The residue was taken up in a mixture of methanol and ethyl acetate, filtered through a plug of Celite® and evaporated. Purification by flash chromatography (6:1 hexanes/ethyl acetate to hexanes/ethyl acetate) provided the title compound (4.07 g, 72%) as a solid.
ESI/MS m/e: 542 ([M+H]+, C$_{29}$H$_{24}$FN$_5$O$_5$)

Step e

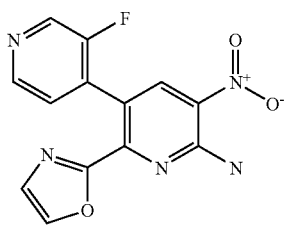

3'-Fluoro-5-nitro-2-(1,3-oxazol-2-yl)-3,4'-bipyridin-6-amine

A solution of 2-N,N-bis(4-methoxybenzyl)-4-(3-fluoropyridin-4-yl)-3-nitro-6-(1,3-oxazol-2-yl)pyridine (0.15 g, 0.37 mmol) in dichloromethane (2 mL) and trifluoroacetic acid (2 mL) was stirred at ambient temperature overnight. The solvent was evaporated and then the mixture was neutralized with 4% aqueous sodium hydrogen carbonate solution. The solid that formed was extracted with ethyl acetate and the organic layer was washed with water, brine, dried (MgSO$_4$) and evaporated to give the title compound (0.11 g, 67%) as a yellow solid.
δ $^1$H-NMR (CDCl$_3$): 7.21 (s, 1H), 7.30 (m, 1H), 7.71 (s, 1H), 8.51 (m, 3H).
ESI/MS m/e: 302 ([M+H]+, C$_{13}$H$_8$FN$_5$O$_3$)

Step f

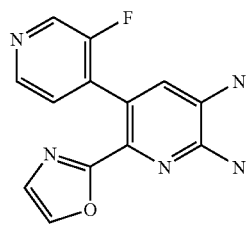

3'-Fluoro-2-(1,3-oxazol-2-yl)-3,4'-bipyridine-5,6-diamine

Obtained (93%) from 3'-fluoro-5-nitro-2-(1,3-oxazol-2-yl)-3,4'-bipyridin-6-amine by hydrogenation over palladium on carbon following the procedure described in Preparation 10, step f.
δ $^1$H-NMR (DMSO-d$_6$): 5.42 (s, 2H), 6.07 (s, 2H), 6.65 (s, 1H), 7.05 (s, 2H), 7.30 (m, 1H), 7.96 (s, 1H), 8.39 (m, 2H).
ESI/MS m/e: 272 ([M+H]+, C$_{13}$H$_{10}$FN$_5$O)

Intermediate 12

2-(1,3-Oxazol-5-yl)-3,4'-bipyridine-5,6-diamine

Step a

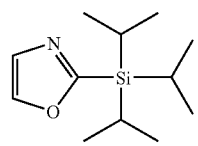

2-Triisopropylsilyloxazole n-BuLi (1.6M in hexanes, 76 mL, 190 mmol) was added dropwise over 30 minutes to a stirred solution of oxazole (12.0 g, 174 mmol) in diethyl ether (400 mL) at −78° C. under argon. The solution was allowed to stir for 60 minutes at −78° C. and then triisopropylsilyl triflate (46.3 mL, 172 mmol) was added dropwise over 30 minutes. The reaction mixture was slowly warmed up to room temperature and stirred overnight. The mixture was concentrated in vacuo and the residue was taken up in hexanes and filtered through a pad of silica gel eluting with 8:1 hexanes/ethyl acetate. Concentration gave the title compound (36.0 g, 93%) as a colourless oil.
δ $^1$H-NMR (CDCl$_3$): 1.12 (d, 18H), 1.37 (m, 3H), 7.20 (m, 1H), 7.81 (d, 1H).

Step b

5-Tributylstannanyl-2-triisopropylsilanyl-oxazole

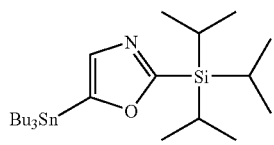

tert-BuLi (1.7M in n-pentane, 8.4 mL, 14.3 mmol) was added dropwise over (approximately) 30 minutes to a stirred solution of 2-triisopropylsilyloxazole (3 g, 13 mmol) in tetrahydrofuran (75 mL) at −78° C. under argon. The solution was allowed to stir for 20 minutes at −78° C. and tributyltin chloride (5.2 mL, 19.5 mmol) was then added over 20 minutes. The reaction mixture was warmed to room temperature and stirred for an additional 16 hours. The reaction was diluted with ethyl acetate, washed with water and the organic layer was dried (MgSO$_4$) and concentrated under reduced pressure. The crude product was dissolved in n-pentane, filtered through Celite® and the solvent evaporated to give the title compound in quantitative yield as a pale-yellow oily residue, which was used without further purification in the next step.

δ $^1$H-NMR (CDCl$_3$): 1.12 (d, 18H), 1.38 (m, 3H), 1.42 (d, 9H), 1.52-1.95 (m, 18H) 7.22 (s, 1H).

Step c

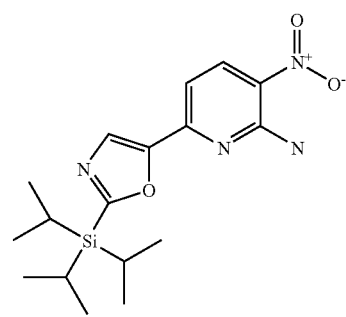

3-Nitro-6-(2-triisopropylsilanyl-1,3-oxazol-5-yl)pyridin-2-amine

Obtained (80%) from 6-bromo-3-nitropyridin-2-amine and 5-tributylstannanyl-2-triisopropylsilanyloxazole, following the procedure described in Preparation 10, step b.

δ $^1$H-NMR (CDCl$_3$): 1.17 (d, 18H), 1.43 (m, 3H), 7.11 (d, 1H), 7.85 (s, 1H), 8.48 (d, 1H).

ESI/MS m/e: 363 ([M+H]+, $C_{17}H_{26}N_4O_3Si$)

Step c

Alternative Method

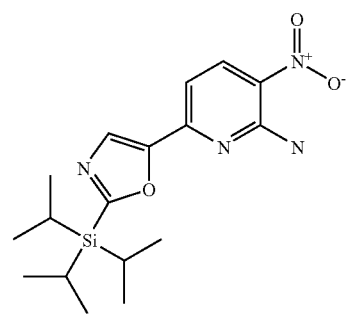

3-Nitro-6-(2-triisopropylsilanyl-1,3-oxazol-5-yl)pyridin-2-amine

Obtained (67%) from 6-chloro-3-nitropyridin-2-amine and 5-tributylstannanyl-2-triisopropylsilanyloxazole, following the procedure described in Preparation 10, step b.

Step d

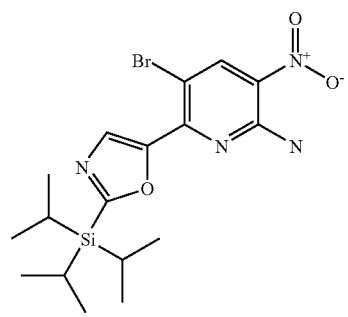

5-Bromo-3-nitro-6-(2-triisopropylsilanyl-1,3-oxazol-5-yl)pyridin-2-amine

Obtained (88%) from 3-nitro-6-(2-triisopropylsilanyl-1,3-oxazol-5-yl)pyridin-2-amine and N-bromosuccinimide, following the procedure described in Preparation 10, step d.

δ $^1$H-NMR (CDCl$_3$): 1.17 (d, 18H), 1.45 (m, 3H), 8.15 (s, 1H), 8.68 (s, 1H).

ESI/MS m/e: 441/443 ([M+H]+, $C_{17}H_{26}BrN_4O_3Si$)

Step e

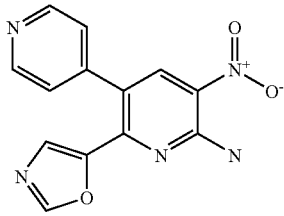

5-Nitro-2-(1,3-oxazol-5-yl)-3,4'-bipyridin-6-amine

Obtained (74%) from 5-bromo-3-nitro-6-(2-triisopropylsilanyl-1,3-oxazol-5-yl)pyridin-2-amine and 4-(4,4,5,5-tetramethyl-1,3,2-dioxaborolan-2-yl)pyridine following the procedure described in Preparation 10, step e.

δ $^1$H-NMR (CDCl$_3$): 7.15 (s, 1H), 7.38 (d, 2H), 8.20 (s, 1H), 8.32 (s, 1H), 8.45 (s, 1H), 8.62 (d, 2H).

ESI/MS m/e: 284 ([M+H]+, $C_{13}H_9N_5O_3$)

Step f

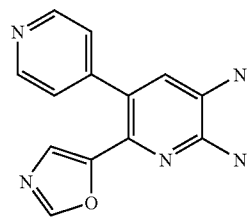

2-(1,3-Oxazol-5-yl)-3,4'-bipyridine-5,6-diamine

Obtained (82%) from 5-nitro-2-(1,3-oxazol-5-yl)-3,4'-bipyridin-6-amine by hydrogenation over palladium on carbon following the procedure described in Preparation 10, step f.

δ $^1$H-NMR (DMSO-d$_6$): 5.26 (s, 2H), 5.94 (s, 2H), 6.67 (s, 1H), 6.79 (s, 1H), 7.16 (d, 2H), 8.12 (s, 1H), 8.52 (m, 2H).

ESI/MS m/e: 254 ([M+H]+, C$_{13}$H$_{11}$N$_5$O)

Intermediate 13

3'-Fluoro-2-(1,3-oxazol-5-yl)-3,4'-bipyridine-5,6-diamine

Step a

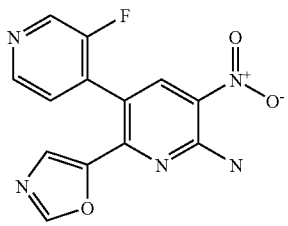

3'-Fluoro-5-nitro-2-(1,3-oxazol-5-yl)-3,4'-bipyridin-6-amine

Obtained (18%) from 5-bromo-3-nitro-6-(2-triisopropyl-silanyl-1,3-oxazol-5-yl)pyridin-2-amine and 3-fluoro-4-(tributylstannyl)pyridine following the procedure described in Preparation 11, step d.

δ $^1$H-NMR (CDCl$_3$): 7.30 (m, 1H), 7.38 (s, 1H), 7.81 (s, 1H), 8.40 (s, 1H), 8.52 (m, 2H).

ESI/MS m/e: 302 ([M+H]+, C$_{13}$H$_8$FN$_5$O$_3$)

Step b

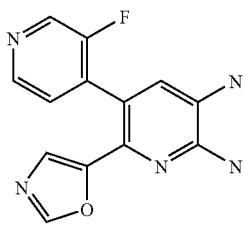

3'-Fluoro-2-(1,3-oxazol-5-yl)-3,4'-bipyridine-5,6-diamine

Obtained (89%) from 3'-fluoro-5-nitro-2-(1,3-oxazol-5-yl)-3,4'-bipyridin-6-amine by hydrogenation over palladium on carbon following the procedure described in Preparation 10, step f.

ESI/MS m/e: 272 ([M+H]+, C$_{13}$H$_{10}$FN$_5$O)

Intermediate 14

Step a

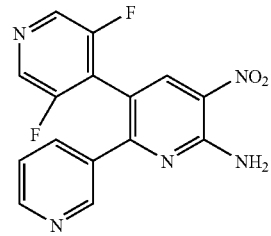

3",5"-difluoro-5'-nitro-3,2':3',4"-terpyridin-6'-amine

A mixture of 3-bromo-5-nitro-2,3'-bipyridin-6-amine (Intermediate 1, step b, 1 g, 3.39 mmol), 3,5-difluoro-4-tributyl-stannanylpyridine (1.5 g, 3.71 mmol), bis(triphenylphosphino)palladium (II) chloride (0.24 g, 0.34 mmol) and copper (I) iodide (0.13 g, 0.68 mmol) in dioxane (15 mL) was heated at 150° C. for 6 hours in Biotage Initiator Microwave Synthesizer.

The mixture was filtered through Celite® and the filter cake was washed with dioxane. The solvent was evaporated and the crude residue was purified by silica gel flash chromatography (95:5 dichloromethane/methanol) to give the title compound (1.07 g, 95%) as a yellow solid.

ESI/MS m/e: 330 ([M+H]$^+$, C$_{15}$H$_9$F$_2$N$_5$O$_2$).

Step b

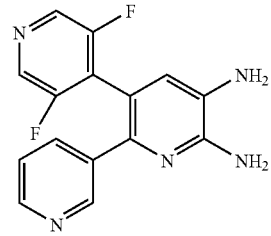

3",5"-difluoro-3,2':3',4"-terpyridine-5',6'-diamine

A suspension of 3",5"-difluoro-5'-nitro-3,2':3',4"-terpyridin-6'-amine (0.2 g, 0.608 mmol) and 10% palladium on carbon (0.04 g) in a mixture of THF/ethanol 40:60 (8 mL) was stirred under hydrogen atmosphere at 2.76 bar. After 12 h, the mixture was filtered through Celite® and the filter cake was washed with ethanol and THF. The combined filtrate and washings were evaporated to give the title compound as a solid (0.180 g, 99%).

ESI/MS m/e: 300 ([M+H]$^+$, C$_{15}$H$_{11}$F$_2$N$_5$).

EXAMPLES

Example 1

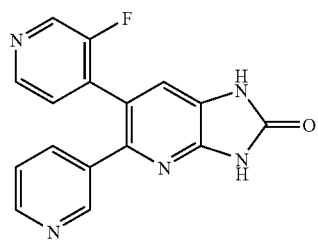

6-(3-Fluoropyridin-4-yl)-5-pyridin-3-yl-1,3-dihydro-2H-imidazo[4,5-b]pyridin-2-one To a solution of 3''-fluoro-3,2':3',4''-terpyridine-5',6'-diamine (Intermediate 1, 158 mg, 0.56 mmol) in THF (5 mL) Et$_3$N (156 µL, 1.12 mmol) and carbonyldiimidazole (182 mg, 1.12 mmol) were added sequentially. The reaction mixture was heated to reflux for 4 h and then the solvent was removed under reduced pressure. Flash chromatography of the resulting crude oil (CH$_2$Cl$_2$/EtOH/aq NH$_3$ 60:8:1 to 40:8:1) followed by reverse phase chromatography (0% CH$_3$CN in H$_2$O to 25% CH$_3$CN in H$_2$O) gave the title compound as a white solid (29 mg, 17%).

δ $^1$H-NMR (DMSO-d$_6$): 7.27 (dd, 1H), 7.33 (s, 1H), 7.44 (dd, 1H), 7.59 (dt, 1H), 8.37 (d, 1H), 8.42 (m, 3H), 11.18 (s, 1H), 11.70 (s, 1H),

ESI/MS m/e: 308 ([M+H]$^+$, C$_{16}$H$_{10}$FN$_5$O).

Example 2

Step a

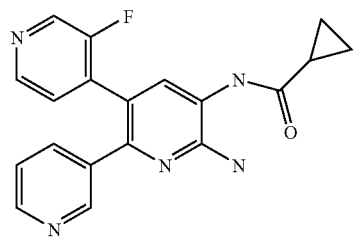

N-(6'-amino-3''-fluoro-3,2':3',4''-terpyridin-5'-yl)cyclopropanecarboxamide

To a solution of 3''-fluoro-3,2':3',4''-terpyridine-5',6'-diamine (Intermediate 1, 0.2 g, 0.71 mmol) in pyridine (2 mL), 0.071 mL (0.78 mmol) of cyclopropanoylcarbonyl chloride were added. The mixture was heated at 80° C. for 4 h and the solvent was evaporated. The crude mixture was extracted between ethyl acetate and water, the organic layer was dried (MgSO$_4$) and evaporated. The residue was purified by silica gel flash chromatography (90:10 dichloromethane/methanol) to give the title compound (0.202 g, 82% of yield).

ESI/MS m/e: 350 ([M+H]$^+$, C$_{19}$H$_{16}$FN$_5$O)

Step b

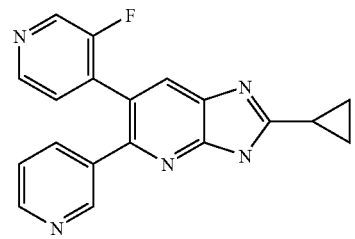

2-Cyclopropyl-6-(3-fluoropyridin-4-yl)-5-pyridin-3-yl-3H-imidazo[4,5-b]pyridine A solution of N-(6'-amino-3''-fluoro-3,2':3',4''-terpyridin-5'-yl)cyclopropanecarboxamide (0.2 g, 0.58 mmol) in acetic acid (2.5 mL) was heated in a sealed tube at 130° C. for 16 h. The solvent was evaporated and water (1 mL) was added and the solution was neutralised with 4% sodium bicarbonate aqueous solution and extracted with ethyl acetate. The organic layer was washed with brine, dried (MgSO$_4$) and evaporated. The residue was purified by silica gel flash chromatography (100:8:1 dichloromethane/methanol/NH$_3$) to give the title compound (0.024 g, 12% of yield).

ESI/MS m/e: 332 ([M+H]$^+$, C$_{19}$H$_{14}$FN$_5$)

Example 3 and Example 4

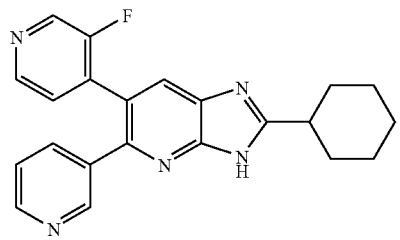

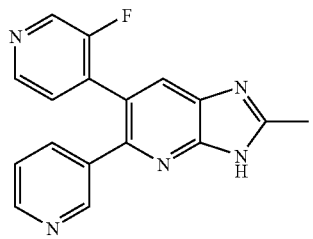

2-Cyclohexyl-6-(3-fluoropyridin-4-yl)-5-pyridin-3-yl-3H-imidazo[4,5-b]pyridine and 6-(3-fluoropyridin-4-yl)-2-methyl-5-pyridin-3-yl-3H-imidazo[4,5-b]pyridine The same procedure as in Example 2, but using cyclohexanecarbonyl chloride was followed. Final purification of the residue by flash chromatography (CH$_2$Cl$_2$,$_1$PrOH 98:2 to 65:35) afforded 2-cyclohexyl-6-(3-fluoropyridin-4-yl)-5-pyridin-3-yl-3H-imidazo[4,5-b]pyridine (Example 3) as a yellowish solid (134 mg, 51%): δ $^1$H-NMR (CDCl$_3$): 1.28-1.66 (m, 4H), 1.71-1.98 (m, 4H), 2.15 (broad d, 2H), 7.36 (ddd, 1H), 7.52 (dd, 1H), 7.82 (dt, 1H), 8.01 (s, 1H), 8.36 (d, 1H), 8.42 (dd, 1H), 8.46 (dd, 1H), 8.51 (broad d, 1H), ESI/MS m/e: 374 ([M+H]$^+$, C$_{22}$H$_{20}$FN$_5$), and 6-(3-fluoropyridin-4-yl)-2-methyl-5-pyridin-3-yl-3H-imidazo[4,5-b]pyridine (Example 4) as a white solid (90 mg, 42%) δ $^1$H-NMR (CDCl$_3$): 2.69 (s, 3H), 7.36 (ddd, 1H), 7.52 (dd, 1H), 7.82 (dt, 1H), 8.02 (s, 1H), 8.36 (d, 1H), 8.41 (dd, 1H), 8.46 (dd, 1H), 8.50 (broad d, 1H). ESI/MS m/e: 306 ([M+H]$^+$, C$_{17}$H$_{12}$FN$_5$).

Example 5

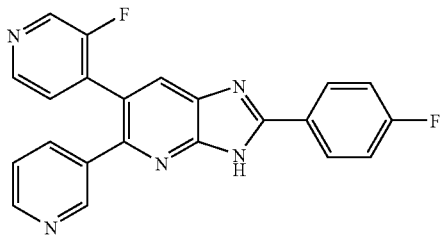

2-(4-Fluorophenyl)-6-(3-fluoropyridin-4-yl)-5-pyridin-3-yl-3H-imidazo[4,5-b]pyridine 3"-Fluoro-3,2':3',4"-terpyridine-5',6'-diamine (Intermediate 1,158 mg, 0.56 mmol), 4-fluorobenzoyl chloride (73.0 μL, 0.62 mmol) and pyridine (ca. 4 mL) were placed in a sealed tube. The solution was initially heated at 140° C. for 48 h and afterwards, at 160° C. for another 48 h. Then, the reaction mixture was cooled to room temperature, the pyridine was removed in vacuo, and the crude oil was purified by flash column chromatography (CH$_2$Cl$_2$/EtOH, 95:5) affording the title compound as a white solid (141 mg, 65%).

δ $^1$H-NMR (DMSO-d$_6$): 6.89 (t, 1H), 7.06 (t, 2H), 7.26 (dd, 1H), 7.56 (dt, 1H), 7.77 (dd, 1H), 7.82 (s, 1H), 7.96 (dd, 2H), 8.14 (dd, 1H), 8.18 (broad d, 1H), 8.25 (broad s, 1H).

ESI/MS m/e: 386 ([M+H]$^+$, C$_{22}$H$_{13}$F$_2$N$_5$).

Example 6

Step a

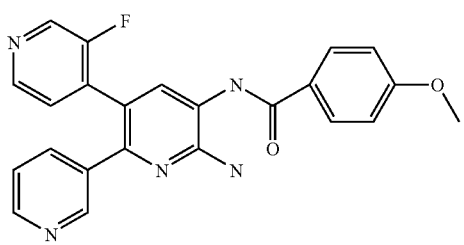

N-(6'-Amino-3"-fluoro-3,2':3',4"-terpyridine-5'-yl)-4-methoxybenzamide

To a solution of 3"-fluoro-3,2':3',4"-terpyridine-5',6'-diamine (Intermediate 1, 0.1 g, 0.36 mmol) in pyridine (2 mL), 4-methoxybenzoyl chloride (0.066 g, 0.39 mmol) was added. The mixture was stirred at room temperature overnight and the solvent was evaporated. Dichloromethane (1.6 mL) and tris-(2-aminoethyl)amine polystyrene (0.180 g, 0.72 mmol) were added and the mixture was stirred at room temperature for 1 h. The resin was filtrated and washed twice with dichloromethane. The filtrates were combined and the solvent was evaporated to give the title compound (0.172 g) which was used in the next step without further purification.

ESI/MS m/e: 416 ([M+H]$^+$, C$_{23}$H$_{18}$FN$_5$O$_2$)

Step b

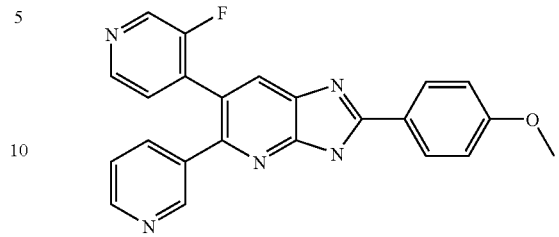

6-(3-Fluoropyridin-4-yl)-2-(4-methoxyphenyl)-6-pyridin-3-yl-3H-imidazo[4,5-b]pyridine Obtained (0.039 g, 28% of yield) from N-(6'-amino-3"-fluoro-3,2':3',4"-terpyridine-5'-yl)-4-methoxybenzamide following the procedure described in Example 2, step b.

δ $^1$H-NMR (CDCl$_3$): 3.93 (s, 3H), 7.09-7.14 (d, 2H), 7.08-7.36 (m, 4H), 7.48-7.52 (s, 1H), 8.09 (s, 1H), 8.21-8.25 (d, 2H), 8.42-8.48 (m, 1H), 8.54-8.62 (m, 1H), 9.42-9.46 (m, 1H).

ESI/MS m/e: 398 ([M+H]$^+$, C$_{23}$H$_{16}$FN$_5$O)

Example 7

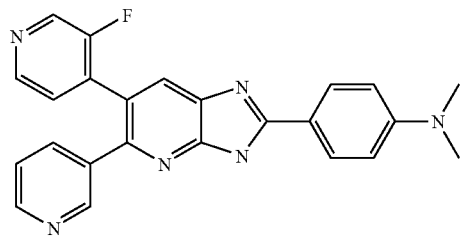

N-{4-[6-(3-Fluoropyridin-4-yl)-5-pyridin-3-yl-3H-imidazo[4,5-b]pyridin-2-yl]phenyl}-N,N-dimethylamine Obtained (0.020 g, 14% of yield) from 3"-fluoro-3,2':3',4"-terpyridine-5',6'-diamine (Intermediate 1, 0.1 g, 0.356 mmol) and 4-(dimethylamino)benzoyl chloride (0.072 g, 0.391 mmol) following the procedure described in Example 6.

δ $^1$H-NMR (CDCl$_3$): 3.10 (s, 6H), 6.81-6.85 (d, 2H), 7.21-7.30 (m, 4H), 7.62-7.66 (m, 1H), 7.99 (s, 1H), 8.04-8.09 (d, 2H), 8.37-8.42 (m, 1H), 8.53-8.55 (m, 1H), 8.65-8.70 (m, 1H).

ESI/MS m/e: 411 ([M+H]$^+$, C$_{24}$H$_{19}$FN$_6$)

Example 8

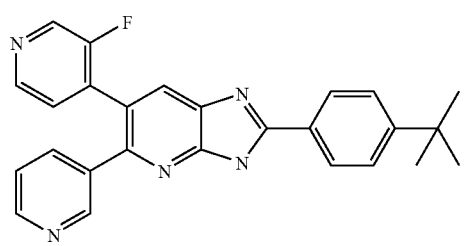

6-(3-Fluoropyridin-4-yl)-2-(4-tert-butylphenyl)-5-pyridin-3-yl-3H-imidazo[4,5-b]pyridine Obtained (0.050 g, 33% of yield) from 3"-fluoro-3,2':3',4"-terpyridine-5',6'-diamine (Intermediate 1, 0.1 g, 0.356 mmol) and 4-tert-butylbenzoyl chloride (0.072 mL, 0.391 mmol) following the procedure described in Example 6.

δ $^1$H-NMR (CDCl$_3$): 1.41 (s, 9H), 7.16-7.37 (m, 2H), 7.46-7.50 (m, 2H), 7.61-7.65 (d, 2H), 8.15 (s, 1H), 8.24-8.28 (d, 2H), 8.43-8.49 (m, 2H), 8.66-8.68 (m, 1H), 9.54 (bs, 1H).

ESI/MS m/e: 424 ([M+H]$^+$, C$_{26}$H$_{22}$FN$_5$)

Example 9

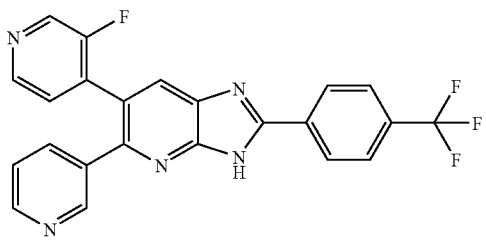

6-(3-Fluoropyridin-4-yl)-5-pyridin-3-yl-2-[4-(trifluoromethyl)phenyl]-3H-imidazo[4,5-b]pyridine Following the same procedure as in Example 2, but using 4-(trifluoromethyl)benzoyl chloride, the title compound was obtained as a white solid (172 mg, 57%).

δ $^1$H-NMR (CDCl$_3$): 7.21 (dd, 1H), 7.39 (t, 1H), 7.46 (broad d, 1H), 7.89 (d, 2H), 8.19 (s, 1H), 8.47 (d, 2H), 8.52 (broad s, 2H), 8.67 (broad d, 1H), 8.68 (s, 1H), 9.80 (broad s, 1H).

ESI/MS m/e: 436 ([M+H]$^+$, C$_{23}$H$_{13}$F$_4$N$_5$).

Example 10

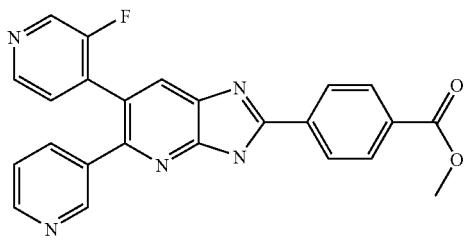

Methyl 4-[6-(3-fluoropyridin-4-yl)-5-pyridin-3-yl-3H-imidazo[4,5-b]pyridin-2-yl]benzoate Obtained (0.047 g, 31% of yield) from 3"-fluoro-3,2':3',4"-terpyridine-5',6'-diamine (Intermediate 1, 0.1 g, 0.356 mmol) and methyl 4-(chlorocarbonyl)benzoate (0.078 g, 0.391 mmol) following the procedure described in Example 6.

δ $^1$H-NMR (DMSO-d$_6$): 3.90 (s, 3H), 7.30-7.37 (m, 2H), 7.55-7.60 (m, 2H), 7.68-7.74 (m, 2H), 8.14-8.24 (m, 3H), 8.40-8.51 (m, 4H).

ESI/MS m/e: 426 ([M+H]$^+$, C$_{24}$H$_{16}$FN$_5$O$_2$)

Example 11

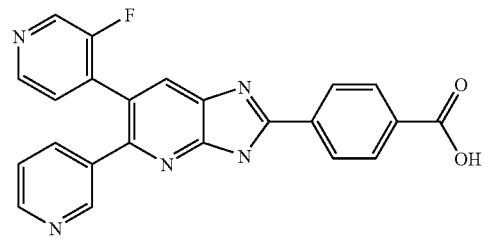

4-[6-(3-Fluoropyridin-4-yl)-5-pyridin-3-yl-3H-imidazo[4,5-b]pyridin-2-yl]benzoic acid To a solution of methyl 4-[6-(3-fluoropyridin-4-yl)-5-pyridin-3-yl-3H-imidazo[4,5-b]pyridin-2-yl]benzoate (Example 10, 0.041 g, 0.097 mmol) in a mixture of THF/ethanol 1:1 (1.2 mL), 2N sodium hydroxide aqueous solution (0.1 mL) was added. The mixture was heated at 60° C. for 3 h and then neutralised with 2N hydrogen chloride aqueous solution. The solvent was evaporated and the crude mixture was purified by silica gel flash chromatography (78:10:10:2 dichloromethane/ethanol/ethyl acetate/acetic acid) to give the title compound (0.013 g, 31% of yield).

δ $^1$H-NMR (DMSO-d$_6$): 7.31-7.37 (m, 2H), 7.55-7.60 (m, 2H), 7.68-7.74 (m, 2H), 8.09-8.13 (m, 1H), 8.21 (s, 1H), 8.30-8.35 (d, 2H), 8.47-8.51 (m, 3H).

ESI/MS m/e: 412 ([M+H]$^+$, C$_{23}$H$_{14}$FN$_5$O$_2$)

Example 12

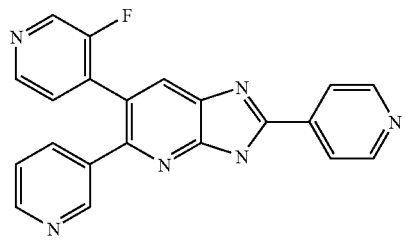

6-(3-Fluoropyridin-4-yl)-5-pyridin-3-yl-2-pyridin-4-yl-3H-imidazo[4,5-b]pyridine Obtained (0.070 g, 53% of yield) from 3"-fluoro-3,2':3',4"-terpyridine-5',6'-diamine (Intermediate 1, 0.1 g, 0.356 mmol) and isonicotinoyl chloride (0.070 g, 0.391 mmol) following the procedure described in Example 6.

δ $^1$H-NMR (CDCl$_3$): 7.24-7.34 (m, 3H), 7.65-7.69 (m, 1H), 8.12-8.20 (m, 3H), 8.38-8.44 (m, 2H), 8.53-8.55 (m, 1H), 8.68-8.70 (m, 1H), 8.79-8.82 (m, 2H)

ESI/MS m/e: 369 ([M+H]$^+$, C$_{21}$H$_{13}$FN$_6$)

Example 13

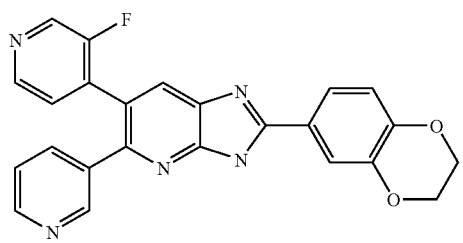

2-(2,3-Dihydro-1,4-benzodioxin-6-yl)-6-(3-fluoropyridin-4-yl)-5-pyridin-3-yl-3H-imidazo[4,5-b]pyridine Obtained (0.027 g, 18% of yield) from 3"-fluoro-3,2':3',4"-terpyridine-5',6'-diamine (Intermediate 1, 0.1 g, 0.356 mmol) and 2,3-dihydro-1,4-benzodioxine-6-carbonyl chloride (0.078 g, 0.391 mmol) following the procedure described in Example 6.

δ $^1$H-NMR (CDCl$_3$): 4.37 (s, 4H), 7.05-7.34 (m, 4H), 7.36-7.43 (d, 1H), 7.82-7.87 (m, 2H), 8.10 (s, 1H), 8.42-8.49 (m, 2H), 8.66-8.69 (m, 1H), 9.64 (s, 1H).
ESI/MS m/e: 426 ([M+H]$^+$, C$_{24}$H$_{16}$FN$_5$O$_2$)

Example 14

Step a

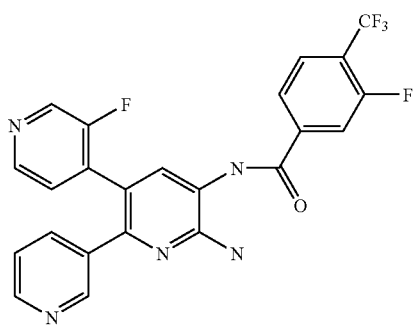

N-(6'-Amino-3"-fluoro-3,2':3',4"-terpyridin-5'-yl)-3-fluoro-4-methylbenzamide

To a solution of 3"-fluoro-3,2':3',4"-terpyridine-5',6'-diamine (Intermediate 1, 0.2 g, 0.71 mmol) in pyridine (2 mL), 0.071 mL (0.78 mmol) of 3-fluoro-4-methylbenzoyl chloride were added. The mixture was heated at 40° C. for 4 h and the solvent was evaporated. The crude mixture was extracted between ethyl acetate and water, the organic layer was dried (MgSO$_4$) and evaporated to give the title compound (0.295 g, 88% of yield) which was used in the next step without further purification.
ESI/MS m/e: 418 ([M+H]$^+$, C$_{23}$H$_{17}$F$_2$N$_5$O)

Step b

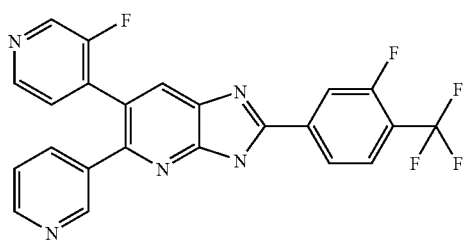

6-(3-Fluoropyridin-4-yl)-2-[3-fluoro-4-(trifluoromethyl)phenyl]-5-pyridin-3-yl-3H-imidazo[4,5-b]pyridine Obtained (0.043 g, 15% of yield) from N-(6'-amino-3"-fluoro-3,2':3',4"-terpyridin-5'-yl)-3-fluoro-4-methylbenzamide following the procedure described in Example 2, step b.

δ $^1$H-NMR (CDCl$_3$): 7.19-7.24 (m, 2H), 7.38-7.46 (m, 2H), 7.83-7.91 (t, 1H), 8.21 (s, 1H), 8.22-8.29 (m, 2H), 8.45 (s, 1H), 8.52-8.55 (d, 1H), 8.69-8.71 (d, 1H), 9.89 (s, 1H).
ESI/MS m/e: 454 ([M+H]$^+$, C$_{23}$H$_{12}$F$_5$N$_5$)

Example 15

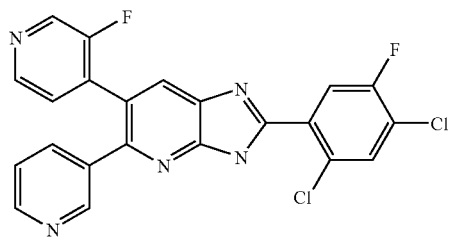

2-(2,4-Dichloro-5-fluorophenyl)-6-(3-fluoropyridin-4-yl)-5-pyridin-3-yl-3H-imidazo[4,5-b]pyridine Obtained (0.075 g, 47% of yield) from 3"-fluoro-3,2':3',4"-terpyridine-5',6'-diamine (Intermediate 1, 0.1 g, 0.356 mmol) and 2,4-dichloro-5-fluorobenzoyl chloride (0.070 g, 0.391 mmol) following the procedure described in Example 6.
ESI/MS m/e: 454 ([M+H]$^+$, C$_{22}$H$_{11}$Cl$_2$F$_2$N$_5$)

Example 16

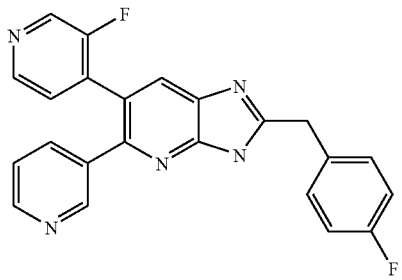

2-(4-Fluorobenzyl)-6-(3-fluoropyridin-4-yl)-5-pyridin-3-yl-3H-imidazo[4,6-b]pyridine Obtained (0.035 g, 25% of yield) from 3"-fluoro-3,2':3',4"-terpyridine-5',6'-diamine (Intermediate 1, 0.1 g, 0.356 mmol) and (4-fluorophenyl)acetyl chloride (0.054 mL, 0.391 mmol) following the procedure described in Example 6.

δ $^1$H-NMR (CDCl$_3$): 4.33 (s, 2H), 7.01-7.09 (m, 2H), 7.25-7.38 (m, 4H), 7.55-7.59 (d, 1H), 8.02 (s, 1H), 8.36-8.42 (m, 3H), 8.46-8.49 (d, 1H), 8.70 (s, 1H).
ESI/MS m/e: 400 ([M+H]$^+$, C$_{23}$H$_{15}$F$_2$N$_5$)

Example 17

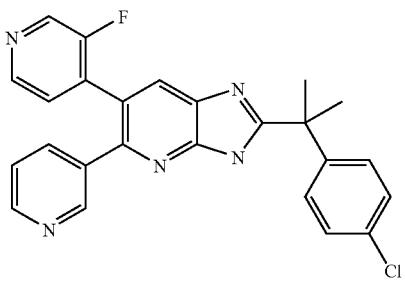

2-[1-(4-Chlorophenyl)-1-methylethyl]-6-(3-fluoropyridin-4-yl)-5-pyridin-3-yl-3H-imidazo[4,5-b]pyridine Obtained (0.040 g, 49% of yield) from 3"-fluoro-3,2':3',4"-terpyridine-5',6'-diamine (Intermediate 1, 0.1 g, 0.356 mmol) and 2-(4-chlorophenyl)-2-methylpropanoyl chloride (0.14 g, 0.651 mmol) following the procedure described in Example 6.

δ $^1$H-NMR (CDCl$_3$): 1.61 (s, 6H), 7.00-7.06 (m, 2H), 7.26-7.38 (m, 4H), 8.08-8.14 (m, 3H), 8.42-8.44 (m, 1H), 8.46-8.48 (d, 2H), 9.30 (s, 1H).

ESI/MS m/e: 444 ([M+H]$^+$, C$_{25}$H$_{19}$ClFN$_5$)

Example 18

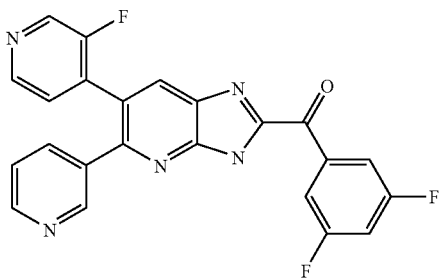

(3,5-Difluorophenyl)[6-(3-fluoropyridin-4-yl)-5-pyridin-3-yl-3H-imidazo[4,5-b]pyridin-2-yl]methanone To a solution of 3"-fluoro-3,2':3',4"-terpyridine-5',6'-diamine (Intermediate 1, 0.1 g, 0.79 mmol) in pyridine (2 mL), 0.071 mL (0.78 mmol) of 3,5-difluorobenzoyl chloride were added. The mixture was stirred at room temperature for 16 h and the solvent was evaporated. The crude mixture was purified by flash chromatography (95:5 dichloromethane/methanol) to give the title compound (0.015 g, 10% of yield).

δ $^1$H-NMR (CDCl$_3$): 6.96-7.08 (m, 1H), 7.22-7.35 (m, 3H), 7.75 (s, 1H), 7.82-7.87 (m, 1H), 8.18-8.24 (m, 2H), 8.45-8.47 (m, 2H), 8.56-8.58 (m, 2H).

ESI/MS m/e: 432 ([M+H]$^+$, C$_{23}$H$_{12}$F$_3$N$_5$O)

Example 19

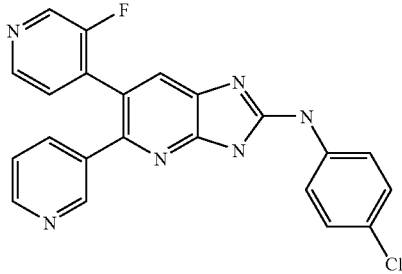

N-(4-Chlorophenyl)-6-(3-fluoropyridin-4-yl)-5-pyridin-3-yl-3H-imidazo[4,5-b]pyridin-2-amine To a solution of 3"-fluoro-3,2':3',4"-terpyridine-5',6'-diamine (Intermediate 1, 0.050 g, 0.179 mmol) and 1-chloro-4-isothiocyanatobenzene (0.045 g, 0.267 mmol) in ethanol (1 mL), 1,3-diisopropylcarbodiimide (0.042 mL, 0.267 mmol) was added. The mixture was heated at 50° C. for 2 h. After cooling at room temperature, the solid precipitated was filtered off to give the title compound (0.035 g, 47% of yield).

δ $^1$H-NMR (MeOD): 7.34-7.38 (m, 3H), 7.44-7.49 (dd, 1H), 7.67-7.70 (m, 2H), 7.73 (s, 1H), 7.77-7.84 (m, 1H), 8.34-8.48 (m, 5H).

ESI/MS m/e: 417 ([M+H]$^+$, C$_{22}$H$_{14}$ClFN$_6$)

Example 20

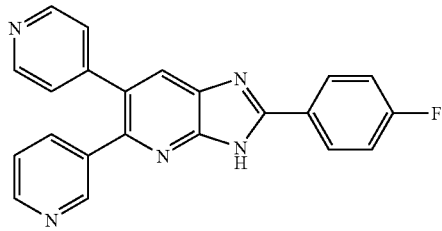

2-(4-Fluorophenyl)-5-pyridin-3-yl-6-pyridin-4-yl-3H-imidazo[4,5-b]pyridine

A sealed tube containing 3,2':3',4"-terpyridine-5',6'-diamine (Intermediate 2,148 mg, 0.56 mmol), 4-fluorobenzaldehyde (57.0 μL, 0.53 mmol) and dioxane (3 mL) was filled with air and heated to 100° C. for 6 days. Then, the solvent was removed and CH$_3$CN (2 mL) followed by Yb(OTf)$_3$ were added, and the reaction mixture was stirred for 4 days at room temperature. Afterwards, the solvent was evaporated in vacuo and the residue was purified by flash column chromatography (CH$_2$Cl$_2$/EtOH/aq NH$_3$ 100:8:1) to afford the title compound as a white solid (27 mg, 13%).

δ $^1$H-NMR (CDCl$_3$): 7.14-7.34 (m, 6H), 7.40-7.48 (m, 1H), 8.12 (s, 1H), 8.32 (dd, 2H), 8.60 (d, 2H), 8.62 (s, 1H), 9.58 (broad s, 1H).

ESI/MS m/e: 368 ([M+H]$^+$, C$_{22}$H$_{14}$FN$_5$).

Example 21

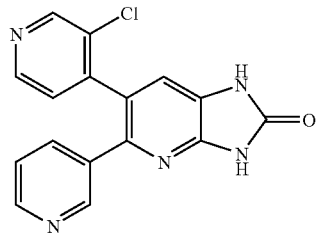

6-(3-Chloropyridin-4-yl)-5-pyridin-3-yl-1,3-dihydro-2H-imidazo[4,5-b]pyridin-2-one Following the same protocol as in Example 1, but using 3"-chloro-3,2':3',4"-terpyridine-5',6'-diamine (Intermediate 3), the title compound was obtained as a white solid (29 mg, 17%).

δ ¹H-NMR (CDCl₃): 7.10-7.16 (m, 4H), 7.50 (dt, 1H), 7.80 (broad s, 1H), 8.44 (d, 1H), 8.49 (dd, 1H), 8.61 (s, 1H), 8.80 (d, 1H).
ESI/MS m/e: 324 ([M+H]⁺, $C_{16}H_{10}ClN_5O$).

Example 22

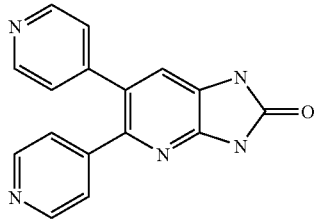

5,6-Dipyridin-4-yl-1,3-dihydro-2H-imidazo[4,5-b]pyridin-2-one

Obtained (0.012 g, 23% of yield) from 4,2':3',4''-terpyridine-5',6'-diamine (Intermediate 4, 0.048 g, 0.18 mmol) following the procedure described in Example 1.
ESI/MS m/e: 290 ([M+H]⁺, $C_{16}H_{11}N_5O$)

Example 23

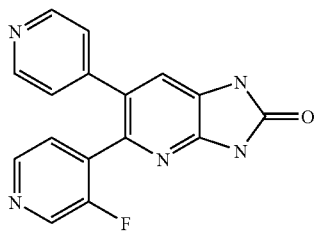

5-(3-Fluoropyridin-4-yl)-6-pyridin-4-yl-1,3-dihydro-2H-imidazo[4,5-b]pyridin-2-one Obtained (0.024 g, 15% of yield) from 3-fluoro-4,2':3',4''-terpyridine-5',6'-diamine (Intermediate 5, 0.173 g, 1.06 mmol) following the procedure described in Example 1.
ESI/MS m/e: 308 ([M+H]⁺, $C_{16}H_{10}FN_5O$)

Example 24

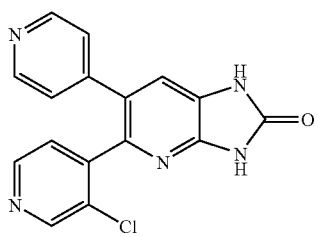

5-(3-Chloropyridin-4-yl)-6-pyridin-4-yl-1,3-dihydro-2H-imidazo[4,5-b]pyridin-2-one Following the same protocol as in Example 1, but using 3-chloro-4,2':3',4''-terpyridine-5',6'-diamine (Intermediate 6), the title compound was obtained as a white solid (74 mg, 65%).
δ ¹H-NMR (DMSO-d₆): 7.11 (broad d, 2H), 7.35 (s, 1H), 7.41 (d, 1H), 8.41 (broad d, 2H), 8.47 (d, 1H), 8.54 (s, 1H), 11.24 (broad s, 1H), 11.69 (broad s, 1H).
ESI/MS m/e: 324 ([M+H]⁺, $C_{16}H_{10}ClN_5O$).

Example 25

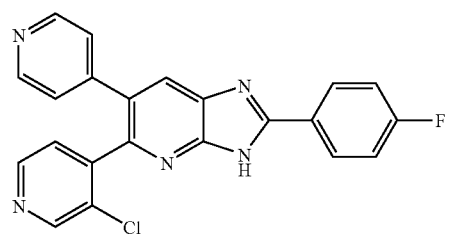

5-(3-Chloropyridin-4-yl)-2-(4-fluorophenyl)-6-pyridin-4-yl-3H-imidazo[4,5-b]pyridine Following the same protocol as in Example 5, but using 3-chloro-4,2':3',4''-terpyridine-5',6'-diamine (Intermediate 6), the title compound was obtained as a white solid (68 mg, 34%).
δ ¹H-NMR (CDCl₃): 7.15 (d, 2H), 7.23-7.32 (m, 3H), 8.14-8.25 (m, 2H), 8.21 (dd, 1H), 8.49 (m, 1H), 8.51 (d, 2H), 8.58 (s, 1H).
ESI/MS m/e: 402 ([M+H]⁺, $C_{22}H_{13}ClFN_5$).

Example 26

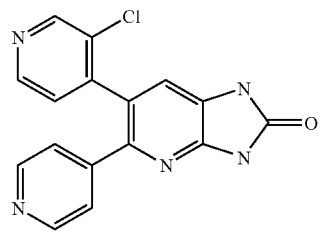

6-(3-Chloropyridin-4-yl)-5-pyridin-4-yl-1,3-dihydro-2H-imidazo[4,5-b]pyridin-2-one Obtained (0.021 g, 23% of yield) from 3''-chloro-4,2':3',4''-terpyridine-5',6'-diamine (Intermediate 7, 0.082 g, 0.275 mmol) following the procedure described in Example 1.
δ ¹H-NMR (DMSO-d₆): 7.13-7.16 (m, 2H), 7.26 (s, 1H), 7.41-7.43 (m, 1H), 8.41-8.43 (m, 2H), 8.48-8.51 (m, 1H), 8.62 (s, 1H).
ESI/MS m/e: 324 ([M+H]⁺, $C_{16}H_{10}ClN_5O$)

Example 27

Step a

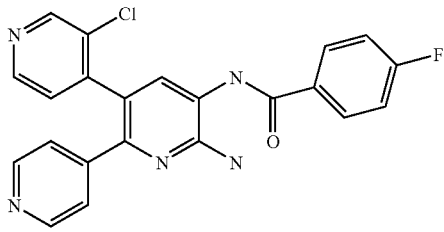

N-(6'-Amino-3''-chloro-4,2':3',4''-terpyridin-5'-yl)-4-fluorobenzamide

Obtained (0.335 g, 95% of yield) from 3''-chloro-4,2':3',4''-terpyridine-5',6'-diamine (Intermediate 7, 0.250 g, 0.84 mmol) and 4-fluorobenzoyl chloride (0.120 mL, 1.01 mmol) following the procedure described in Example 2, step a. The crude mixture was used in the next step without further purification.

ESI/MS m/e: 420 ([M+H]$^+$, $C_{22}H_{15}ClFN_5O$)

Step b

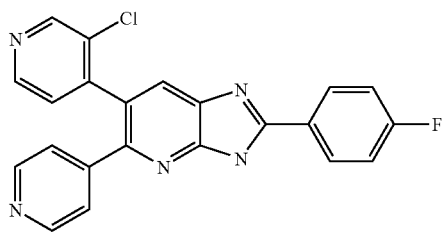

6-(3-Chloropyridin-4-yl)-2-(4-fluorophenyl)-5-pyridin-4-yl)-3H-imidazo[4,5-b]pyridine Obtained (0.099 g, 31% of yield) from N-(6'-amino-3''-chloro-4,2':3',4''-terpyridin-5'-yl)-4-fluorobenzamide (0.005 g, 0.8 mmol) following the procedure described in Example 2, step b.

δ $^1$H-NMR (DMSO-d$_6$): 7.25-7.28 (m, 2H), 7.41-7-54 (m, 3H), 8.08 (s, 1H), 8.30-8.37 (m, 2H), 8.46-8.49 (m, 2H), 8.54-8.56 (d, 1H), 8.64 (s, 1H).

ESI/MS m/e: 402 ([M+H]$^+$, $C_{22}H_{13}ClFN_5$)

Example 28

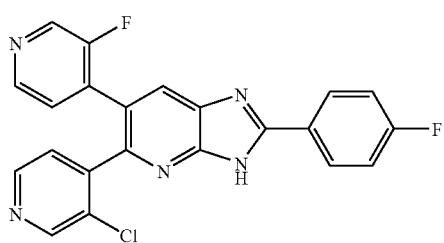

5-(3-Chloropyridin-4-yl)-2-(4-fluorophenyl)-6-(3-fluoropyridin-4-yl)-3H-imidazo[4,5-b]pyridine Following the same protocol as in Example 2, but using 4-fluorobenzoylchloride and 3-chloro-3''-fluoro-4,2':3',4''-terpyridine-5',6'-diamine (Intermediate 8), the title compound was obtained as a white solid (13 mg, 12%).

ESI/MS m/e: 420 ([M+H]$^+$, $C_{22}H_{12}ClF_2N_5$).

Example 29

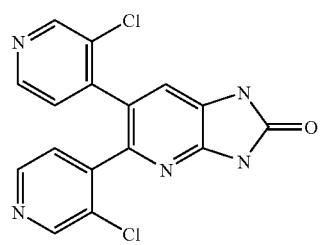

5,6-Bis(3-chloropyridin-4-yl)-1,3-dihydro-2H-imidazo[4,5-b]pyridin-2-one

Obtained (0.026 g, 84% of yield) from 3,3''-dichloro-4,2':3',4''-terpyridine-5',6'-diamine (Intermediate 9, 0.029 g, 0.09 mmol) following the procedure described in Example 1.

ESI/MS m/e: 358 ([M+H]$^+$, $C_{16}H_9Cl_2N_5O$)

Example 30

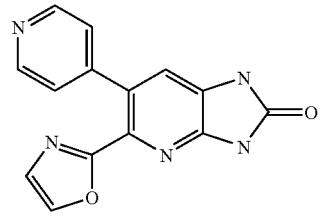

5-(1,3-Oxazol-2-yl)-6-pyridin-4-yl-1,3-dihydro-2H-imidazo[4,5-b]pyridin-2-one

A solution of 2-(1,3-oxazol-2-yl)-3,4'-bipyridine-5,6-diamine (Intermediate 10, 0.077 g, 0.3 mmol), N,N'-carbonyldiimidazole (0.146 g, 0.9 mmol) and triethylamine (91 mg, 0.9 mmol) in N,N-dimethylformamide (1 mL) was heated to 100° C. in a sealed tube. After 4 hours, the mixture was cooled and concentrated in vacuo. Water was added to the residue and the solid that separated was washed with water and dried to give the title compound (0.038 g, 45%) as a white solid.

δ $^1$H-NMR (DMSO-d$_6$): 7.21 (d, 2H), 7.29 (s, 1H), 8.08 (s, 1H), 8.51 (d, 2H), 11.39 (s, 1H), 11.78 (s, 1H).

ESI/MS m/e: 280 ([M+H]+, $C_{14}H_9N_5O_2$)

Example 31

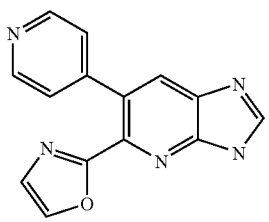

5-(1,3-Oxazol-2-yl)-6-pyridin-4-yl-3H-imidazo[4,5-b]pyridine

A mixture of 2-(1,3-oxazol-2-yl)-3,4'-bipyridine-5,6-diamine (Intermediate 10, 0.100 g, 0.39 mmol) and triethylorthoformate (0.117 g, 0.79 mmol) in glacial acetic acid (2 mL) was heated in a sealed tube to 140° C. After stirring for 2 hours, the mixture was cooled and taken to pH 7 with 6N aqueous sodium hydroxide solution. Ethyl acetate was added to the mixture and, after stirring for 30 minutes, the separated solid was filtered, washed with diethyl ether and dried in vacuo to give the title compound (0.047 g, 49%) as an off-white solid.

δ $^1$H-NMR (DMSO-d$_6$): 7.20 (m, 3H), 8.06 (m, 2H), 8.50 (d, 2H), 8.60 (s, 1H).

ESI/MS m/e: 264 ([M+H]+, $C_{14}H_9N_5O$)

Example 32

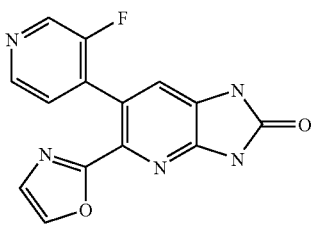

6-(3-Fluoropyridin-4-yl)-5-(1,3-oxazol-2-yl)-1,3-dihydro-2H-imidazo[4,5-b]pyridin-2-one Obtained (37%) from 3'-fluoro-2-(1,3-oxazol-2-yl)-3,4'-bipyridine-5,6-diamine (Intermediate 11) and N,N'-carbonyldiimidazole following the procedure described for preparation of example 30.

δ $^1$H-NMR (DMSO-d$_6$): 7.18 (s, 1H), 7.31 (s, 1H), 7.47 (dd, 1H), 8.12 (s, 1H), 8.49 (m, 2H), 11.36 (s, 1H), 11.85 (s, 1H).

ESI/MS m/e: 298 ([M+H]+, $C_{14}H_8FN_5O_2$)

Example 33

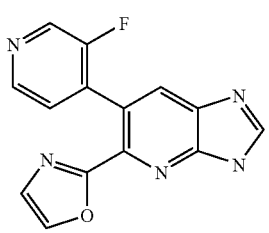

6-(3-Fluoropyridin-4-yl)-5-(1,3-oxazol-2-yl)-3H-imidazo[4,5-b]pyridine

Obtained (26%) from 3'-fluoro-2-(1,3-oxazol-2-yl)-3,4'-bipyridine-5,6-diamine (Intermediate 11) and triethylorthoformate following the procedure described for preparation of example 31.

δ $^1$H-NMR (DMSO-d$_6$): 7.21 (s, 1H), 7.53 (dd, 1H), 8.18 (m, 2H), 8.50 (m, 2H), 8.71 (s, 1H).

ESI/MS m/e: 282 ([M+H]+, $C_{14}H_8FN_5O$)

Example 34

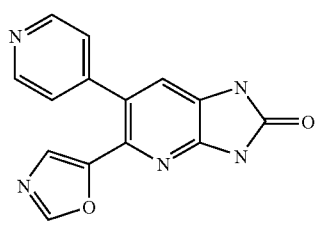

5-(1,3-Oxazol-5-yl)-6-pyridin-4-yl-1,3-dihydro-2H-imidazo[4,5-b]pyridin-2-one

Obtained (58%) from 2-(1,3-oxazol-5-yl)-3,4'-bipyridine-5,6-diamine (Intermediate 12) and N,N'-carbonyldiimidazole following the procedure described for preparation of example 30.

δ $^1$H-NMR (DMSO-d$_6$): 6.92 (s, 1H), 7.20 (s, 1H), 7.30 (d, 2H), 8.24 (s, 1H), 8.58 (d, 2H), 11.21 (s, 1H), 11.69 (s, 1H).

ESI/MS m/e: 278 ([M−H]+, $C_{14}H_9N_5O_2$)

Example 35

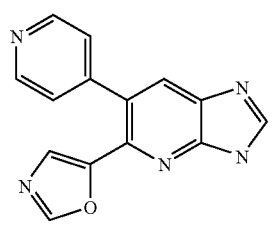

5-(1,3-oxazol-5-yl)-6-pyridin-4-yl-3H-imidazo[4,5-b]pyridine

Obtained (66%) from 2-(1,3-oxazol-5-yl)-3,4'-bipyridine-5,6-diamine (Intermediate 12) and triethylorthoformate following the procedure described for preparation of example 31.

δ $^1$H-NMR (DMSO-d$_6$): 7.00 (m, 1H), 7.36 (m, 2H), 8.00 (m, 1H), 8.31 (s, 1H), 8.62 (m, 3H), 13.0 (s, 1H).

ESI/MS m/e: 264 ([M+H]+, $C_{14}H_9N_5O$)

Example 36

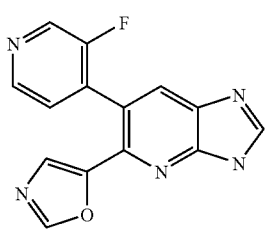

6-(3-Fluoropyridin-4-yl)-5-(1,3-oxazol-5-yl)-3H-imidazo[4,5-b]pyridine

Obtained (25%) from 3'-fluoro-2-(1,3-oxazol-5-yl)-3,4'-bipyridine-5,6-diamine (Intermediate 13) and triethylorthoformate following the procedure described for preparation of example 31.

δ $^1$H-NMR (DMSO-d$_6$): 7.17 (s, 1H), 7.58 (dd, 1H), 8.15 (s, 1H), 8.32 (s, 1H), 8.55 (dd, 1H), 8.65 (m, 2H).

ESI/MS m/e: 282 ([M+H]+, C$_{14}$H$_8$FN$_5$O)

Example 37

Step a

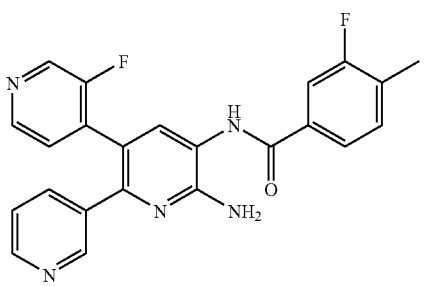

N-(6'-Amino-3''-fluoro-3,2':3',4''-terpyridin-5'-yl)-3-fluoro-4-methylbenzamide

To a solution of 3''-fluoro-3,2':3',4''-terpyridine-5',6'-diamine (Intermediate 1, 0.1 g, 0.356 mmol) in pyridine (2 mL), 0.15 g (0.89 mmol) of 3-fluoro-4-methylbenzoyl chloride were added. The mixture was stirred at room temperature overnight and the solvent was evaporated. The crude mixture (0.33 g) was purified by silica gel flash chromatography (95:5 dichloromethane/methanol) to give the title compound (0.12 g, 81% of yield).

ESI/MS m/e: 418 ([M+H]$^+$, C$_{23}$H$_{17}$F$_2$N$_5$O)

Step b

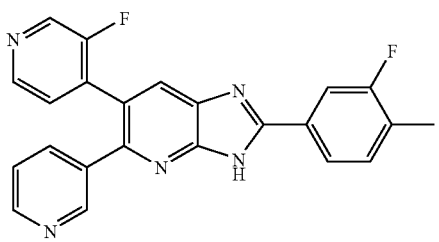

2-(3-Fluoro-4-methylphenyl)-6-(3-fluoropyridin-4-yl)-5-pyridin-3-yl-3H-imidazo[4,5-b]pyridine A solution of N-(6'-amino-3''-fluoro-3,2':3',4''-terpyridin-5'-yl)-3-fluoro-4-methylbenzamide (0.12 g, 0.288 mmol) in acetic acid (2 mL) was heated in a sealed tube at 118° C. for 16 h. The solvent was evaporated and 4% sodium bicarbonate aqueous solution was added and extracted with ethyl acetate. The organic layer was dried and evaporated. The residue was purified by silica gel flash chromatography (95:5 dichloromethane/methanol) to give the title compound (0.03 g, 26% of yield).

δ $^1$H-NMR (CDCl$_3$): 2.41 (s, 3H), 7.17-7.50 (m, 4H), 7.96 (m, 1H), 8.01 (s, 1H), 8.14 (s, 1H), 8.43 (d, 1H), 8.49 (dd, 1H), 8.65 (dd, 1H), 9.57 (m, 1H).

ESI/MS m/e: 400 ([M+H]$^+$, C$_{23}$H$_{15}$F$_2$N$_5$).

Example 38

Step a

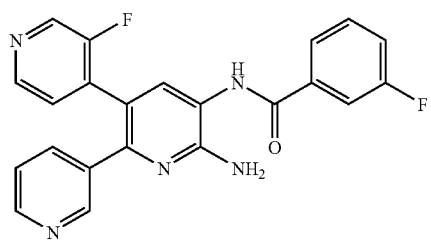

N-(6'-Amino-3''-fluoro-3,2':3',4''-terpyridin-5'-yl)-3-fluorobenzamide

Obtained (0.180 g) from 3''-fluoro-3,2':3',4''-terpyridine-5',6'-diamine (Intermediate 1, 0.1 g, 0.356 mmol) and 3-fluorobenzoyl chloride (0.048 mL, 0.392 mmol) following the procedure described in Example 6, step a.

ESI/MS m/e: 404 ([M+H]$^+$, C$_{22}$H$_{15}$F$_2$N$_5$O)

Step b

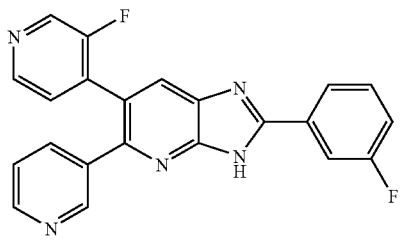

2-(3-Fluorophenyl)-6-(3-fluoropyridin-4-yl)-5-pyridin-3-yl-3H-imidazo[4,6-b]pyridine Obtained (0.035 g, 26% of yield) from N-(6'-amino-3''-fluoro-3,2':3',4''-terpyridin-5'-yl)-3-fluorobenzamide following the procedure described in Example 37, step b.

δ $^1$H-NMR (CDCl$_3$): 7.20 (m, 1H), 7.39 (m, 3H), 7.60 (td, 1H), 8.09 (m, 2H), 8.16 (s, 1H), 8.44 (s, 1H), 8.50 (d, 1H), 8.68 (dd, 1H), 9.73 (s, 1H).

ESI/MS m/e: 386 ([M+H]$^+$, C$_{22}$H$_{13}$F$_2$N$_5$).

Example 39

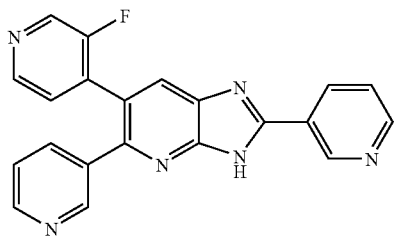

6-(3-Fluoropyridin-4-yl)-2,5-dipyridin-3-yl-3H-imidazo[4,5-b]pyridine

Obtained (0.025 g, 24% of yield) from 3"-fluoro-3,2':3',4"-terpyridine-5',6'-diamine (Intermediate 1, 0.1 g, 0.356 mmol) and nicotinoyl chloride hydrochloride (0.070 g, 0.392 mmol) following the procedure described in Example 38.

δ $^1$H-NMR (CDCl$_3$): 7.21 (m, 1H), 7.41 (m, 2H), 7.59 (m, 1H), 8.20 (s, 1H), 8.45 (s, 1H), 8.52 (m, 1H), 8.69 (s, 1H), 8.72 (s, 1H), 8.82 (m, 1H), 9.61 (m, 1H), 9.82 (m, 1H).

ESI/MS m/e: 369 ([M+H]$^+$, C$_{21}$H$_{13}$FN$_6$).

Example 40

Step a

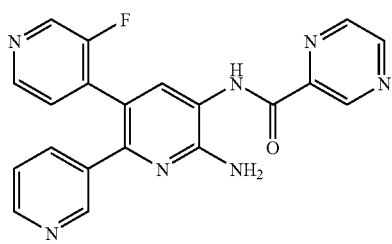

N-(6'-Amino-3"-fluoro-3,2':3',4"-terpyridin-5'-yl)pyrazine-2-carboxamide

A solution of pyrazine-2-carboxylic acid (0.114 g, 0.924 mmol), N-[3-(dimethylamino)propyl]-N'-ethylcarbodiimide hydrochloride (0.178 g, 0.924 mmol) and 1H-1,2,3-benzotriazol-1-ol (0.096 g, 0.712 mmol) in DMF (6 mL) was heated at 40° C. for 15 minutes. Finally, 3"-fluoro-3,2':3',4"-terpyridine-5',6'-diamine (Intermediate 1, 0.1 g, 0.356 mmol) in DMF (1 mL) was added and the mixture was stirred at room temperature overnight. The crude mixture was extracted between ethyl acetate and water. The organic layer was washed with 4% sodium bicarbonate aqueous solution and water, dried (MgSO$_4$) and evaporated. The residue was purified by silica gel flash chromatography (90:10 dichloromethane/methanol) to give the title compound (0.057 g, 41% of yield).

ESI/MS m/e: 388 ([M+H]$^+$, C$_{20}$H$_{14}$FN$_7$O).

Step b

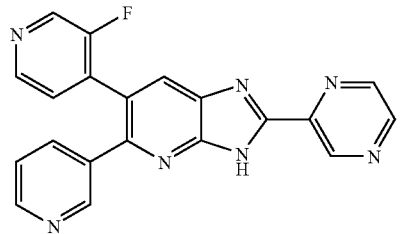

6-(3-Fluoropyridin-4-yl)-2-pyrazin-2-yl-5-pyridin-3-yl-3H-imidazo[4,5-b]pyridine Obtained (0.016 g, 28% of yield) from N-(6'-amino-3"-fluoro-3,2':3',4"-terpyridin-5'-yl)pyrazine-2-carboxamide following the procedure described in Example 37, step b.

δ $^1$H-NMR (CDCl$_3$): 7.20-7.35 (m, 3H), 7.57 (m, 1H), 8.22 (s, 1H), 8.43 (m, 1H), 8.48 (d, 1H), 8.72-8.77 (m, 3H), 9.24 (m, 1H), 9.75 (d, 1H).

ESI/MS m/e: 370 ([M+H]$^+$, C$_{20}$H$_{12}$FN$_7$).

Example 41

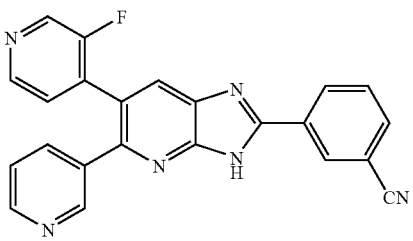

3-[6-(3-Fluoropyridin-4-yl)-5-pyridin-3-yl-3H-imidazo[4,5-b]pyridin-2-yl]benzonitrile Obtained (0.11 g, 53% of yield) from 3"-fluoro-3,2':3',4"-terpyridine-5',6'-diamine (Intermediate 1, 0.15 g, 0.534 mmol) and 3-cyanobenzoyl chloride (0.133 g, 0.803 mmol) following the procedure described in Example 38.

δ $^1$H-NMR (CDCl$_3$): 7.22 (m, 1H), 7.37-7.45 (m, 2H), 7.72-7.88 (m, 2H), 8.19 (s, 1H), 8.46 (d, 1H), 8.54 (d, 1H), 8.64 (d, 1H), 8.71 (m, 1H), 8.73 (m, 1H), 9.92 (m, 1H).

ESI/MS m/e: 393 ([M+H]$^+$, C$_{23}$H$_{13}$FN$_6$).

Example 42

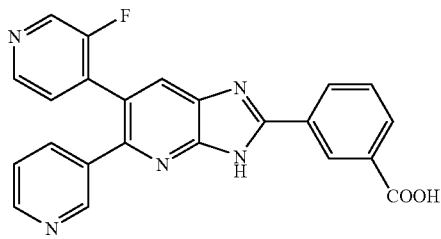

3-[6-(3-Fluoropyridin-4-yl)-5-pyridin-3-yl-3H-imidazo[4,6-b]pyridin-2-yl]benzoic acid To a solution of 3-[6-(3-fluoropyridin-4-yl)-5-pyridin-3-yl-3H-imidazo[4,5-b]pyridin-2-yl]benzonitrile (Example 41, 0.1 g, 0.255 mmol) in a mixture of THF/water 1:2.5 (0.83 mL), 37% hydrogen chloride aqueous solution (1.07 mL) was added. The mixture was heated at 70° C. for 4 days. After cooling at room temperature, the solid precipitated was filtered off to give the title compound (0.070 g, 67% of yield).
ESI/MS m/e: 412 ([M+H]$^+$, $C_{23}H_{14}FN_5O_2$).

Example 43

Step a

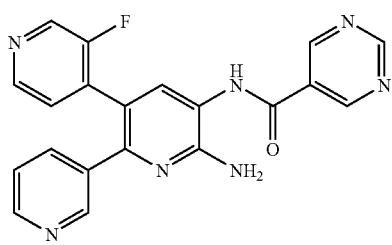

N-(6'-Amino-3''-fluoro-3,2':3',4''-terpyridin-5'-yl)pyrimidine-5-carboxamide

A solution of pyrimidine-5-carboxylic acid (0.088 g, 0.709 mmol), N-[3-(dimethylamino)propyl]-N'-ethylcarbodiimide hydrochloride (0.136 g, 0.709 mmol) and 1H-1,2,3-benzotriazol-1-ol (0.072 g, 0.534 mmol) in DMF (4 mL) was heated at 40° C. for 15 minutes. Finally, 3''-fluoro-3,2':3',4''-terpyridine-5',6'-diamine (Intermediate 1, 0.15 g, 0.534 mmol) in DMF (4 mL) was added and the mixture was stirred at room temperature overnight. The crude mixture was extracted between ethyl acetate and water. The organic layer was washed with 4% sodium bicarbonate aqueous solution and water, dried (MgSO$_4$) and evaporated. The residue (0.2 g) was used in the next step without further purification.
ESI/MS m/e: 388 ([M+H]$^+$, $C_{20}H_{14}FN_7O$).

Step b

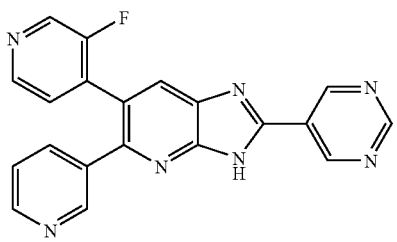

6-(3-Fluoropyridin-4-yl)-5-pyridin-3-yl-2-pyrimidin-6-yl-3H-imidazo[4,5-b]pyridine Obtained (0.024 g, 12% of yield) from N-(6'-amino-3''-fluoro-3,2':3',4''-terpyridin-5'-yl)pyrimidine-5-carboxamide following the procedure described in Example 37, step b.
ESI/MS m/e: 370 ([M+H]$^+$, $C_{20}H_{12}FN_7$).

Example 44

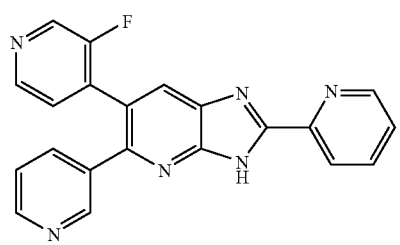

6-(3-Fluoropyridin-4-yl)-2-pyridin-2-yl-5-pyridin-3-yl-3H-imidazo[4,5-b]pyridine Obtained (0.006 g, 18% of yield) from 3''-fluoro-3,2':3',4''-terpyridine-5',6'-diamine (Intermediate 1, 0.1 g, 0.356 mmol) and pyridine-2-carbonyl chloride (0.131 g, 0.926 mmol) following the procedure described in Example 37.
ESI/MS m/e: 369 ([M+H]$^+$, $C_{21}H_{13}FN_6$).

Example 45

Step a

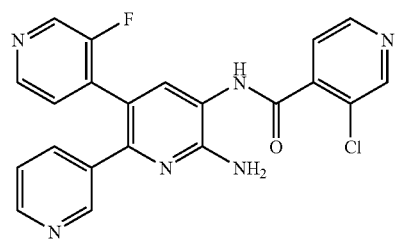

N-(6'-Amino-3''-fluoro-3,2':3',4''-terpyridin-6'-yl)-3-chloroisonicotinamide

A solution of 3-chloroisonicotinic acid (0.075 g, 0.48 mmol), N—[(dimethylamino)(3H-[1,2,3]triazolo[4,5-b]pyridin-3-yloxy)methylene]-N-methylmethanaminium hexafluorophosphate (0.178 g, 0.47 mmol) and N-ethyl-N-isopropylpropan-2-amine (0.15 mL, 0.86 mmol) in DMF (1 mL) was stirred 15 minutes. Finally, 3''-fluoro-3,2':3',4''-terpyridine-5',6'-diamine (Intermediate 1, 0.11 g, 0.39 mmol) in DMF (2.9 mL) was added and the mixture was stirred at room temperature 3.5 hours. The crude mixture was extracted between ethyl acetate and water. The organic layer was washed with water and brine, dried (MgSO$_4$) and evaporated. The residue (0.195 g) was used in the next step without further purification.
ESI/MS m/e: 421 ([M+H]$^+$, $C_{21}H_{14}ClFN_6O$).

Step b

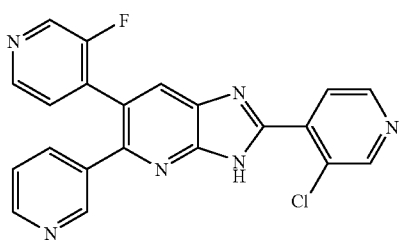

2-(3-Chloropyridin-4-yl)-6-(3-fluoropyridin-4-yl)-5-pyridin-3-yl-3H-imidazo[4,5-b]pyridine Obtained (0.030 g, 16% of yield) from N-(6'-amino-3"-fluoro-3,2':3',4"-terpyridin-5'-yl)-3-chloroisonicotinamide following the procedure described in Example 37, step b.

δ $^1$H-NMR (CDCl$_3$): 7.19 (dd, 1H), 7.31 (t, 1H), 7.57 (d, 1H), 8.25 (m, 2H), 8.42 (s, 1H), 8.47 (d, 1H), 8.57 (dt, 1H), 8.73 (d, 1H), 8.82 (s, 1H), 9.11 (s, 1H).

ESI/MS m/e: 403 ([M+H]$^+$, C$_{21}$H$_{12}$ClFN$_6$).

Example 46

Step a

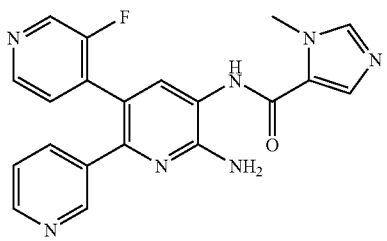

N-(6'-amino-3"-fluoro-3,2':3',4"-terpyridin-5'-yl)-1-methyl-1H-imidazole-5-carboxamide Obtained (0.040 g, 19% of yield) from 3"-fluoro-3,2':3',4"-terpyridine-5',6'-diamine (Intermediate 1, 0.15 g, 0.534 mmol) and 1-methyl-1H-imidazole-5-carboxylic acid (0.088 g, 0.694 mmol) following the procedure described in Example 41, step a.

ESI/MS m/e: 390 ([M+H]$^+$, C$_{20}$H$_{16}$FN$_7$O).

Step b

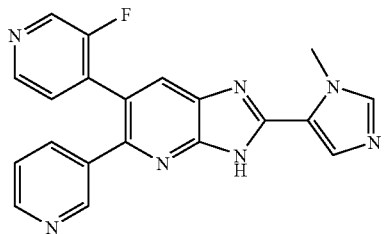

6-(3-Fluoropyridin-4-yl)-2-(1-methyl-1H-imidazol-5-yl)-5-pyridin-3-yl-3H-imidazo[4,5-b]pyridine A solution of N-(6'-amino-3"-fluoro-3,2':3',4"-terpyridin-5'-yl)-1-methyl-1H-imidazole-5-carboxamide (0.040 g, 0.103 mmol) in acetic acid (1 mL) was heated in a sealed tube at 118° C. for 16 h. The solvent was evaporated and 4% sodium bicarbonate aqueous solution was added and extracted with ethyl acetate. The organic layer was dried and evaporated to give the title compound (0.022 g, 58% of yield).

ESI/MS m/e: 372 ([M+H]$^+$, C$_{20}$H$_{14}$FN$_7$).

Example 47

Step a

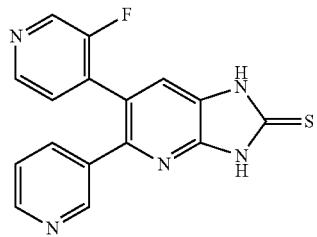

6-(3-Fluoropyridin-4-yl)-5-pyridin-3-yl-1,3-dihydro-2H-imidazo[4,5-b]pyridine-2-thione A solution of 3"-fluoro-3,2':3',4"-terpyridine-5',6'-diamine (Intermediate 1, 2 g, 7.11 mmol), 1,1'-thiocarbonyldiimidazole (2.54 g, 14.22 mmol) and triethylamine (2 mL, 14.22 mmol) in THF (30 mL) was heated at 80° C. in a sealed tube. After 6 hours, the mixture was cooled and the solid was filtered, washed with NH$_4$Cl aq. and water and dried to give the title compound (2.03 g, 88%) as a white solid.

δ $^1$H-NMR (DMSO-d$_6$): 7.31 (dd, 1H), 7.49 (dd, 1H), 7.58 (s, 1H), 7.64 (dt, 1H), 8.39-8.48 (m, 4H).

ESI/MS m/e: 324 ([M+H]+, C$_{16}$H$_{10}$FN$_5$S).

Step b

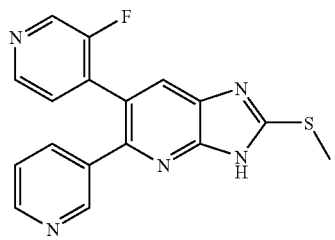

6-(3-Fluoropyridin-4-yl)-2-(methylthio)-5-pyridin-3-yl-3H-imidazo[4,5-b]pyridine To a suspension of sodium hydride 60% (0.098 g, 2.45 mmols) in DMF (5 mL) a suspension of 6-(3-fluoropyridin-4-yl)-5-pyridin-3-yl-1,3-dihydro-2H-imidazo[4,5-b]pyridine-2-thione (0.6 g, 1.86 mmols) in DMF (15 mL) was added dropwise, at 0° C., under argon. The solution was allowed to stir for 30 minutes at 0° C. and then iodomethane (0.116 mL, 1.86 mmol) in DMF (1 mL) was added dropwise. The reaction mixture was warmed up to room temperature and stirred for 2.5 hours. The mixture was concentrated and purified by silica gel flash chromatography (150:40:5 dichloromethane/methanol/ammonia) to give the title compound (0.34 g, 54% of yield).

δ $^1$H-NMR (DMSO-d$_6$): 2.74 (s, 3H), 7.309 (dd, 1H), 7.51 (t, 1H), 7.66 (dt, 2H), 7.98 (s, 1H), 8.43-8.47 (m, 4H).

ESI/MS m/e: 338 ([M+H]+, C$_{17}$H$_{12}$FN$_5$S).

Example 48

Step a

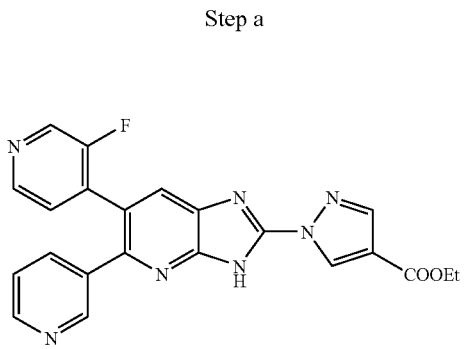

Ethyl 1-[6-(3-fluoropyridin-4-yl)-5-pyridin-3-yl-3H-imidazo[4,5-b]pyridin-2-yl]-1H-pyrazole-4-carboxylate A solution of 6-(3-fluoropyridin-4-yl)-2-(methylthio)-5-pyridin-3-yl-3H-imidazo[4,5-b]pyridine
(Example 47, 0.1 g, 0.3 mmol), ethyl 1H-pyrazole-4-carboxylate (0.125 g, 0.88 mmol) and potassium carbonate (0.164 mg, 1.18 mmol) in DMF (2 mL) was heated at 120° C. in a sealed tube. After 2 days, the solvent was evaporated and the crude mixture was purified by silica gel flash chromatography (100:8:1 dichloromethane/methanol/ammonia) to give the title compound (0.034 g, 27% of yield).
ESI/MS m/e: 430 ([M+H]+, $C_{22}H_{16}FN_7O_2$).

Step b

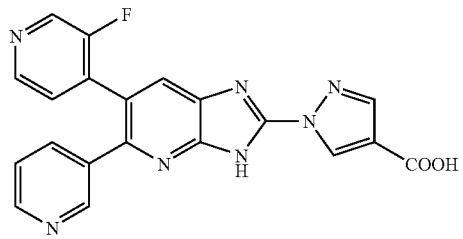

1-[6-(3-Fluoropyridin-4-yl)-5-pyridin-3-yl-3H-imidazo[4,5-b]pyridin-2-yl]-1H-pyrazole-4-carboxylic acid To a solution of ethyl 1-[6-(3-fluoropyridin-4-yl)-5-pyridin-3-yl-3H-imidazo[4,5-b]pyridin-2-yl]-1H-pyrazole-4-carboxylate (0.022 g, 0.05 mmol) in a mixture of THF/ethanol 1:1 (1 mL), 2N sodium hydroxide aqueous solution (0.05 mL) was added. The mixture was heated at 60° C. for 2 hours and then neutralised with 2N hydrogen chloride aqueous solution. The solvent was evaporated and the crude mixture was purified by solid phase extraction, SCX, it was washed with water and eluted with methanol/ammonia (9:1) to give the title compound (0.007 g, 29% of yield).
ESI/MS m/e: 402 ([M+H]+, $C_{20}H_{12}FN_7O_2$).

Example 49

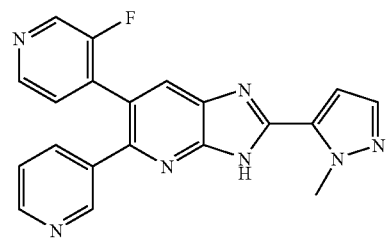

6-(3-Fluoropyridin-4-yl)-2-(1-methyl-1H-pyrazol-5-yl)-5-pyridin-3-yl-3H-imidazo[4,5-b]pyridine Obtained (0.012 g, 24% of yield) from 3"-fluoro-3,2':3',4"-terpyridine-5',6'-diamine (Intermediate 1, 0.2 g, 0.71 mmol), N,N'-dicyclohexylcarbodiimide (0.19 g, 0.92 mmol), 1H-1,2,3-benzotriazol-1-ol (0.099 g, 0.73 mmol) and 1-methyl-1H-pyrazole-5-carboxylic acid (0.116 g, 0.92 mmol) following the procedure described in Example 41.
ESI/MS m/e: 372 ([M+H]+, $C_{20}H_{14}FN_7$).

Example 50

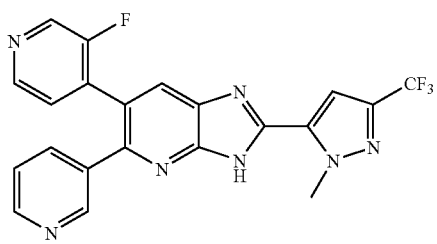

6-(3-Fluoropyridin-4-yl)-2-[1-methyl-3-(trifluoromethyl)-1H-pyrazol-5-yl]-5-pyridin-3-yl-3H-imidazo[4,5-b]pyridine Obtained (0.017 g, 24% of yield) from 3"-fluoro-3,2':3',4"-terpyridine-5',6'-diamine (Intermediate 1, 0.085 g, 0.30 mmol), N,N'-dicyclohexylcarbodiimide (0.074 g, 0.36 mmol), 1H-1,2,3-benzotriazol-1-ol (0.042 g, 0.31 mmol) and 1-methyl-3-(trifluoromethyl)-1H-pyrazole-5-carboxylic acid (0.071 g, 0.36 mmol) following the procedure described in Example 41.
δ $^1$H-NMR (DMSO-$d_6$): 4.45 (s, 3H), 7.33 (dd, 1H), 7.55-7.59 (m, 2H), 7.71 (dt, 1H), 8.31 (s, 1H), 8.48-8.50 (m, 4H).
ESI/MS m/e: 440 ([M+H]+, $C_{21}H_{13}F_4N_7$).

Example 51

Step a

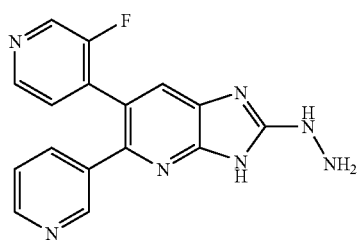

6-(3-fluoropyridin-4-yl)-2-hydrazino-5-pyridin-3-yl-3H-imidazo[4,5-b]pyridine A solution of 6-(3-fluoropyridin-4-yl)-2-(methylthio)-5-pyridin-3-yl-3H-imidazo[4,5-b]pyridine (Example 47, 0.05 g, 0.15 mmol) in hydrazine (0.5 mL) was heated in a sealed tube at 100° C. for 30 hours. The solvent was evaporated and the residue (0.05 g) was used in the next step without further purification.

ESI/MS m/e: 322 ([M+H]+, $C_{16}H_{12}FN_7$).

Step b

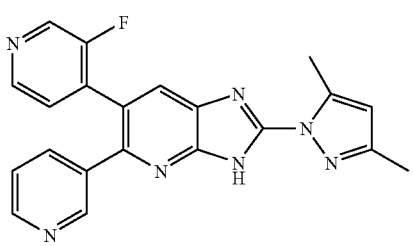

2-(3,5-Dimethyl-1H-pyrazol-1-yl)-6-(3-fluoropyridin-4-yl)-5-pyridin-3-yl-3H-imidazo[4,5-b]pyridine A solution of 6-(3-fluoropyridin-4-yl)-2-hydrazino-5-pyridin-3-yl-3H-imidazo[4,5-b]pyridine (0.05 g, 0.15 mmol), pentane-2,4-dione (0.016 mL, 0.16 mmol) and hydrogen chloride aqueous solution in ethanol (1 mL) was heated in a sealed tube at 80° C. for 16 hours. The acidic pH was neutralized and then the solvent was evaporated and the crude mixture was purified by reverse phase chromatography (water/acetonitrile) to give the title compound (0.015 g, 25% of yield).

ESI/MS m/e: 386 ([M+H]$^+$, $C_{21}H_{16}FN_7$).

Example 52

Step a

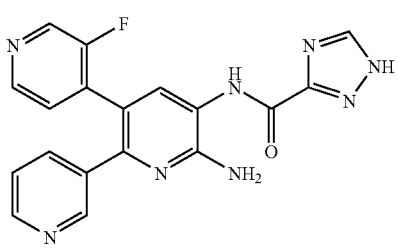

N-(6'-Amino-3"-fluoro-3,2':3',4"-terpyridin-5'-yl)-1H-1,2,4-triazole-3-carboxamide A solution of 1H-1,2,4-triazole-3-carboxylic acid (0.072 g, 0.64 mmol), N-[(dimethylamino)(3H-[1,2,3]triazolo[4,5-b]pyridin-3-yloxy)methylene]-N-methylmethanaminium hexafluorophosphate (0.243 g, 0.64 mmol) and N-ethyl-N-isopropylpropan-2-amine (0.205 mL, 1.17 mmol) in DMF (1.5 mL) was stirred for 15 minutes under argon. Finally, 3"-fluoro-3,2':3',4"-terpyridine-5',6'-diamine (Intermediate 1, 0.15 g, 0.53 mmol) in DMF (3 mL) was added and the mixture was stirred at room temperature for 20 hours. The solvent was evaporated and the crude mixture was purified by silica gel flash chromatography (90:10 dichloromethane/methanol) to give the title compound (0.070 g, 35% of yield).

ESI/MS m/e: 377 ([M+H]+, $C_{18}H_{13}FN_8O$).

Step b

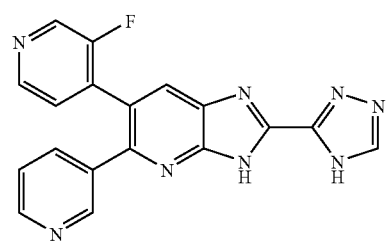

6-(3-Fluoropyridin-4-yl)-5-pyridin-3-yl-2-(4H-1,2,4-triazol-3-yl)-3H-imidazo[4,5-b]pyridine A solution of N-(6'-amino-3"-fluoro-3,2':3',4"-terpyridin-5'-yl)-1H-1,2,4-triazole-3-carboxamide (0.070 g, 0.19 mmol) in acetic acid (2.5 mL) was heated in a sealed tube at 120° C. for 18 h. The solvent was evaporated and the residue was suspended in ethyl acetate and 4% sodium bicarbonate aqueous solution. The solid formed was filtered and dried in vacuo to give the title compound (0.039 g, 59% of yield).

δ $^1$H-NMR (DMSO-d$_6$): 7.33 (m, 1H), 7.56 (m, 1H), 7.69 (m, 1H), 8.13 (m, 1H), 8.47 (m, 4H), 8.69 (m, 1H).

ESI/MS m/e: 359 ([M+H]$^+$, $C_{18}H_{11}FN_8$).

Example 53

Step a

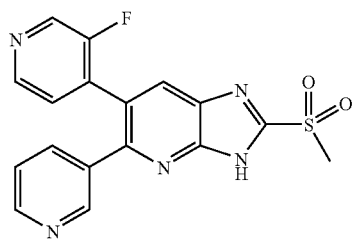

6-(3-Fluoropyridin-4-yl)-2-(methylsulfonyl)-5-pyridin-3-yl-3H-imidazo[4,5-b]pyridine To a solution of 6-(3-fluoropyridin-4-yl)-2-(methylthio)-5-pyridin-3-yl-3H-imidazo[4,5-b]pyridine (Example 47, 0.096 g, 0.285 mmol) in DCM (6 mL) was added 3-chlorobenzenecarboperoxoic acid (0.128 g, 77% purity, 0.570 mmol) at 0° C. The reaction mixture was warmed up to room temperature and stirred for 16 h. The mixture was concentrated and purified by reverse phase chromatography (water/acetonitrile) to give the title compound (0.040 g, 38% of yield).

ESI/MS m/e: 370 ([M+H]+, $C_{17}H_{12}FN_5O_2S$).

Step b

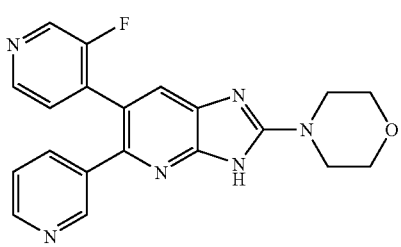

6-(3-Fluoropyridin-4-yl)-2-morpholin-4-yl-5-pyridin-3-yl-3H-imidazo[4,5-b]pyridine A solution of 6-(3-fluoropyridin-4-yl)-2-(methylsulfonyl)-5-pyridin-3-yl-3H-imidazo[4,5-b]pyridine (0.025 g, 0.068 mmol), morpholine (0.024 mL, 0.268 mmol) in dioxane (0.5 mL) was heated in a sealed tube at 120° C. overnight. The solvent was evaporated and the residue was purified by silica gel flash chromatography (95:5 dichloromethane/methanol) to give the title compound (0.011 g, 44% of yield).

ESI/MS m/e: 377 ([M+H]$^+$, $C_{20}H_{17}FN_6O$).

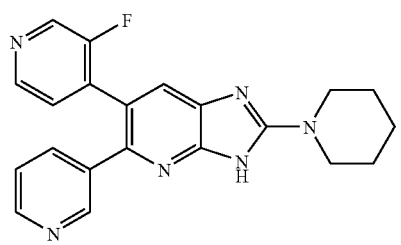

Example 54

6-(3-Fluoropyridin-4-yl)-2-piperidin-1-yl-5-pyridin-3-yl-3H-imidazo[4,5-b]pyridine A solution of 6-(3-fluoropyridin-4-yl)-2-(methylthio)-5-pyridin-3-yl-3H-imidazo[4,5-b]pyridine (Example 47, 0.05 g, 0.15 mmol), piperidine (0.052 mL, 0.45 mmol) and acetic acid in xylene (1 mL) was heated at 120° C. in a sealed tube. After 2 days, the solvent was evaporated and the crude mixture was purified by silica gel flash chromatography (95:5 dichloromethane/methanol) to give the title compound (0.03 g, 54% of yield).

ESI/MS m/e: 430 ([M+H]+, $C_{21}H_{19}FN_6$).

Example 55

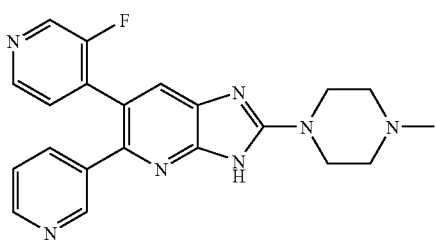

6-(3-Fluoropyridin-4-yl)-2-(4-methylpiperazin-1-yl)-5-pyridin-3-yl-3H-imidazo[4,5-b]pyridine Obtained (0.045 g, 55% of yield) from 6-(3-fluoropyridin-4-yl)-2-(methylthio)-5-pyridin-3-yl-3H-imidazo[4,5-b]pyridine (Example 47, 0.1 g, 0.3 mmol) and 1-methylpiperazine (0.117 mL, 1.05 mmol) following the procedure described in Example 57.

ESI/MS m/e: 390 ([M+H]$^+$, $C_{21}H_{20}FN_7$).

Example 56

Step a

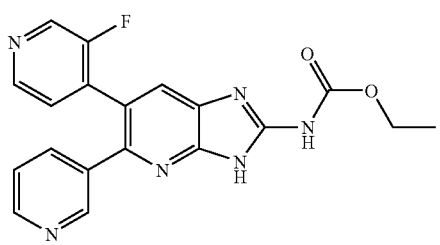

Ethyl [6-(3-fluoropyridin-4-yl)-5-pyridin-3-yl-3H-imidazo[4,5-b]pyridin-2-yl]carbamate Obtained (0.175 g, 87% of yield) from 3"-fluoro-3,2':3',4"-terpyridine-5',6'-diamine (Intermediate 1, 0.15 g, 0.53 mmol) and ethyl isothiocyanatidocarbonate (0.094 mL, 0.8 mmol) following the procedure described in Example 19 (reaction time: 20 h).

δ $^1$H-NMR (CDCl$_3$): 1.37 (t, 3H), 4.37 (q, 2H), 7.23 (m, 2H), 7.70 (d, 1H), 7.81 (s, 1H), 8.39 (m, 2H), 8.51 (d, 1H), 8.57 (m, 1H).

ESI/MS m/e: 379 ([M+H]$^+$, $C_{19}H_{15}FN_6O_2$).

Step b

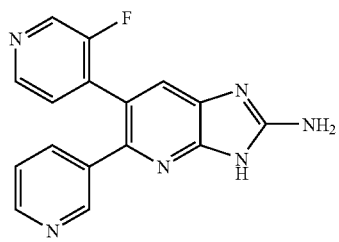

6-(3-Fluoropyridin-4-yl)-5-pyridin-3-yl-3H-imidazo[4,5-b]pyridin-2-amine

A solution of ethyl [6-(3-fluoropyridin-4-yl)-5-pyridin-3-yl-3H-imidazo[4,5-b]pyridin-2-yl]carbamate (0.175 g, 0.46 mmol), potassium hydroxide (0.17 g, 3.01 mmol) in propan-2-ol (2 mL) was heated at 110° C. for 24 h. The solvent was evaporated and the crude mixture (0.38 g) was purified by reverse phase chromatography (water/acetonitrile) to give the title compound (0.08 g, 57% of yield).

δ $^1$H-NMR (DMSO-d$_6$): 6.98 (s, 1H), 7.26 (dd, 1H), 7.42 (m, 2H), 7.62 (dt, 1H), 8.36-8.41 (m, 3H).

ESI/MS m/e: 307 ([M+H]$^+$, $C_{16}H_{11}FN_6$).

Example 57

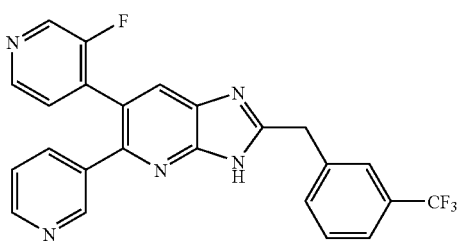

6-(3-Fluoropyridin-4-yl)-5-pyridin-3-yl-2-[3-(trifluoromethyl)benzyl]-3H-imidazo[4,5-b]pyridine Obtained (0.026 g, 42% of yield) from 3"-fluoro-3,2':3',4"-terpyridine-5',6'-diamine (Intermediate 1, 0.1 g, 0.356 mmol) and [3-(trifluoromethyl)phenyl]acetyl chloride (0.075 g, 0.337 mmol) following the procedure described in Example 37.

δ $^1$H-NMR (CDCl$_3$): 4.47 (s, 2H), 7.04-7.11 (m, 1H), 7.25-7.60 (m, 6H), 7.66 (s, 1H), 8.04 (s, 1H), 8.26 (d, 1H), 8.40 (m, 1H), 8.46 (d, 1H), 9.31 (s, 1H).

ESI/MS m/e: 450 ([M+H]$^+$, C$_{24}$H$_{15}$F$_4$N$_5$).

Example 58

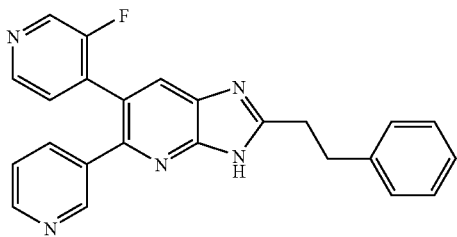

6-(3-Fluoropyridin-4-yl)-2-(2-phenylethyl)-5-pyridin-3-yl-3H-imidazo[4,5-b]pyridine Obtained (0.060 g, 49% of yield) from 3"-fluoro-3,2':3',4"-terpyridine-5',6'-diamine (Intermediate 1, 0.1 g, 0.356 mmol) and 3-phenylpropanol chloride (0.080 mL, 0.534 mmol) following the procedure described in Example 37.

δ $^1$H-NMR (CDCl$_3$): 3.24 (m, 4H), 7.11 (dd, 1H), 7.20-7.33 (m, 6H), 7.46 (d, 1H), 8.04 (s, 1H), 8.40 (d, 1H), 8.45 (d, 1H), 8.49 (dd, 1H), 9.23 (s, 1H), 12.76 (s, 1H).

ESI/MS m/e: 396 ([M+H]$^+$, C$_{24}$H$_{18}$FN$_5$).

Example 59

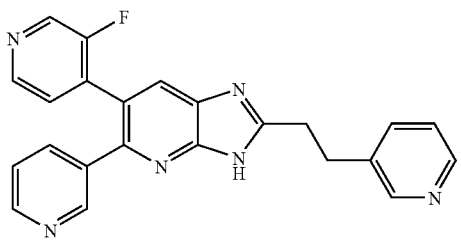

6-(3-Fluoropyridin-4-yl)-5-pyridin-3-yl-2-(2-pyridin-3-ylethyl)-3H-imidazo[4,5-b]pyridine Obtained (0.02 g, 59% of yield) from 3"-fluoro-3,2':3',4"-terpyridine-5',6'-diamine (Intermediate 1, 0.1 g, 0.356 mmol) and 3-pyridin-3-ylpropanoic acid (0.070 g, 0.463 mmol) following the procedure described in Example 41.

δ $^1$H-NMR (CDCl$_3$): 3.29 (s, 4H), 7.23 (m, 3H), 7.61 (d, 2H), 8.00 (s, 1H), 8.37 (d, 1H), 8.40 (d, 1H), 8.45 (m, 1H), 8.52 (d, 1H), 8.54 (d, 1H), 8.65 (d, 1H).

ESI/MS m/e: 397 ([M+H]$^+$, C$_{23}$H$_{17}$FN$_6$).

Example 60

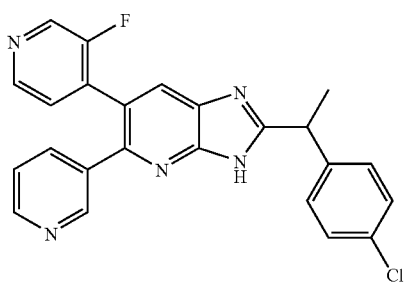

2-[1-(4-Chlorophenyl)ethyl]-6-(3-fluoropyridin-4-yl)-5-pyridin-3-yl-3H-imidazo[4,6-b]pyridine Obtained (0.035 g, 52% of yield) from 3"-fluoro-3,2':3',4"-terpyridine-5',6'-diamine (Intermediate 1, 0.15 g, 0.534 mmol) and 2-(4-chlorophenyl)propanoic acid (0.128 g, 0.694 mmol) following the procedure described in Example 41.

δ $^1$H-NMR (CDCl$_3$): 1.91 (d, 3H), 4.51 (q, 1H), 7.08 (m, 1H), 7.30 (m, 5H), 7.39 (m, 1H), 8.07 (s, 1H), 8.28 (dd, 1H), 8.41 (d, 1H), 8.47 (d, 1H), 9.24 (d, 1H), 12.58 (s, 1H).

ESI/MS m/e: 430 ([M+H]$^+$, C$_{24}$H$_{17}$ClFN$_5$).

Example 61

Step a

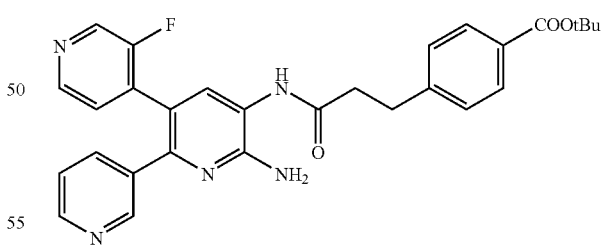

4-[2-(6'-Amino-3"-fluoro-[3,2'; 3',4"]terpyridin-5'-ylcarbamoyl)-ethyl]-benzoic acid tert-butyl ester Obtained (0.135 g, 49% of yield) from 3"-fluoro-3,2':3',4"-terpyridine-5',6'-diamine (Intermediate 1, 0.15 g, 0.534 mmol) and 3-[4-(tert-butoxycarbonyl)phenyl]propanoic acid (0.174 g, 0.694 mmol) following the procedure described in Example 41, step a.

ESI/MS m/e: 514 ([M+H]$^+$, C$_{29}$H$_{28}$FN$_5$O$_3$).

Step b

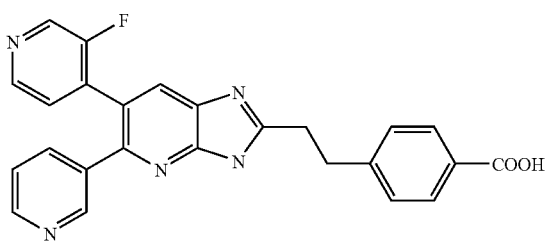

4-{2-[6-(3-Fluoro-pyridin-4-yl)-5-pyridin-3-yl-3H-imidazo[4,5-b]pyridin-2-yl]-ethyl}-benzoic acid A solution of 4-[2-(6'-Amino-3"-fluoro-[3,2':3',4"]terpyridin-5'-ylcarbamoyl)-ethyl]-benzoic acid tert-butyl ester (0.135 g, 0.263 mmol) in acetic acid (2 mL) was heated in a sealed tube at 118° C. for 16 h. The solvent was evaporated and ethyl acetate was added. The solid formed was filtered and washed with 4% sodium bicarbonate aqueous solution, water and dried to give the title compound (0.08 g, 69% of yield).
ESI/MS m/e: 440 ([M+H]$^+$, $C_{25}H_{18}FN_5O_2$).

Example 62

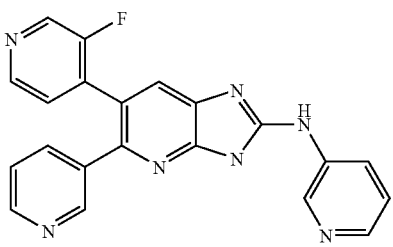

6-(3-Fluoropyridin-4-yl)-N,5-dipyridin-3-yl-3H-imidazo[4,5-b]pyridin-2-amine

To a solution of 3"-fluoro-3,2':3',4"-terpyridine-5',6'-diamine (Intermediate 1, 0.1 g, 0.356 mmol) and 3-isothiocyanatopyridine (0.06 mL, 0.534 mmol) in ethanol (2 mL), 1,3-diisopropylcarbodiimide (0.083 mL, 0.534 mmol) was added. The mixture was heated at 50° C. for 2 h. After cooling at room temperature, the solvent was evaporated. The crude mixture was purified by silica gel flash chromatography (95:5 dichloromethane/methanol) to give the title compound (0.045 g, 33% of yield).
ESI/MS m/e: 384 ([M+H]$^+$, $C_{21}H_{14}FN_7$).

Example 63

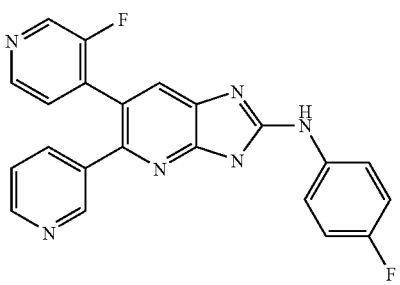

N-(4-Fluorophenyl)-6-(3-fluoropyridin-4-yl)-5-pyridin-3-yl-3H-imidazo[4,5-b]pyridin-2-amine Obtained (0.048 g, 49% of yield) from 3"-fluoro-3,2':3',4"-terpyridine-5',6'-diamine (Intermediate 1, 0.15 g, 0.534 mmol) and 1-fluoro-4-isothiocyanatobenzene (0.082 g, 0.534 mmol) following the procedure described in Example 62.
δ $^1$H-NMR (DMSO-d$_6$): 7.19 (t, 2H), 7.30 (dd, 1H), 7.47 (dd, 1H), 7.63-7.69 (m, 2H), 7.80-7.87 (m, 2H), 8.43 (m, 4H).
ESI/MS m/e: 401 ([M+H]$^+$, $C_{22}H_{14}F_2N_6$).

Example 64

Step a

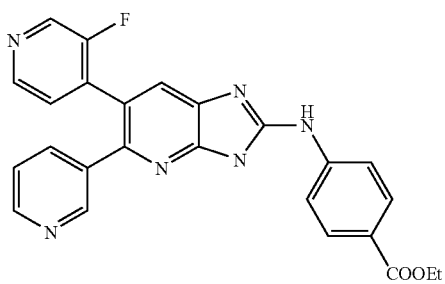

4-[6-(3-Fluoro-pyridin-4-yl)-5-pyridin-3-yl-3H-imidazo[4,5-b]pyridin-2-ylamino]-benzoic acid ethyl ester Obtained (0.120 g, 74% of yield) from 3"-fluoro-3,2':3',4"-terpyridine-5',6'-diamine (Intermediate 1, 0.10 g, 0.356 mmol) and ethyl 4-isothiocyanatobenzoate (0.111 g, 0.534 mmol) following the procedure described in Example 62.
ESI/MS m/e: 455 ([M+H]$^+$, $C_{25}H_{19}FN_6O_2$).

Step b

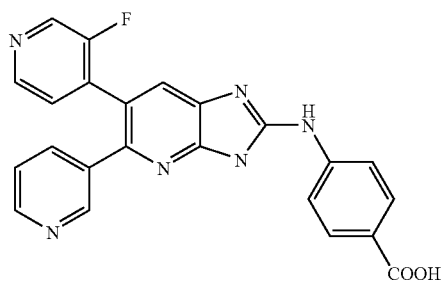

4-{[6-(3-Fluoropyridin-4-yl)-5-pyridin-3-yl-3H-imidazo[4,5-b]pyridin-2-yl]amino}benzoic acid To a solution of 4-[6-(3-fluoro-pyridin-4-yl)-5-pyridin-3-yl-3H-imidazo[4,5-b]pyridin-2-ylamino]-benzoic acid ethyl ester (0.120 g, 0.264 mmol) in ethanol (3.5 mL), 2N sodium hydroxide aqueous solution (0.53 mL) was added. The mixture was stirred at room temperature overnight and then neutralised with 2N hydrogen chloride aqueous solution. The solvent was evaporated and the crude mixture (0.18 g) was purified by reverse phase chromatography (water/acetonitrile) to give the title compound (0.02 g, 18% of yield).
ESI/MS m/e: 427 ([M+H]$^+$, $C_{23}H_{15}FN_6O_2$).

Example 65

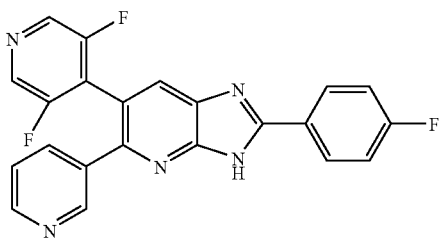

6-(3,5-Difluoropyridin-4-yl)-2-(4-fluorophenyl)-5-pyridin-3-yl-3H-imidazo[4,5-b]pyridine Obtained (0.037 g, 20% of yield) from 3",5"-difluoro-3,2':3',4"-terpyridine-5',6'-diamine (Intermediate 14, 0.10 g, 0.33 mmol) and 4-fluorobenzoyl chloride (0.059 mL, 0.5 mmol) following the procedure described in Example 37.

ESI/MS m/e: 404 ([M+H]$^+$, $C_{22}H_{12}F_3N_5$).

Example 66

Step a

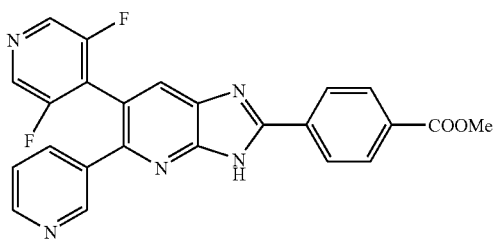

Methyl 4-[6-(3,5-difluoropyridin-4-yl)-5-pyridin-3-yl-3H-imidazo[4,5-b]pyridin-2-yl]benzoate Obtained (0.050 g, 70% of yield) from 3",5"-difluoro-3,2':3',4"-terpyridine-5',6'-diamine (Intermediate 14, 0.10 g, 0.33 mmol) and 4-(methoxycarbonyl)benzoic acid (0.078 g, 0.43 mmol) following the procedure described in Example 41.

ESI/MS m/e: 404 ([M+H]$^+$, $C_{22}H_{12}F_3N_5$).

Step b

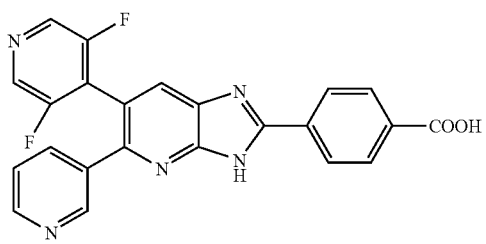

4-[6-(3,5-Difluoropyridin-4-yl)-5-pyridin-3-yl-3H-imidazo[4,5-b]pyridin-2-yl]benzoic acid To a solution of methyl 4-[6-(3,5-difluoropyridin-4-yl)-5-pyridin-3-yl-3H-imidazo[4,5-b]pyridin-2-yl]benzoate (0.05 g, 0.11 mmol) in ethanol (1.1 mL), 2N sodium hydroxide aqueous solution (0.11 mL) was added. The mixture was heated at 60° C. for 5.5 h and then neutralised with 2N hydrogen chloride aqueous solution. The solvent was evaporated and the crude mixture was suspended in water, the solid formed was filtered and dried to give the title compound (0.04 g, 76% of yield).

δ $^1$H-NMR (MeOD): 7.41 (m, 1H), 7.86 (m, 1H), 8.22-8.33 (m, 5H), 8.42 (s, 2H), 8.50 (s, 1H), 8.57 (s, 1H).

ESI/MS m/e: 430 ([M+H]$^+$, $C_{23}H_{13}F_2N_5O_2$).

Example 67

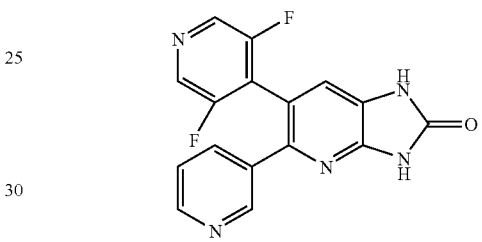

6-(3,5-Difluoropyridin-4-yl)-5-pyridin-3-yl-1,3-dihydro-2H-imidazo[4,5-b]pyridin-2-one A solution of 3",5"-difluoro-3,2':3',4"-terpyridine-5',6'-diamine (Intermediate 14, 0.045 g, 0.15 mmol), N,N'-carbonyldiimidazole (0.1 g, 0.6 mmol) and triethylamine (0.084 mL, 0.6 mmol) in THF (1.5 mL) was heated at 80° C. in a sealed tube. After 72 hours, the mixture was cooled and the solid was separated, washed with THF and dried to give the title compound (0.029 g, 59% of yield).

δ $^1$H-NMR (DMSO-d$_6$): 7.30 (dd, 1H), 7.44 (s, 1H), 7.61 (d, 1H), 8.38 (d, 1H), 8.46 (dd, 1H), 8.50 (s, 2H).

ESI/MS m/e: 326 ([M+H]+, $C_{16}H_9F_2N_5O$).

Composition Example 1

50,000 capsules, each containing 100 mg 5-(3-Fluoropyridin-4-yl)-6-pyridin-4-yl-1,3-dihydro-2H-imidazo[4,5-b]pyridin-2-one (active ingredient), were prepared according to the following formulation:

| | |
|---|---|
| Active ingredient | 5 Kg |
| Lactose monohydrate | 10 Kg |
| Colloidal silicon dioxide | 0.1 Kg |
| Corn starch | 1 Kg |
| Magnesium stearate | 0.2 Kg |

Procedure

The above ingredients were sieved through a 60 mesh sieve, and were loaded into a suitable mixer and filled into 50,000 gelatine capsules.

Composition Example 2

50,000 tablets, each containing 50 mg of 5-(3-Fluoropyridin-4-yl)-6-pyridin-4-yl-1,3-dihydro-2H-imidazo[4,5-b]pyridin-2-one (active ingredient), were prepared from the following formulation:

| Active ingredient | 2.5 Kg |
|---|---|
| Microcrystalline cellulose | 1.95 Kg |
| Spray dried lactose | 9.95 Kg |
| Carboxymethyl starch | 0.4 Kg |
| Sodium stearyl fumarate | 0.1 Kg |
| Colloidal silicon dioxide | 0.1 Kg |

Procedure

All the powders were passed through a screen with an aperture of 0.6 mm, then mixed in a suitable mixer for 20 minutes and compressed into 300 mg tablets using 9 mm disc and flat bevelled punches. The disintegration time of the tablets was about 3 minutes.

The invention claimed is:

1. A compound of formula (I)

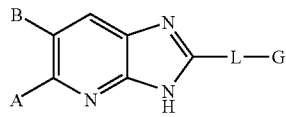

wherein:

A is a monocyclic nitrogen-containing heteroaryl group optionally substituted by one or more substituents independently chosen from halogen atoms, $C_{1-4}$alkyl, $C_{3-7}$cycloalkyl, $C_{3-7}$cycloalkyl-$C_{1-4}$alkyl, $C_{1-4}$alkoxy, aryl-$C_{1-4}$alkoxy, $C_{1-4}$alkylthio, mono or di-$C_{1-4}$alkylamino, trifluoromethyl, hydroxy and cyano groups;

B is a monocyclic nitrogen-containing heteroaryl group optionally substituted by one or more substituents independently chosen from halogen atoms, $C_{1-4}$alkyl, $C_{3-7}$cycloalkyl, $C_{3-7}$cycloalkyl-$C_{1-4}$alkyl, $C_{1-4}$alkoxy, aryl-$C_{1-4}$alkoxy, $C_{1-4}$alkylthio, mono or di-$C_{1-4}$alkylamino, trifluoromethyl, hydroxy and cyano groups;

L is a linking group chosen from a direct bond, —(CRR')$_n$—, —NR—, —S—, —O— and —CO—; wherein n is an integer from 0 to 2;

G is a group chosen from —H, —OH, $C_{3-7}$cycloalkyl; $C_{1-6}$alkyl, aryl, heteroaryl and nitrogen-containing saturated heterocyclic rings, wherein the aryl, heteroaryl and nitrogen-containing saturated heterocyclic groups are unsubstituted or substituted by one or more groups chosen from halogen atoms, $C_{1-4}$alkyl, $C_{1-4}$alkylthio, $C_{1-4}$alkoxy, mono- or di-$C_{1-4}$alkylamino, cyano, trifluoromethyl, —COOH and —CO—O—$C_{1-4}$ alkyl groups; and R and R' are each independently chosen from a hydrogen atom and $C_{1-4}$alkyl groups;

or a pharmaceutically acceptable salt thereof or a N-oxide thereof.

2. The compound according to claim 1, wherein A is an optionally substituted pyridine or an optionally substituted oxazole group.

3. The compound according to claim 1, wherein A is an unsubstituted pyridine ring or a pyridine ring substituted with one halogen atom.

4. The compound according to claim 1, wherein B is an optionally substituted pyridine or pyrimidine group.

5. The compound according to claim 4, wherein B is an unsubstituted pyridine group or a pyridine ring substituted by one or more halogen atoms.

6. The compound according to claim 1, wherein -L-G is a moiety chosen from a hydrogen atom, a hydroxyl group, optionally substituted phenyl, optionally substituted pyridyl, optionally substituted benzyl, optionally substituted benzoyl, $C_{3-7}$cycloalkyl; $C_{1-6}$alkyl, optionally substituted morpholino, optionally substituted piperidino and optionally substituted piperazine groups wherein the optionally substituted groups may carry from 0 to 2 substituents chosen from halogen atoms, $C_{1-4}$alkyl, $C_{1-4}$alkylthio, $C_{1-4}$alkoxy, mono or di-$C_{1-4}$alkylamino, cyano, —(CO)OH, —(CO)O—$C_{1-4}$alkyl, trifluoromethyl, piperidinylmethyl, pyridinylmethyl, phenylamino and piperidinylamino.

7. The compound according to claim 1 chosen from:

6-(3-Fluoropyridin-4-yl)-5-pyridin-3-yl-1,3-dihydro-2H-imidazo[4,5-b]pyridin-2-one 2-Cyclopropyl-6-(3-fluoropyridin-4-yl)-5-pyridin-3-yl-3H-imidazo[4,5-b]pyridine 2-Cyclohexyl-6-(3-fluoropyridin-4-yl)-5-pyridin-3-yl-3H-imidazo[4,5-b]pyridine 6-(3-Fluoropyridin-4-yl)-2-methyl-5-pyridin-3-yl-3H-imidazo[4,5-b]pyridine 2-(4-Fluorophenyl)-6-(3-fluoropyridin-4-yl)-5-pyridin-3-yl-3H-imidazo[4,5-b]pyridine 6-(3-Fluoropyridin-4-yl)-2-(4-methoxyphenyl)-5-pyridin-3-yl-3H-imidazo[4,5-b]pyridine N-{4-[6-(3-fluoropyridin-4-yl)-5-pyridin-3-yl-3H-imidazo[4,5-b]pyridin-2-yl]phenyl}-N,N-dimethylamine 6-(3-Fluoropyridin-4-yl)-2-(4-tert-butylphenyl)-5-pyridin-3-yl-3H-imidazo[4,5-b]pyridine 6-(3-Fluoropyridin-4-yl)-5-pyridin-3-yl-2-[4-(trifluoromethyl)phenyl]-3H-imidazo[4,5-b]pyridine Methyl 4-[6-(3-fluoropyridin-4-yl)-5-pyridin-3-yl-3H-imidazo[4,5-b]pyridin-2-yl]benzoate 4-[6-(3-Fluoropyridin-4-yl)-5-pyridin-3-yl-3H-imidazo[4,5-b]pyridin-2-yl]benzoic acid 6-(3-Fluoropyridin-4-yl)-5-pyridin-3-yl-2-pyridin-4-yl-3H-imidazo[4,5-b]pyridine 2-(2,3-Dihydro-1,4-benzodioxin-6-yl)-6-(3-fluoropyridin-4-yl)-5-pyridin-3-yl-3H-imidazo[4,5-b]pyridine 6-(3-Fluoropyridin-4-yl)-2-[3-fluoro-4-(trifluoromethyl)phenyl]-5-pyridin-3-yl-3H-imidazo[4,5-b]pyridine 2-(2,4-Dichloro-5-fluorophenyl)-6-(3-fluoropyridin-4-yl)-5-pyridin-3-yl-3H-imidazo[4,5-b]pyridine 2-(4-Fluorobenzyl)-6-(3-fluoropyridin-4-yl)-5-pyridin-3-yl-3H-imidazo[4,5-b]pyridine 2-[1-(4-Chlorophenyl)-1-methylethyl]-6-(3-fluoropyridin-4-yl)-5-pyridin-3-yl-3H-imidazo[4,5-b]pyridine (3,5-Difluorophenyl)[6-(3-fluoropyridin-4-yl)-5-pyridin-3-yl-3H-imidazo[4,5-b]pyridin-2-yl]methanone N-(4-chlorophenyl)-6-(3-fluoropyridin-4-yl)-5-pyridin-3-yl-3H-imidazo[4,5-b]pyridin-2-amine 2-(4-Fluorophenyl)-5-pyridin-3-yl-6-pyridin-4-yl-3H-imidazo[4,5-b]pyridine 6-(3-Chloropyridin-4-yl)-5-pyridin-3-yl-1,3-dihydro-2H-imidazo[4,5-b]pyridin-2-one 5,6-Dipyridin-4-yl-1,3-dihydro-2H-imidazo[4,5-b]pyridin-2-one
5-(3-Fluoropyridin-4-yl)-6-pyridin-4-yl-1,3-dihydro-2H-imidazo[4,5-b]pyridin-2-one
5-(3-Chloropyridin-4-yl)-6-pyridin-4-yl-1,3-dihydro-2H-imidazo[4,5-b]pyridin-2-one
5-(3-Chloropyridin-4-yl)-2-(4-fluorophenyl)-6-pyridin-4-yl-3H-imidazo[4,5-b]pyridine
6-(3-Chloropyridin-4-yl)-5-pyridin-4-yl-1,3-dihydro-2H-imidazo[4,5-b]pyridin-2-one
6-(3-Chloropyridin-4-yl)-2-(4-fluorophenyl)-5-pyridin-4-yl-3H-imidazo[4,5-b]pyridine
5-(3-Chloropyridin-4-yl)-2-(4-fluorophenyl)-6-(3-fluoropyridin-4-yl)-3H-imidazo[4,5-b]pyridine
5,6-Bis(3-chloropyridin-4-yl)-1,3-dihydro-2H-imidazo[4,5-b]pyridin-2-one
5-(1,3-Oxazol-2-yl)-6-pyridin-4-yl-1,3-dihydro-2H-imidazo[4,5-b]pyridin-2-one
5-(1,3-Oxazol-2-yl)-6-pyridin-4-yl-3H-imidazo[4,5-b]pyridine
6-(3-Fluoropyridin-4-yl)-5-(1,3-oxazol-2-yl)-1,3-dihydro-2H-imidazo[4,5-b]pyridin-2-one
6-(3-Fluoropyridin-4-yl)-5-(1,3-oxazol-2-yl)-3H-imidazo[4,5-b]pyridine
5-(1,3-Oxazol-5-yl)-6-pyridin-4-yl-1,3-dihydro-2H-imidazo[4,5-b]pyridin-2-one
5-(1,3-Oxazol-5-yl)-6-pyridin-4-yl-3H-imidazo[4,5-b]pyridine
6-(3-Fluoropyridin-4-yl)-5-(1,3-oxazol-5-yl)-3H-imidazo[4,5-b]pyridine
2-(3-Fluoro-4-methylphenyl)-6-(3-fluoropyridin-4-yl)-5-pyridin-3-yl-3H-imidazo[4,5-b]pyridine
2-(3-Fluorophenyl)-6-(3-fluoropyridin-4-yl)-5-pyridin-3-yl-3H-imidazo[4,5-b]pyridine
6-(3-Fluoropyridin-4-yl)-2,5-dipyridin-3-yl-3H-imidazo[4,5-b]pyridine
6-(3-Fluoropyridin-4-yl)-2-pyrazin-2-yl-5-pyridin-3-yl-3H-imidazo[4,5-b]pyridine
3-[6-(3-Fluoropyridin-4-yl)-5-pyridin-3-yl-3H-imidazo[4,5-b]pyridin-2-yl]benzonitrile
3-[6-(3-Fluoropyridin-4-yl)-5-pyridin-3-yl-3H-imidazo[4,5-b]pyridin-2-yl]benzoic acid;
6-(3-Fluoropyridin-4-yl)-5-pyridin-3-yl-2-pyrimidin-5-yl-3H-imidazo[4,5-b]pyridine
6-(3-Fluoropyridin-4-yl)-2-pyridin-2-yl-5-pyridin-3-yl-3H-imidazo[4,5-b]pyridine
2-(3-Chloropyridin-4-yl)-6-(3-fluoropyridin-4-yl)-5-pyridin-3-yl-3H-imidazo[4,5-b]pyridine
6-(3-Fluoropyridin-4-yl)-2-(1-methyl-1H-imidazol-5-yl)-5-pyridin-3-yl-3H-imidazo[4,5-b]pyridine
6-(3-Fluoropyridin-4-yl)-2-(methylthio)-5-pyridin-3-yl-3H-imidazo[4,5-b]pyridine
1-[6-(3-Fluoropyridin-4-yl)-5-pyridin-3-yl-3H-imidazo[4,5-b]pyridin-2-yl]-1H-pyrazole-4-carboxylic acid
6-(3-Fluoropyridin-4-yl)-2-(1-methyl-1H-pyrazol-5-yl)-5-pyridin-3-yl-3H-imidazo[4,5-b]pyridine
6-(3-Fluoropyridin-4-yl)-2-[1-methyl-3-(trifluoromethyl)-1H-pyrazol-5-yl]-5-pyridin-3-yl-3H-imidazo[4,5-b]pyridine
2-(3,5-Dimethyl-1H-pyrazol-1-yl)-6-(3-fluoropyridin-4-yl)-5-pyridin-3-yl-3H-imidazo[4,5-b]pyridine
6-(3-Fluoropyridin-4-yl)-5-pyridin-3-yl-2-(4H-1,2,4-triazol-3-yl)-3H-imidazo[4,5-b]pyridine
6-(3-Fluoropyridin-4-yl)-2-morpholin-4-yl-5-pyridin-3-yl-3H-imidazo[4,5-b]pyridine
6-(3-Fluoropyridin-4-yl)-2-piperidin-1-yl-5-pyridin-3-yl-3H-imidazo[4,5-b]pyridine
6-(3-Fluoropyridin-4-yl)-2-(4-methylpiperazin-1-yl)-5-pyridin-3-yl-3H-imidazo[4,5-b]pyridine
6-(3-Fluoropyridin-4-yl)-5-pyridin-3-yl-3H-imidazo[4,5-b]pyridin-2-amine
6-(3-Fluoropyridin-4-yl)-5-pyridin-3-yl-2-[3-(trifluoromethyl)benzyl]-3H-imidazo[4,5-b]pyridine
6-(3-Fluoropyridin-4-yl)-2-(2-phenylethyl)-5-pyridin-3-yl-3H-imidazo[4,5-b]pyridine
6-(3-Fluoropyridin-4-yl)-5-pyridin-3-yl-2-(2-pyridin-3-ylethyl)-3H-imidazo[4,5-b]pyridine
2-[1-(4-Chlorophenyl)ethyl]-6-(3-fluoropyridin-4-yl)-5-pyridin-3-yl-3H-imidazo[4,5-b]pyridine
4-{2-[6-(3-Fluoro-pyridin-4-yl)-5-pyridin-3-yl-3H-imidazo[4,5-b]pyridin-2-yl]-ethyl}-benzoic acid
6-(3-Fluoropyridin-4-yl)-N,5-dipyridin-3-yl-3H-imidazo[4,5-b]pyridin-2-amine
N-(4-Fluorophenyl)-6-(3-fluoropyridin-4-yl)-5-pyridin-3-yl-3H-imidazo[4,5-b]pyridin-2-amine
4-{[6-(3-Fluoropyridin-4-yl)-5-pyridin-3-yl-3H-imidazo[4,5-b]pyridin-2-yl]amino}benzoic acid
6-(3,5-Difluoropyridin-4-yl)-2-(4-fluorophenyl)-5-pyridin-3-yl-3H-imidazo[4,5-b]pyridine
4-[6-(3,5-Difluoropyridin-4-yl)-5-pyridin-3-yl-3H-imidazo[4,5-b]pyridin-2-yl]benzoic acids and
6-(3,5-Difluoropyridin-4-yl)-5-pyridin-3-yl-1,3-dihydro-2H-imidazo[4,5-b]pyridin-2-one.

8. A pharmaceutical composition comprising a compound according to claim 1 and a pharmaceutically acceptable diluent or carrier.

9. A composition comprising:
(i) a compound according to claim 1; and
(ii) at least one compound chosen from (1) antagonists of M3 muscarinic receptors, (2) β2-agonists, (3) PDE4 inhibitors, (4) cortiocosteroids, (5) leukotriene D4 antagonists, (6) inhibitors of egfr-kinase, (7) p38 kinase inhibitors, (8) NK1 receptor agonists, (9) CRTh2 antagonists, (10) syk kinase inhibitors, (11) CCR3 antagonists and (12) VLA-4 antagonists; for simultaneous, separate or sequential administration.

* * * * *